US008338358B2

(12) United States Patent
Bernhardt et al.

(10) Patent No.: US 8,338,358 B2
(45) Date of Patent: Dec. 25, 2012

(54) COMPOSITIONS COMPRISING SULFONATED ESTOLIDES AND ALKYL ESTER SULFONATES, METHODS OF MAKING THEM, AND COMPOSITIONS AND PROCESSES EMPLOYING THEM

(75) Inventors: Randal J. Bernhardt, Antioch, IL (US); Lourdes R. Alonso, Deerfield, IL (US); Gregory P. Dado, Chicago, IL (US); Eddie I. Filipovic, Evanston, IL (US); Christopher A. Gariepy, Northbrook, IL (US); Ronald A. Masters, Glenview, IL (US); Dennis S. Murphy, Libertyville, IL (US); Jacqueline Maas Pytel, Libertyville, IL (US); Branko Sajic, Lincolnwood, IL (US); Irene Shapiro, Buffalo Grove, IL (US); Jeremy Aaron Weitgenant, Grayslake, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/359,266

(22) Filed: Jan. 26, 2012

(65) Prior Publication Data
US 2012/0129955 A1    May 24, 2012

Related U.S. Application Data

(63) Continuation of application No. 12/507,011, filed on Jul. 21, 2009, which is a continuation-in-part of application No. PCT/US2009/031455, filed on Jan. 20, 2009.

(60) Provisional application No. 61/022,662, filed on Jan. 22, 2008.

(51) Int. Cl.
*C11D 1/28* (2006.01)
(52) U.S. Cl. ..................................................... 510/495
(58) Field of Classification Search .................... 510/495
See application file for complete search history.

(56) References Cited

U.S. PATENT DOCUMENTS

| | | | |
|---|---|---|---|
| 2,581,375 A | 1/1952 | De Groote et al. |
| 2,743,288 A | 4/1956 | Rueggeberg et al. |
| 2,995,524 A | 8/1961 | Wylie et al. |
| 3,332,880 A | 7/1967 | Kessler et al. |
| 3,377,290 A | 4/1968 | Werner et al. |
| 3,664,961 A | 5/1972 | Norris |
| 3,668,153 A | 6/1972 | Crotty |
| 3,898,187 A | 8/1975 | Miller |
| 3,929,678 A | 12/1975 | Laughlin et al. |
| 4,228,044 A | 10/1980 | Cambre |
| 4,435,307 A | 3/1984 | Barbesgaard et al. |
| 4,438,025 A | 3/1984 | Satsuki et al. |
| 4,507,219 A | 3/1985 | Hughes |
| 4,548,744 A | 10/1985 | Connor |
| 4,561,998 A | 12/1985 | Wertz et al. |
| 4,597,898 A | 7/1986 | Vander Meer |
| 4,663,071 A | 5/1987 | Bush et al. |
| 4,816,188 A | 3/1989 | Kitano et al. |
| 4,936,551 A | 6/1990 | Behler et al. |
| 5,002,683 A | 3/1991 | Behler et al. |
| 5,071,594 A | 12/1991 | Borland et al. |
| 5,075,501 A | 12/1991 | Borland et al. |
| 5,294,726 A | 3/1994 | Behler et al. |
| 5,329,030 A | 7/1994 | Schenker et al. |
| 5,429,684 A | 7/1995 | Osberghaus et al. |
| 5,441,156 A | 8/1995 | Fabry et al. |
| 5,466,394 A | 11/1995 | de Buzzaccarini et al. |
| 5,576,282 A | 11/1996 | Miracle et al. |
| 5,622,925 A | 4/1997 | de Buzzaccarini et al. |
| 5,679,630 A | 10/1997 | Baeck et al. |
| 5,776,872 A | 7/1998 | Giret et al. |
| 5,883,062 A | 3/1999 | Addison et al. |
| 5,906,973 A | 5/1999 | Ouzounis et al. |
| 5,929,022 A | 7/1999 | Velazquez |
| 6,017,871 A | 1/2000 | Baeck et al. |
| 6,018,063 A | 1/2000 | Isbell |
| 6,048,836 A | 4/2000 | Romano et al. |
| 6,172,026 B1 | 1/2001 | Ospinal |
| 6,242,406 B1 | 6/2001 | Katsuda et al. |
| 6,294,513 B1 | 9/2001 | Jensen et al. |
| 6,306,812 B1 | 10/2001 | Perkins et al. |
| 6,326,348 B1 | 12/2001 | Vinson et al. |
| 6,605,579 B1 | 8/2003 | Arvanitidou et al. |
| 6,627,592 B1 | 9/2003 | Shamayeli |
| 6,797,011 B2 | 9/2004 | Blangiforti |

(Continued)

FOREIGN PATENT DOCUMENTS
DE    2247832    4/1973
(Continued)

OTHER PUBLICATIONS

International Preliminary Report on Patentability, in PCT/US10/29654, dated Jan. 24, 2012.
PCT International Search Report and Written Opinion from International Application No. PCT/US2009/031455 mailed on Aug. 17, 2009.
PCT International Search Report and Written Opinion from International Application No. PCT/US2009/031608 mailed on Oct. 29, 2009.
PCT International Search Report and Written Opinion from International Application No. PCT/US2009/051299 mailed on Oct. 20, 2009.

(Continued)

*Primary Examiner* — John Hardee
(74) *Attorney, Agent, or Firm* — McAndrews, Held & Malloy, Ltd.

(57) ABSTRACT

Compositions comprising sulfo-estolides and alkyl ester sulfonates are described. Detergent formulations, such as laundry detergents, softeners, and other materials, containing any of these materials are disclosed, as well as personal care formulations, hard surface cleaner formulations, and automatic dishwasher detergent formulations. Laundry methods employing these formulations are also disclosed. These formulations are useful as laundry detergents and can be biodegradable, heavy duty liquids, 2× or 3× and up to 6× concentrates, low foaming, and/or effective in a high efficiency washing machine.

16 Claims, No Drawings

U.S. PATENT DOCUMENTS

| | | | |
|---|---|---|---|
| 6,878,695 B2 | 4/2005 | Woo et al. | |
| 6,903,064 B1 | 6/2005 | Kasturi et al. | |
| 6,949,498 B2 | 9/2005 | Murphy et al. | |
| 6,953,849 B2 | 10/2005 | Vali | |
| 7,326,675 B2 | 2/2008 | Schneiderman et al. | |
| 7,666,828 B2 * | 2/2010 | Bernhardt et al. | 510/495 |
| 7,879,790 B2 * | 2/2011 | Bernhardt et al. | 510/495 |
| 7,884,064 B2 * | 2/2011 | Bernhardt et al. | 510/495 |
| 7,998,920 B2 * | 8/2011 | Murphy et al. | 510/495 |
| 8,058,223 B2 * | 11/2011 | Bernhardt et al. | 510/495 |
| 8,119,588 B2 * | 2/2012 | Bernhardt et al. | 510/495 |
| 8,124,577 B2 * | 2/2012 | Bernhardt et al. | 510/495 |
| 8,129,328 B2 * | 3/2012 | Bernhardt et al. | 510/495 |
| 2002/0039979 A1 | 4/2002 | Aszman | |
| 2002/0187909 A1 | 12/2002 | Gupta et al. | |
| 2004/0071653 A1 | 4/2004 | Bratescu et al. | |
| 2004/0242920 A1 | 12/2004 | Dado et al. | |
| 2005/0215456 A1 | 9/2005 | Goo et al. | |
| 2007/0128129 A1 | 6/2007 | Stehr | |
| 2007/0202069 A1 | 8/2007 | Tamareselvy | |
| 2008/0015135 A1 | 1/2008 | Debuzzaccarini | |
| 2009/0054294 A1 | 2/2009 | Theiler | |

FOREIGN PATENT DOCUMENTS

| | | | |
|---|---|---|---|
| DE | 3926345 | A1 | 2/1991 |
| EP | 0070077 | | 1/1983 |
| EP | 0075996 | | 4/1983 |
| EP | 0094118 | | 11/1983 |
| EP | 111965 | | 6/1984 |
| EP | 111984 | | 6/1984 |
| EP | 112592 | | 7/1984 |
| EP | 0485500 | A1 | 5/1992 |
| EP | 0 511 091 | A1 | 10/1992 |
| GB | 1 047 772 | A1 | 11/1966 |
| GB | 1082179 | | 9/1967 |
| GB | 1278421 | A1 | 6/1972 |
| GB | 1372034 | | 10/1974 |
| GB | 1 380 390 | A | 1/1975 |
| GB | 2075028 | | 11/1981 |
| GB | 2095275 | | 9/1982 |
| GB | 2247832 | | 3/1992 |
| WO | 88/09367 | | 12/1988 |
| WO | 89/09813 | | 10/1989 |
| WO | WO 90/02116 | A1 | 3/1990 |
| WO | WO 91/02045 | A1 | 2/1991 |
| WO | WO 91/13961 | A1 | 9/1991 |
| WO | 92/05249 | | 4/1992 |
| WO | WO 92/15660 | A1 | 9/1992 |
| WO | 99/05242 | | 2/1999 |
| WO | 00/18363 | A1 | 4/2000 |
| WO | 00/58430 | A1 | 10/2000 |
| WO | 01/53247 | A1 | 7/2001 |
| WO | 2005/113735 | A1 | 12/2005 |
| WO | 2006/062665 | | 6/2006 |
| WO | 2008/137769 | | 11/2008 |
| WO | 2009/094336 | | 7/2009 |

OTHER PUBLICATIONS

PCT International Search Report and Written Opinion from International Application No. PCT/US2009/051318 mailed on Oct. 22, 2009.
PCT International Search Report and Written Opinion from International Application No. PCT/US2009/051319 mailed on Oct. 20, 2009.
PCT International Search Report and Written Opinion from International Application No. PCT/US2009/051464 mailed on Oct. 22, 2009.
PCT International Search Report and Written Opinion from International Application No. PCT/US2009/051312 mailed on Mar. 24, 2010.
Office Action in U.S. Appl. No. 12/506,861 dated Apr. 21, 2010.
Office Action in U.S. Appl. No. 12/506,861 dated Aug. 19, 2010.
Office Action in U.S. Appl. No. 12/506,977 dated Aug. 18, 2010.
European Patent Office, Communication with European Search Report in European patent application No. 09009490.5 dated May 17, 2010.
International Search Report and Written Opinion, in PCT/US10/29654, dated May 25, 2010.
Office Action in U.S. Appl. No. 12/506,930, dated Jun. 27, 2011.
Foams Fundamentals and Applications in the Petrochemical Industry, edited by Laurier L. Schraman (1994).
Handbook of Water-Soluble Gums and Resins, Glossary and Chapters 3, 4, 12 and 13, Robert L Davidson, McGraw-Hill Book Co., New York, NY (1980).
Stein et al., J. Amer. Oil Chemists Soc., 52:323-329 (1975).
Knaggs et al., J. Amer. Oil Chemists Soc., 42(9):805-810 (1965).
Kato et al., J. Surfactants and Detergents, 6(4):331-337 (2003).
Kirk-Othmer, Encyclopedia of Chemical Technology, 5th ed., vol. 23, Wiley-Interscience, Hoboken, NJ (2007), "Sulfonation and Sulfation", pp. 513-562.
McCutcheons' 2009 Functional Materials of North American Edition, vol. 2, pp. 239-246 (2009).
Neiditch et al., J. Amer. Oil Chemists Soc., 57(12):426-429 (1980).
Office Action in U.S. Appl. No. 12/353,751, dated Dec. 1, 2009.
Office Action in U.S. Appl. No. 12/353,751, dated Nov. 17, 2009.
Office Action in U.S. Appl. No. 12/506,977, dated Apr. 16, 2010.
Steinberg, Preservatives for Cosmetics Manual, 2nd Ed., by David S. Steinbens (2006).
Sauls et al., J. Amer. Oil Chemists Soc., 33(9):383-389 (1956).
SDA "Washers and Detergents" publication 2005; http://www.cleaning101.com/laundry/HE.pdf.
Surfactants and Interfacial Phenomena, 3rd ed., by Milton Rosen, published by John Wiley & Sons, Inc., Hoboken, NJ (2004).

* cited by examiner

COMPOSITIONS COMPRISING SULFONATED ESTOLIDES AND ALKYL ESTER SULFONATES, METHODS OF MAKING THEM, AND COMPOSITIONS AND PROCESSES EMPLOYING THEM

RELATED APPLICATIONS

This application is a continuation of U.S. application Ser. No. 12/507,011, filed on Jul. 21, 2009, which was a continuation-in-part of International Application No. PCT/US09/31455, filed Jan. 20, 2009 entitled "Sulfonated Estolides And Other Derivatives Of Fatty Acids, Methods Of Making Them, And Compositions And Processes Employing Them", which claims priority to U.S. Provisional Application Ser. No. 61/022,662 entitled, "Sulfonated Estolides and Other Derivatives of Fatty Acids, Methods of Making Them, and Compositions and Processes Employing Them" filed on Jan. 22, 2008, the complete subject matters of which are incorporated herein by reference in their entireties.

BACKGROUND OF THE INVENTION

The present technology, in general, relates to compositions comprising sulfo-estolides and alkyl ester sulfonates. More particularly, the present technology relates to compositions comprising sulfo-estolides derivatives and salts of sulfo-estolides, and methyl ester sulfonates.

BRIEF SUMMARY OF THE INVENTION

In at least one aspect, the present technology provides a composition comprising one or more alkyl ester sulfonates and one or more compounds having the following general Formula 1:

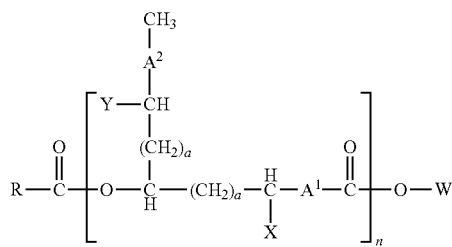

wherein n is an integer from about 1 to about 30, alternatively about 1 to about 10, alternatively 1 to 4, alternatively 1, 2, or 3, alternatively 1 or 2, alternatively 1; or mixtures thereof; one of X and Y is $SO_3$—Z, the other of X and Y is H (i.e., a hydrogen atom), and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from about 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation.

In another aspect, the present technology provides a method of laundering fabrics using one or more compositions of the presently described technology herein comprising the steps of placing one or more fabric articles to be laundered in a high efficiency or regular washing machine; placing a sufficient amount of one or more compositions of the present technology in the high efficiency or regular washing machine to provide a concentration of the composition in water of from about 0.001% by weight to about 5% by weight when the high efficiency washing machine is operated in a wash cycle; and actuating the wash cycle of the high efficiency or regular washing machine to launder the one or more fabric articles.

In a still further aspect, the present technology provides a method for hand laundering fabrics using one or more compositions of the presently described technology herein comprising the steps of placing one or more fabric articles to be hand laundered into a receptacle containing water; placing a sufficient amount of one or more composition of the present technology into the receptacle to provide a concentration of the composition in water of from about 0.001% by weight to about 5% by weight; and hand washing the fabric article in the receptacle to launder the fabric article.

In at least one other aspect, the present technology provides a method for laundering one or more fabric articles using at least one composition of the presently described technology herein, comprising the steps of placing one or more fabric articles to be laundered in a high efficiency or regular washing machine that uses a washing medium to launder clothes; providing the composition comprising from about 1% to about 99% by weight, alternatively from about 2% to about 90% by weight, of a sulfo-estolide and from about 2% to about 50% by weight of an alkyl ester sulfonate; placing in the high efficiency or regular loading washing machine a sufficient amount of the at least one compositions of the present technology to provide a concentration of the composition in the washing medium of from about 0.001% by weight to about 5% by weight when the machine is operated in a wash cycle; and actuating the wash cycle of the high efficiency or regular washing machine to launder the one or more fabric articles.

In at least one additional aspect, the present technology provides a method of reducing the viscosity of at least one composition comprising at least one surfactant in water, the method comprising the step of including in the at least one composition a sufficient amount of one or more compounds according to Formula 1 (described above), or mixtures thereof, effective to reduce the viscosity of the composition.

Further, at least one aspect of the present technology provides at least one surfactant composition comprising at least one surfactant, water, and an amount of one or more compositions of the present technology described herein, or mixtures thereof, effective to reduce the viscosity of the surfactant composition.

In addition, another aspect of the present technology provides a method of reducing the foam production of at least one composition comprising at least one surfactant in water, the method comprising the step of including in the composition an amount of one or more compositions of the presently described technology effective to reduce the foam production of the composition.

Furthermore, in another aspect, the present technology provides at least one surfactant composition comprising one or more surfactants, water, and a sufficient amount of one or more compositions of the presently described technology herein, effective to reduce the foam production of the surfactant composition.

Interestingly, the present technology also provides in a still further aspect, a method of cleaning at least one substrate, comprising the steps of providing at least one composition comprising a first surfactant comprising one or more compounds according to Formula 1, and a second surfactant comprising at least one anionic, cationic, nonionic, ampholytic, zwitterionic surfactant or combinations thereof; contacting a soiled substrate with the composition; and removing the composition and soil from the substrate.

As a still further aspect, the present technology provides a laundry detergent composition, comprising from about 5% to about 90% by weight of at least one compound according to general Formula 1:

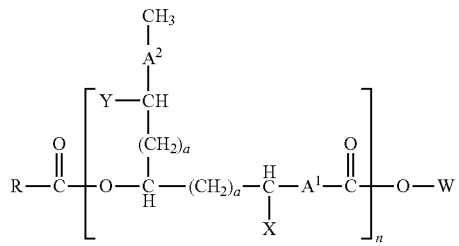

wherein n is an integer from about 1 to about 30, alternatively about 1 to about 10, alternatively 1 to 4, alternatively 1, 2, or 3, alternatively 1 or 2, alternatively 1; or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 4% to about 50% by weight of at least one alkyl ester sulfonate (for example, a $C_{16}$ alpha methyl ester sulfonate, a $C_{12}$ alpha methyl ester sulfonate, or a blend of $C_{12}$-$C_{18}$ alpha methyl ester sulfonates); from 0% to about 25% by weight of cocamide diethanolamine, and wherein the composition has a pH value in the range of about 7 to about 10.

Additionally, another aspect of the present technology provides a laundry detergent composition, comprising from about 2% to about 90% by weight of one or more compounds according to general Formula 1 (described above); from 2% to 40% by weight of at least one nonionic surfactant; from 0% to 32% by weight of at least one alcohol ether sulfate; from 0.1% to 30% by weight of at least one alkyl ester sulfonate (for example, a C16 alpha methyl ester sulfonate, a C12 alpha methyl ester sulfonate, or a blend of C12-C18 alpha methyl ester sulfonates); from 0% to 6% by weight of lauryl dimethylamine oxide; from 0% to 6% by weight of $C_{12}EO_3$; from 0% to 10% by weight of coconut fatty acid; from 0% to 3% by weight of borax pentahydrate; from 0% to 6% by weight of propylene glycol; from 0% to 10% by weight of sodium citrate; from 0% to 6% by weight of triethanolamine; from 0% to 6% by weight of monoethanolamine; from 0% to 1% by weight of at least one fluorescent whitening agent; from 0% to 1.5% by weight of at least one anti-redeposition agent; from 0% to 2% by weight of at least one thickener; from 0% to 2% by weight of at least one thinner; from 0% to 2% by weight of at least one protease; from 0% to 2% by weight of at least one amylase; and from 0% to 2% by weight of at least one cellulase.

Another aspect of the present technology provides a green laundry detergent composition, comprising from about 2% to about 90% by weight of one or more compounds according to general Formula 1; and from 0.1% to about 30% by weight of at least one alkyl ester sulfonate (for example, a $C_{16}$ methyl ester sulfonate or a blend of $C_{12}$-$C_{18}$ alpha methyl ester sulfonates); from 0% to about 30% by weight of at least one $C_{12}$ methyl ester sulfonate; from 0% to about 30% by weight of sodium lauryl sulfate; from 0% to about 30% by weight of Sodium stearoyl lactylate; from 0% to about 30% by weight of sodium lauroyl lactate; from 0% to about 60% by weight of alkyl polyglucoside; from 0% to about 60% by weight of polyglycerol monoalkylate; from 0% to about 30% by weight of lauryl lactyl lactate; from 0% to about 30% by weight of saponin; from 0% to about 30% by weight of rhamnolipid; from 0% to about 30% by weight of sphingolipid; from 0% to about 30% by weight of glycolipid; from 0% to about 30% by weight of at least one abietic acid derivative; and from 0% to about 30% by weight of at least one polypeptide.

As yet another aspect of the present technology, light duty liquid (LDL) detergent compositions are provided that contain sulfo-estolides and alkyl ester sulfonates as surfactants. The sulfo-estolide surfactants include sulfo-estolide derivatives and salts of sulfo-estolides. Applications and/or processes of utilizing the presently described sulfo-estolide surfactants, in particular as a component within light duty liquid detergent compositions and/or formulations, are also disclosed.

In another aspect, the present technology provides a liquid laundry detergent composition, comprising about 1% to about 99% by weight of at least one compound according to general Formula 1; about 0.1% to about 50% by weight of at least one alkyl ester sulfonate; about 0.5% to about 3% by weight of magnesium sulfate; 0% to about 40% by weight of at least one additional surfactant; and about 1% to about 99% by weight of water. Other components disclosed for inclusion in liquid laundry detergent compositions can also be included.

As a further aspect of the present technology, formulations of liquid personal care compositions are provided, such as, but not limited to, liquid hand soaps, body wash, shampoos, 2-in-1 shampoos, antidandruff shampoos, facial cleaners and others. The present personal care formulations comprise one or more compounds according to general Formula 1 and one or more alkyl ester sulfonates, among other components. Such formulations may include about 0.1% to about 85% by weight of at least one alkyl ester sulfonate; and about 1% to about 99% by weight of at least one carrier.

As another aspect of the present technology, a low-foaming liquid machine dishwashing detergent composition is provided, which comprises about 0.1% to about 20% by active weight of one or more surfactants of general Formula 1; about 0.1% to about 20% by weight of at least one alkyl ester sulfonate; about 0.01% to about 10% by active weight of at least one enzyme. The balance of the composition may be a carrier and/or other components. The low-foaming liquid machine dishwashing detergent composition has a pH from about 9 to about 14.

As yet another aspect of the present technology, formulations of hard surface cleaning compositions and other general purpose cleaning compositions are provided. Such formulations comprises about 1% to about 99% by weight of at least one surfactant according to general Formula 1; about 0.1% to about 85% of at least one alkyl ester sulphonate; and about 1% to about 99% of at least one carrier.

As another aspect of the present technology, formulations are provided which comprise one or more compounds according to general Formula 1 and one or more alkyl ester sulfonates (among other components) where W in general Formula 1 is a sodium or potassium cation, H, or an alkyl or substituted alkyl group, and Z in general Formula 1 is a sodium or potassium cation. Such formulations include heavy duty liquid laundry detergent compositions, light duty liquid laundry detergent compositions, and others.

DETAILED DESCRIPTION OF THE INVENTION

The present technology, in general, relates to sulfo-estolides. More particularly, the present technology relates to sulfo-estolides derivatives and salts of sulfo-estolides, their methods of manufacture and the various applications and/or processes of utilizing them. The compositions described here include, but are not limited to, sulfo-estolides having the structure of general Formula 1:

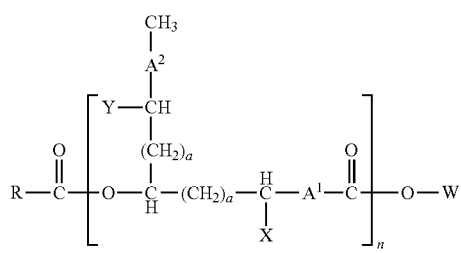

In general Formula 1:

n is an integer from about 1 to about 30, alternatively about 1 to about 10, alternatively 1 to 4, alternatively 1, 2, or 3, alternatively 1 or 2, alternatively 1; or a mixture thereof;

One of X and Y is $SO_3^-Z$, the other of X and Y is H (i.e., a hydrogen atom), and X and Y are independently assigned in each repeating unit;

$A^1$ and $A^2$ are independently selected linear or branched, saturated or unsaturated, substituted or unsubstituted alkyl diradicals, where the total number of carbons for each repeating unit is independent and in the range of $C_8$ to $C_{22}$. As defined here, the term "alkyl diradical" is meant to refer to a linking hydrocarbon or alkylene segment, for example but by no means limited to —$(CH_2)_3$—, —$(CH_2)_4$—, —$(CH_2)_5$—, and so forth;

a is 0, 1, or 2, and is independently assigned in each repeating unit. When a=0, 1, or 2, the functional group corresponds to an alpha-sulfo-estolide, beta-sulfo-estolide, or gamma-sulfo-estolide, respectively;

R can be linear or branched, saturated or unsaturated, substituted or un-substituted hydrocarbon, wherein the total number of carbon atoms can be from about 1 to about 24. In at least one embodiment, R has from about 7 to about 21 carbon atoms, alternatively from about 8 to about 16 carbon atoms, and can be a saturated or unsaturated linear or branched hydrocarbon, a linear or branched hydroxyalkane sulfonate, or a linear or branched alkene sulfonate. For example, in one embodiment, $A^1$ and $A^2$ are linear alkyl diradicals and R is saturated or unsaturated linear hydrocarbon, linear hydroxyalkane sulfonate, or linear alkene sulfonate having from about 7 to about 21, alternatively from about 8 to about 16 carbons;

W is a monovalent or divalent metal; ammonium; substituted ammonium; H; or a linear or branched, substituted or unsubstituted alkyl having from about 1 to about 22 carbon atoms. For example, W can be an alkali or alkaline earth metal cation. Alternatively, W can be a glycerine joined by an ester linkage, e.g., a substituted C3 alkyl such that the structure of general Formula 1 is incorporated one or more times as an ester in a monoglyceride, a diglyceride, or a triglyceride.

Z is H or a monovalent or divalent metal cation, ammonium or substituted ammonium cation, preferably an alkali or alkaline earth metal cation, for example potassium, sodium, calcium, or magnesium, with potassium being preferred in certain embodiments. For example, it has been shown that at least in some embodiments, a heavy duty liquid laundry concentrate containing a potassium salt is significantly lower in viscosity than a comparable composition that contains the same amount of a sodium salt.

The above structure is illustrative of the sulfo-estolide products that may be derived from, for example, linear unsaturated fatty acid feedstocks. It is understood that sultone hydrolyzed products and structures of a comparable nature may be derived from branched and/or substituted unsaturated fatty acids or mixtures of linear and branched and/or substituted unsaturated fatty acids.

Additional sulfo-estolide compositions may be produced from fatty acid feedstocks comprising polyunsaturated fatty acids, where $A^1$ and $A^2$ may be independently selected from the set of alkyl diradicals that are: a) saturated; b) unsaturated, c) unsaturated and substituted with a sulfonate group, d) substituted with a hydroxyl group and a sulfonate group; d) substituted with a ester group and a sulfonate group (i.e., a sulfo-estolide).

In another embodiment of the present technology, the sulfo-estolide compositions are comprised of carboxylic esters, or are reported in an ester analysis as carboxylic esters. Although it is contemplated that at least some of these carboxylic esters are sulfo-estolides, the presently described technology is not limited by the accuracy of this belief, for example the compositions may contain carboxylic esters wherein X and Y within one or more repeating units, in general Formula 1, are both H.

In another embodiment of the present technology, the sulfo-estolide compositions are comprised of sulfo-estolide of general Formula 1 and a non-sulfonated estolide which comprises two or more fatty acid chains that does not contain a sulfonate group.

Definitions

The term "sulfo-estolide" ("SE") is used here to describe general Formula 1. The term "partially hydrolyzed sulfo-estolide" ("PHSE") describes compositions of general Formula 1 wherein the esters have been partially hydrolyzed between (1% to 95%). The term "hydrolyzed sulfo-estolide" ("HSE") describes compositions of general Formula 1 wherein the esters have been fully hydrolyzed (>95%).

The term "sultone hydrolyzed product" ("SHP") is used here to describe salts of sulfo-estolides that are produced from feedstock comprising unsaturated fatty acids by a process comprising the steps of sulfonation with $SO_3$, neutralization, and hydrolysis of sultones. The neutralization and hydrolysis are conducted at a level of caustic addition that maintains the pH in the range from about 4 to about 10

The resulting product contains carboxylic acid esters at a level that corresponds to about 5 to about 95 mol %, alternatively about 20 to about 60 mol %, alternatively about 20 to about 45 mol %, alternatively about 30 to about 45 mol % of the total carboxylic functionality in the composition. It is contemplated that none or few of the esters (whether they are sulfo-estolides or not) are hydrolyzed in process of making SHP. By processing at a low temperature and neutralizing the acid as it leaves the sulfonator as quickly as possible, it is contemplated that lower ester levels will be obtained. Through optimization of process conditions for production of esters, it is contemplated that products that have higher ester content will be obtained. For example, it is contemplated that the ester content may be obtained at lower and/or higher levels through the selection of the molar ratio of $SO_3$ to alkene functionality used in the sulfonation step, or alternatively or in addition, through the selection of the amount of monounsaturated and/or polyunsaturated fatty acids comprising the unsaturated fatty acid feedstock.

The term "ester hydrolyzed product" ("EHP") is used here to describe a sulfonate composition that is produced from unsaturated fatty acids by sulfonation with $SO_3$ to produce sulfo-estolide and subsequent hydrolysis of greater than about 95% of the carboxylic esters. For example the resulting product may have a carboxylic ester content that corresponds to less than about 5 mol %, alternatively less than about 2 mol %, alternatively less than about 1 mol % of the total carboxylic functionality in the composition.

The term "partially ester hydrolyzed products" ("PEHP") is used here to describe salts of sulfo-estolides that are produced from unsaturated fatty acids by sulfonation with $SO_3$ and hydrolysis of a portion of the carboxylic esters. The molar percentage of hydrolysis of carboxylic esters that is realized is from about 1% to about 95%, alternatively from about 5% to about 90%, alternatively from about 10% to about 90%, alternatively from about 20% to about 90%.

As defined here, the term "free alkalinity" is meant to refer to the total amount of carboxylate anion and hydroxide present in a composition, as may be measured by, for example, potentiometric titration of an aqueous solution with aqueous strong acid, for example HCl, to an endpoint of about pH 3 to about pH 4.5, or alternatively to bromophenol blue endpoint.

As defined here, the term "free caustic" is meant to refer to the total amount of excess strong alkalinity present in a composition, as may be measured by, for example potentiometric titration of an aqueous solution with aqueous strong acid, for example HCl, to an endpoint of about pH 9 to about pH 11.

A "repeating unit" means one instance of the subject matter enclosed by brackets in a formula. For example, if n=15 for a given molecule according to general Formula 1, the molecule has 15 instances of the bracketed structure. Each instance of the bracketed structure can be identical to or different from other instances of the bracketed structure. For example, the Y moiety in general Formula 1 can be H in one repeating unit and —$SO_3^-Z$ in another repeating unit of the same molecule.

Making SE or Other Carboxylic Esters

A suitable starting material for the present process is a fatty acid (fatty carboxylic acid). Fatty acids that may be suitable for use in the present technology include but are not limited to linear unsaturated fatty acids of about 8 to about 24 carbons, branched unsaturated fatty acids of about 8 to about 24 carbons, or mixtures thereof. Unsaturated fatty acids provided from commercial sources containing both saturated and unsaturated fatty acids are suitable for use in the present technology. Mixtures of saturated fatty acids and unsaturated fatty acids are also contemplated. In a non-limiting example, fatty acid mixtures that are rich in oleic acid (cis-9-octadecenoic acid) are suitable feedstocks. Other unsaturated fatty acids, for example but not limited to, trans-octadecenoic acids or palmitoleic acid may also be employed in the presently described technology.

Suitable feedstocks may be derived from vegetable and/or animal sources, including but not limited to fatty acids and fatty acid mixtures derived from canola oil, corn oil, cottonseed oil, linseed oil, olive oil, palm oil, peanut oil, rapeseed oil, safflower oil, sesame oil, soybean oil, sunflower oil, tall oil, tung oil, lard, poultry fat, BFT (bleachable fancy tallow), edible tallow, coconut oil, *cuphea* oil, yellow grease and combinations of these. Also contemplated are genetically modified or engineered oils that include but are not limited to high oleic sunflower or soybean oil. In some embodiments, the preferred unsaturated fatty acid feedstocks may contain reduced levels of polyunsaturated fatty acids, for example, less than 15%, alternatively less than 10%, alternatively less than 5% on a total weight basis. In some additional embodiments, the fatty acid feedstocks may be obtained by the partial hydrogenation of unsaturated triglycerides, for example soybean oil, followed by hydrolysis of the oil to afford fatty acids that are enriched in monounsaturated fatty acids and depleted in polyunsaturated fatty acids. The above-noted triglycerides optionally hydrogenated, can also be used as feedstocks, alone or in combination with fatty acids. Still further, in some embodiments of the presently described technology, suitable feedstocks may include those that contain appreciable amounts of saturated fatty acids, for example up to about 80%, alternatively about 50%, alternatively about 30%, alternatively about 20% saturated fatty acid by weight. Alternatively, the feedstocks may be enriched in mono unsaturated fatty acids, for example, via distillation; however, undistilled feedstocks are preferred due to lower cost.

In certain embodiments, a chain termination agent can be included in the reaction to reduce or prevent the formulation of products of general Formula 1 in which n is greater than one. The chain termination agent can be, for example, a saturated or unsaturated, substituted or unsubstituted, aliphatic or aromatic carboxylic acid having from 7 to 22 carbon atoms, or a combination of any two or more of these. The contemplated characteristic of a chain termination agent preferred for the present purpose is that it can form an ester. One class of preferred chain termination agents is a saturated fatty acid having from 8 to 22 carbon atoms, optionally from 8 to 14 carbon atoms, optionally 8, 10, or 12 carbon atoms or mixtures of these fatty acid species.

The compounds of general Formula 1 and related compounds (for example, where n=0) can be made, for example, by: a) $SO_3$ sulfonation of a fatty acid, for example oleic acid; b) neutralization with aqueous caustic to afford a sulfonate salt solution with a pH in the range of about 4 to about 10; and c) hydrolysis of the resulting sultones, maintaining the reaction mixture at a pH of about 4 to about 10. Sulfonation can be carried out, for example, using a falling film $SO_3$ process.

Alternatively, the compounds of general Formula 1 and related compounds (for example, where Z=H and W=H) can be made, for example, by falling film $SO_3$ sulfonation of a fatty acid, for example oleic acid, where the process temperature of the sulfonation is sufficient, for example greater than about 20° C., to result in the formation of carboxylic esters.

Continuous $SO_3$ sulfonation processes, including those that utilizing falling film reactors such as those described in Kirk-Othmer Encyclopedia of Chemical Technology, 5th ed., Vol. 23, Wiley-Interscience, Hoboken, N.J.: 2007, entry entitled "Sulfonation and Sulfation", pp. 513-562, which is hereby incorporated by reference, are suitable for conducting the sulfonation of feedstocks comprising unsaturated fatty acids in accordance with the presently described technology. For example, a monotube concentric reactor, annular film reactor, or multitube film reactor can be used to contact an unsaturated fatty acid feedstock, for example oleic acid, with a gaseous stream of $SO_3$ that is diluted with dry air. The molar ratio of $SO_3$ to alkene functionality in the fatty acid feedstock may be from about 0.3 to about 1.3, alternatively from about 0.5 to about 1.2, alternatively from about 0.8 to about 1.1, alternatively from about 0.9 to about 1.0.

In some embodiments, a preferred ratio, for example, is less than about 0.8 so as to minimize color formation. The fatty acid feedstock is provided to the reactor at a temperature above the melting point of the feedstock, i.e. the feedstock is provided as a liquid. The sulfonation is conducted such that the reaction mass is maintained as a mobile liquid throughout the course of reaction. Preferably, a means of cooling the reaction mixture during the course of contact between the feedstock stream and the gaseous $SO_3$ stream is provided so that the sulfonic acid product is produced from the reactor at a temperature of from about 10° C. to about 80° C., alternatively from about 20° C. to about 60° C., alternatively from about 30° C. to about 60° C.

Sulfonated unsaturated fatty acid salt and sulfonated hydroxy fatty acid salt products include, for example, those sold in Europe as Polystep® OPA by Stepan Co., and as Lankropol OPA and Lankropol OPA-V by Akzo Nobel, and in the United States as Calsoft® OS-45S by Pilot Chemical.

SE is produced from the sulfonation step and comprises carboxylic esters, provided that the reaction conditions are sufficient, for example a high enough temperature of the acid stream, to promote carboxylic ester formation. While not limiting the scope of the presently described technology, the temperature at which carboxylic ester formation may occur is greater than 10° C., alternatively greater than 20° C., alternatively greater than 30° C. The sulfonic acid products may further comprise sulfonic acid esters, including but not limited to cyclic esters, i.e., sultones.

In accordance with at least one embodiment, the presently described technology provides a process of making a sulfo-estolide mixture comprising the steps of:
  providing at least one unsaturated fatty carboxylic acid having from 8 to 24 carbon atoms;
  providing at least one chain termination agent having from 4 to 24 carbon atoms;
  sulfonating the unsaturated fatty carboxylic acid to form a sulfonated intermediate; and
  reacting the chain termination agent with the sulfonated intermediate to form a sulfo-estolide mixture.

In accordance with one embodiment, the process further comprises treating the sulfo-estolide mixture under conditions effective to at least reduce the concentrations of sultone moieties, in which the degree of esterification of the carboxylic acid moieties is at least about 5% after the treating step.

In accordance with at least one other embodiment, the presently described technology provides a process of making a sulfo-estolide mixture comprising the steps of:
  providing at least one unsaturated fatty acyl containing triglyceride having from 27 to 75 carbon atoms;
  providing at least one chain termination agent having from 4 to 24 carbon atoms;
  sulfonating the triglyceride to form a sulfonated intermediate; and
  reacting the chain termination agent with the sulfonated intermediate to form a sulfo-estolide mixture.

The SE produced from sulfonation can be immediately transferred to a vessel or reactor, for example a continuous neutralizer ("CN"), for the purpose of neutralizing sulfonic acids and at least a portion of the carboxylic acids that are present. Alternatively, aging of the SE sulfonic acid may be provided for the purpose of modifying the composition of the acid, particularly with regard to an increase in the amount of esters wherein X and Y within one or more repeating units, in general Formula 1, are both H. Neutralization of the acids is accomplished by reaction with aqueous base, for example but not limited to aqueous NaOH, KOH, ammonium hydroxide, and metal carbonates. Combinations of two or more salts, such as mixed sodium and potassium salts in any proportions, are contemplated. In some embodiments, the amount of alkali that may be used in the neutralization is an amount that provides a neutralized product with a pH of about 4 to about 10. In these embodiments, the neutralized reaction mass may be produced in a way that minimizes the hydrolysis of carboxylic esters. In at least some of these embodiments, the amount of carboxylic ester hydrolysis that may occur may approach zero. When utilized, the CN may be operated with a mass fraction of acid of from about 0.1 to about 0.8, optionally about 0.5. The process can be carried out at a temperature of about 20 to about 100° C., alternatively about 55 to about 75° C., optionally about 65° C. The free alkalinity level, as measured by titration with aqueous HCl to a bromophenol blue endpoint, optionally using potash (potassium hydroxide) as the caustic, can be from 0 to about 3.5 wt. %, optionally about 2.5 wt. %. Note that all percentages are by weight in this specification, unless otherwise indicated. In a non-limiting example, the final average additions to the CN can be approximately 50% SE sulfonic acid, 35% water, and 15% caustic (50% concentration).

In some preferred embodiments, the sulfo-estolides employed in the present compositions are provided as a mixture of sodium and potassium salts of sulfo-estolides according to general Formula 1, wherein W is a sodium or potassium cation, H, or an alkyl or substituted alkyl group; and Z is a sodium or potassium cation. The sulfo-estolides can be included in a liquid composition with improved clarity and phase stability. The sodium and potassium salts can be present in a mixture in amounts sufficient to obtain a clear, homogeneous liquid product. For example, the potassium salt can be present in the mixture in a weight fraction of about 0.1 to about 0.8. This weight fraction and others referenced herein are based on the total weight of the potassium and sodium salts in the mixture. In one exemplary liquid composition, the composition has a pH value of about 6.4, and the potassium salt is present in the mixture in a weight fraction of about 0.5 to about 0.8. In another exemplary liquid composition, the composition has a pH value of about 7.5, and the potassium salt is present in the mixture in a weight fraction of about 0.1 to about 0.5. In yet another exemplary liquid composition, the composition has a pH value of about 8.5, and the potassium salt is present in the mixture in a weight fraction of about 0.3 to about 0.4. In some embodiments, the potassium cation is present in the mixture in a molar fraction of about 0.08 to about 0.87. Another exemplary composition has a pH value of about 6.4 and the potassium cation is present in the mixture in a molar fraction of about 0.43 to about 0.87. Yet another exemplary composition has a pH value of about 7.5, and the potassium cation is present in the mixture in a molar fraction of about 0.08 to about 0.43. Still another exemplary composition has a pH value of about 8.5, and the potassium cation is present in the mixture in a molar fraction of about 0.25 to about 0.34. Liquid compositions having pH values in the range of about 6 to about 8.5 are specifically contemplated. In some embodiments, the liquid composition further comprises about 3% by weight or less of inorganic sulfate.

Liquid compositions are provided which are phase-stable, clear and homogeneous for at least 14 days at a temperature of about 22° C. The compositions can have a mixture of sodium and potassium sulfo-estolide salts in a concentration of at least 50% by weight actives, alternatively at least 60% by weight actives.

As a further detailed example, a laundry detergent composition is provided which comprises about 2% to about 90% by weight of a mixture of sodium and potassium salts of sulfo-estolides according to general Formula 1, where W is a sodium or potassium cation, H, or an alkyl or substituted alkyl group, and Z is a sodium or potassium cation. The laundry detergent composition also comprises 0.1% to about 30% of at least one alkyl ester sulfonate; about 2% to about 40% by weight of at least one nonionic surfactant; 0% to about 35% by weight of at least one alcohol ether sulfate; 0% to about 6% by weight of lauryl dimethylamine oxide; 0% to about 10% by weight of oleamide diethanolamine; 0% to about 6% by weight of C12EO3; 0% to about 10% by weight of coconut fatty acid; 0% to about 3% by weight of borax pentahydrate; 0% to about 6% by weight of propylene glycol; 0% to about 10% by weight of sodium citrate; 0% to about 6% by weight of triethanolamine; 0% to about 6% by weight of monoethanolamine; 0% to about 1% by weight of at least one fluorescent whitening agent; 0% to about 1.5% by weight of at least one anti-redeposition agent; 0% to about 2% by weight of at least one thickener; 0% to about 20% by weight of at least one thinner; 0% to about 2% by weight of at least one protease; 0% to about 2% by weight of at least one amylase; and 0% to about 2% by weight of at least one cellulase. Preferably the mixture of sodium and potassium salts of sulfo-estolides is present in the composition in an amount of about 15% to about 46% by weight of the composition. The mixture of sodium and potassium salts of sulfo-estolides can provide better cleaning of grass stains on cotton than a similar detergent composition containing only a potassium sulfo-estolide salt or only a sodium sulfo-estolide salt in place of the mixture of sodium and potassium salts.

Another example of a laundry detergent composition is provided, which comprises about 2% to about 90% by weight of one or more compounds according to General Formula 1, where W is a sodium or potassium cation, H, or an alkyl or substituted alkyl group, and Z is a sodium or potassium cation. The laundry detergent composition also comprises 0.1% to about 30% of at least one alkyl ester sulfonate; about 2% to about 40% by weight of at least one nonionic surfactant; 0% to about 35% by weight of at least one or more alcohol ether sulfate; 0% to about 6% by weight of lauryl dimethylamine oxide; 0% to about 13% by weight of C12EO3; 0% to about 10% by weight of coconut fatty acid; 0% to about 10% by weight of sodium metasilicate; 0% to about 10% by weight of sodium carbonate; 0% to about 1% by weight of at least one fluorescent whitening agent; 0% to about 1.5% by weight of at least one anti-redeposition agent; 0% to about 2% by weight of at least one thickener; and 0% to about 20% by weight of at least one thinner. Preferably the mixture of sodium and potassium salts of sulfo-estolides is present in the composition in an amount of about 15% to about 60% by weight of the composition.

The compositions comprising mixtures of sulfo-estolide salts can be formed in different ways. For example, a mixture of NaOH and KOH can be used to neutralize the SE sulfonic acid intermediate. Alternatively, neutralized pure potassium salts can be mixed with neutralized pure sodium salts to form the mixture of salts. Another alternative method of forming the mixture of salts is to neutralize the SE sulfonic acid intermediate with either NaOH or KOH to form a single salt sulfo-estolide, and then use the other of NaOH or KOH or a mixture thereof, to adjust the pH at any stage of the manufacturing process, such as, for example, during sultone hydrolysis, during carboxylic ester hydrolysis, during peroxide bleaching and decomposition, or even post-bleaching. Another alternative is to introduce the counterion with the metal salt of $SO_2$ that may be added at the end of the bleaching step to reduce residual free peroxide.

In another aspect of the presently described technology, neutralization of the SE sulfonic acid may be conducted using an amount of aqueous base that is sufficient to neutralize all free acid functionality in the SE product, including carboxylic acids, and is sufficient to provide an excess of free caustic that is available to further react for the purposes of sultone hydrolysis, sulfonic acid anhydride hydrolysis, sulfonic carboxylic acid ester hydrolysis, and a desired amount of carboxylic ester hydrolysis, provided that adequate time and temperature for ester hydrolysis is subsequently provided. In one embodiment of this aspect, the amount of base is sufficient to enable from about 1% to about 95% hydrolysis of carboxylic esters. In another embodiment of this aspect, the amount of alkali is sufficient to enable hydrolysis of greater than about 95% of carboxylic esters, alternatively practically all carboxylic esters present in the sulfonic acid intermediate. In this embodiment, the resulting product that can be obtained by subsequently providing adequate time and temperature for ester hydrolysis to occur has a carboxylic ester content that may correspond to, for example, less than about 5%, alternatively less than about 2%, alternatively less than about 1% of the total carboxylic functionality in the composition. In these ways, EHP and PEHP can be produced.

Hydrolysis of Sultones

In one aspect of the presently described technology where a neutralized SE is produced with a pH of from about 4 to about 10, the neutralized product can be subjected to a hydrolysis step for the purpose of hydrolyzing sultones, sulfonic acid esters, and acid anhydrides. This sultone hydrolysis step may be conducted under conditions that prevent significant sultone hydrolysis of carboxylic esters in the product. The temperature of the sultone hydrolysis reaction mixture may be from about 20° C. to about 140° C., alternatively from about 50° C. to about 90° C. In some embodiments, the pH of the reaction mixture may be maintained in the range of about 4 to about 10 throughout the course of reaction without the need to add additional caustic. In some additional embodiments, additional caustic may be added to ensure that the pH is maintained in the range of about 4 to about 10. The sultone hydrolysis may be conducted in a continuous or batch process method and may be conducted for an amount of time necessary to result in a stabilized level of free alkalinity, as may be judged, for example, by titration to bromophenol blue endpoint with aqueous HCl.

It is contemplated that hydrolysis of sultones may be conducted at a pH above about 10 without substantial carboxylic ester hydrolysis provided that the reaction temperature and free caustic are maintained sufficiently low.

Hydrolysis of Carboxylic Esters

In one aspect of the presently described technology, carboxylic esters present in SE and optionally SHP may optionally be subjected to an alkaline hydrolysis step for the purpose of converting carboxylic esters into carboxylates to afford EHP and/or PEHP. This ester hydrolysis step may be conducted concurrently with a step to hydrolyze sultones or in a subsequent separate step. The ester hydrolysis step may be conducted in a batch, semi-batch, or continuous reaction mode. For example, the ester hydrolysis may be conducted in a stirred tank reactor, a loop reactor, a plug flow reactor, a single or multi-stage continuous stirred tank reactor, or any other reactor that can provide adequate temperature and time to afford an ester hydrolyzed product. Alkaline hydrolysis of the carboxylic esters may be conducted at a temperature of about 20° C. to about 150° C., alternatively about 50° C. to about 150° C., alternatively about 70° C. to about 150° C. In one non-limiting example, the ester hydrolysis is conducted at about 85° C. for about 4 hours.

The pH of the reaction mixture during the ester hydrolysis reaction, as measured on diluted samples, for example about 1 wt % of sample diluted in water, is greater than about 9.5, optionally greater than about 10. Since free caustic is consumed by the ester hydrolysis reaction, sufficient caustic is preferably provided to maintain the pH of reaction mixture above about 9.5. The amount of caustic that may be used in the ester hydrolysis step is preferably greater than the amount of caustic required to neutralize any free acid that may be present in the reaction mass, including carboxylic acids, and to hydrolyze sultones, sulfonic acid esters and anhydrides that may be present. In a given reaction mass, the amount of free caustic that may be available to hydrolyze carboxylic esters may be measured, for example, by potentiometric titration of an aliquot of reaction mass diluted in water with aqueous HCl to an endpoint between about pH 9 and about 10. In some embodiments, an amount of free caustic is provide that is sufficient to hydrolyze from about 1 to about 100% of carboxylic esters present in SE. If so desired, a substantial excess of free caustic relative to carboxylic ester content may be used in order to ensure a very high degree of ester hydrolysis.

In another aspect of the presently described technology, carboxylic esters present in SE may be hydrolyzed with water under acidic conditions. For example, it is contemplated that the degree of ester hydrolysis may be controlled by the amount of water that is mixed with the SE sulfonic acid, the reaction temperature, and the reaction time. Complete and partial ester hydrolysis of carboxylic esters by this method is contemplated.

It is further contemplated that the sultones, sulfonic acid esters, and/or anhydrides present in SE sulfonic acid products may be hydrolyzed with water under acidic conditions. It is contemplated that suitable reaction conditions will allow the hydrolysis of sultones, sulfonic acid esters, and/or anhydrides, and any other species that may be susceptible to acid hydrolysis to occur with or without hydrolysis of carboxylic esters.

Neutral Bleaching

In at least one embodiment, bleaching of neutralized products of SE may be conducted by treating the products with aqueous hydrogen peroxide, for example 35% $H_2O_2$, in a bleaching reaction that is conducted at a temperature of about 20° C. to about 150° C., alternatively about 50° C. to about 120° C., alternatively about 70° C. to about 100° C. Alternatively, metal hypochlorite, ozone, or any other oxidant or other material that is effective as a bleaching agent may be used. The hydrogen peroxide or alternative oxidizing agent may be used in any amount that is effective in providing a desired color reduction. For example, aqueous hydrogen peroxide may be added to provide about 0.05% to about 5% by weight active hydrogen peroxide, alternatively from about 0.1% to about 3%. The bleaching of the neutralized product may be conducted in the same step as the sultone hydrolysis, or may be conducted in a separate step. For example, if carried out concurrently, hydrogen peroxide can be added at about 2% (wt/wt) concentration (at 100% active) to a reaction vessel used to conduct sultone hydrolysis. The free alkalinity and free peroxide can be measured periodically until the targeted % free alkalinity level, for example 1.8%-2.0% is reached. If the % free alkalinity is lower than the target before sultone hydrolysis is complete, then an additional amount of base can be added to maintain the target levels. In at least one embodiment, it is preferable that the amount of free peroxide in the reaction mixture be maintained above about 20 ppm, alternatively above about 100 ppm, alternatively above about 500 ppm, so as to avoid discoloration of the reaction mass, adding additional amounts of hydrogen peroxide if necessary.

If required or desired, additional hydrogen peroxide can be added after sultone hydrolysis is completed for the purpose of enabling additional bleaching of the SHP. If required or desired, a reducing agent such as $SO_2$ or sulfurous acid, or metal salts thereof, can be added at or near the end of the bleaching step in order to reduce residual free peroxide to a desired level.

In accordance with some embodiments, it is preferable to conduct the bleaching of neutralized products of sulfo-estolides with hydrogen peroxide at a pH in the range of about 4.5 to about 7.5, alternatively about 5 to about 7, wherein these ranges correspond to pH values measured on diluted samples, for example about 1 wt % or about 2 wt % of sample diluted in water. Preferably, the pH of the bleaching reaction mixture is maintained, at least initially, below a pre-determined level that is necessary to minimize hydrogen peroxide decomposition, to prevent severe foaming of the reaction mixture, and to improve color reduction. It has been found that if the pH of the bleaching reaction mixture is at and above that pre-determined level, at least during the initial stage of bleaching reaction, substantial peroxide decomposition and severe foaming occurs. Without intending to be bound by any particular theory, it is believed that such decomposition and severe foaming may be dependent on a number of factors, including dissolved metal ions in the reaction mixture, exposure to metal reaction equipment surfaces, and bleaching reaction temperature. It is contemplated that the decomposition of bleaching agent may be altered or mitigated through the incorporation of stabilizers, including but not limited to metal chelating agents, or alternatively through the passivation of metal surfaces or the use of non-metal surface process equipment.

Adjusting pH to Improve Product Stability Against Inhomogeneity

In some preferred embodiments, a concentrated aqueous solution of SHP, PEHP, and EHP may be prepared in a process comprising at least the steps of sulfonating a feedstock comprising an unsaturated fatty acid, neutralizing the resulting SE sulfonic acid intermediate, and hydrolyzing sultones. In these preferred embodiments, it is preferable that the pH of the final concentrated aqueous solution to be stored, transported, and optionally handled in additional ways and is maintained in a pH range that enables a clear, homogeneous liquid product, free of substantial precipitation or other physical form instability. Surprisingly, it has been discovered that specific pH ranges can lead to physical instability as characterized by precipitation of solids and/or separation of liquid product into two or more layers. Inorganic salt, nonsulfonated-estolide, and fatty acid levels can be controlled to provide a substantially precipitate free phase stable physical form. The ratios of these components will be dependent upon the temperature and concentration of SE in the composition.

Acid Bleaching

One way to reduce color is by bleaching SE sulfonic acid before neutralizing, which can be referred to as acid bleaching. Acid bleaching of SE may have the advantage, by itself or in combination with additional bleaching after neutralization, of reducing the color of SE more than would normally be achieved by neutral bleaching as described above. Acid bleaching may be carried out, for example, by adding about 0.1% to about 8% active $H_2O_2$, alternatively about 0.5% to about 4% active $H_2O_2$, providing for inclusion of water at a level of about 0.1% to about 50%, alternatively about 1% to about 25%, alternatively about 3% to about 12%, and maintaining the bleaching reaction temperature from about 20° C. to about 100° C., alternatively at about 50° C. A critical aspect to SE acid bleaching is the incorporation of water into the bleaching reaction mixture such that the total water in the sulfonic acid mixture is above a level that is necessary to stabilize the hydrogen peroxide in the reaction mixture and to afford an improved bleaching result.

In at least some preferred embodiments, wherein bleached SE sulfonic acid is converted to SHP, it is preferred to maintain peroxide at a level above about 100 ppm of hydrogen peroxide, alternately about 500 ppm, throughout the sultone hydrolysis reaction. Within these embodiments, it is additionally preferred to maintain the hydrolysis reaction mixture, at least initially, at a pH below about 7.5 alternatively about 7.0, wherein these values correspond to pH values measured on diluted samples, for example about 1 wt % or about 2 wt % of sample diluted in water. In at least some embodiments, it is preferable to maintain the sultone hydrolysis reaction mixture, at least initially, at a pH in the range of about 4.5 to about 7.5, alternatively about 5 to about 7, so as to enable additional bleaching of the reaction mixture during the sultone hydrolysis reaction.

In methods comprising the step of bleaching SE sulfonic acid with aqueous hydrogen peroxide to produce a bleached acid, the acid bleaching reaction mixture may further comprise about 1 to about 500 alternatively about 5 to about 100 ppm of a transition metal cation selected from the group $Fe^{2+}$, $Fe^{3+}$, $Mn^{2+}$, $Mn^{3+}$, and $Mn^{4+}$ for the purpose of providing for a substantial improvement in bleaching result and/or acceleration of the bleaching reaction. In addition or alternatively in these methods, aqueous base may be used as a source of water in the bleaching acid reaction mixture so as to enable the production of higher solids in the final SE salt product than can be achieved in comparable processes that utilize water instead of aqueous base. In at least some instances the use of aqueous base in the bleaching acid reaction mixture can substantially increase the stability of peroxide in the reaction mixture.

Hydrogenation

Another way to reduce the color of SE, which is not believed to be known, is to use a partially hydrogenated feedstock, for example an oleic acid feedstock or a soybean oil feedstock, to reduce or eliminate polyunsaturates. In one contemplated process, the proportion of triunsaturates such as linolenic acid can be reduced or eliminated by hydrogenation. In another contemplated process, hydrogenation is carried further to reduce the percentage of polyunsaturates in the fatty acid feedstock to less than about 20%, alternatively less than 10%, alternatively less than 5%. One potential advantage of this process is that hydrogenation of polyunsaturation may produce trans fatty acids, which in this process is contemplated to lead to beneficial differences in the final composition or its performance. The hydrogenation can be carried out either on the parent oil or the fatty acid derived therefrom.

Product Descriptions

The compositions of the present technology defined by general Formula 1, are now believed by the present inventors to be comprised of complex mixtures of compounds that are monomeric, dimeric, and higher-order oligomeric species in terms of the number of originating fatty acid chains. The oligomerization in these mixtures is via the formation of ester linkages. Branched oligomers are also contemplated.

The sulfo-estolide functional group corresponds structurally to the condensation of the hydroxyl group of an internal hydroxy sulfonate of fatty acid with the carboxylic acid group of a second fatty acid chain, where the second fatty acid chain may be, but is not necessarily limited to: a) an unsaturated or saturated fatty acid; b) an internal hydroxy sulfonate of fatty acid; c) an internal alkene sulfonate or corresponding cyclic anhydride (i.e. sultone) of fatty acid; or d) an internal mono- or poly sulfo-estolide of two or more fatty acids (i.e., trimer, tetramer, etc.). The position of the sulfonate group along the back bone of the fatty acid chains is dictated by the location of the double bond in the starting material (9-octadecenoic acid for example) and the "direction" in which $SO_3$ adds across the double bond (thus, 9- and 10-sulfonate positions from oleic acid).

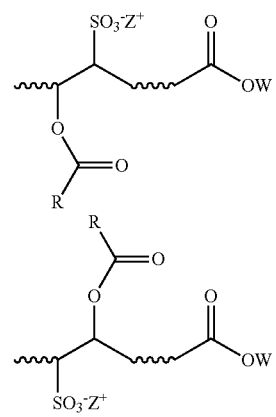

where R:

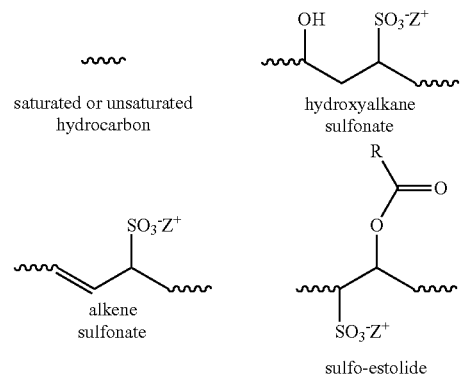

saturated or unsaturated hydrocarbon hydroxyalkane sulfonate alkene sulfonate sulfo-estolide Non-ester-containing monomeric components made by this process are believed to comprise, in part, specific internal hydroxy sulfonates of fatty acid. For example, with 9-octadecenoic acid, the sulfonate groups are believed to be attached to the 9-position and alternatively the 10-position of the fatty acid. Examples are shown below.

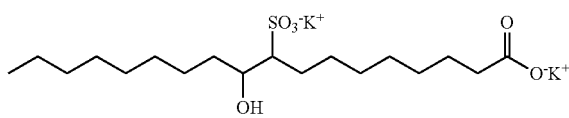

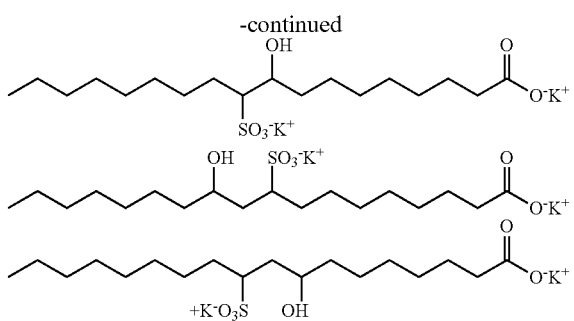

The monomeric components are further believed to comprise, in part, specific internal alkene sulfonates of fatty acid. These components may comprise cis- and/or trans-double bonds. It is also possible that compounds are present where the unsaturation is at the position of the sulfonate group (i.e., vinylic sulfonates). Examples are shown below.

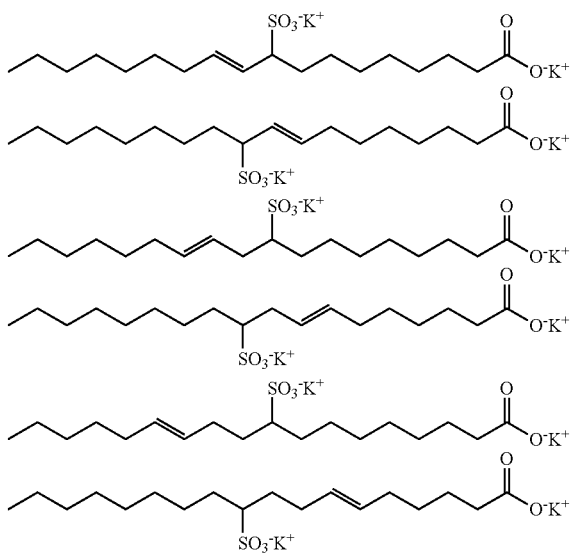

The monomeric components may further comprise disulfonated species, unsaturated fatty acids, and saturated fatty acids.

EHP is sometimes used here as a designation for sulfonated products that have been subjected to complete hydrolysis of sulfo-estolide functionality. Such hydrolysis can be accomplished by, for example, treatment of SHP with excess base under high pH conditions (for example >11) at elevated temperatures (for example 85-100° C.). EHP is believed to comprise a mixture of hydroxyalkane sulfonates and alkene sulfonates of comparable structure to the monomeric components of sulfo-estolide compositions, though not necessarily in comparable ratios. This mixture is comparable in composition to the compositions of sulfonated unsaturated fatty acids that are described in the art, for example, in T. W. Sauls and W. H. C. Rueggeberg, Journal of the American Oil Chemists Society (JAOCS), Volume 33, Number 9, September, 1956, pp 383-389.

It can be appreciated that PHEP will be comprised of elevated amounts of monomeric hydroxyalkane sulfonates and alkene sulfonates while maintaining some level of sulfo-estolide functionality.

Alkyl Ester Sulfonates

The present compositions also comprise one or more alkyl ester sulfonates. The preferred alkyl ester sulfonate surfactants, especially for laundry applications, comprise alkyl ester sulfonate surfactants of the structural formula:

$$R^3\text{—CH}(SO_3M)\text{-C}(O)\text{—}OR^4$$

where $R^3$ is a $C_8$-$C_{20}$ hydrocarbyl, preferably an alkyl or combination thereof $R^4$ is a $C_1$-$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$-$C_{16}$ alkyl, and $R^4$ is methyl, ethyl or isopropyl. The alkyl group $R^3$ may have a mixture of chain lengths. Alkyl ester sulfonates can be provided as blends of compounds with different $R^3$ substitutents. For example, a C12-C18 alkyl ester sulfonate indicates a blend of compounds having $R^3$ substitutents of $C_{12}$, $C_{18}$ and lengths in between. Examples of alkyl ester sulfonate blends include the methyl ester sulfonates where $R^3$ is $C_{10}$-$C_{16}$ alkyl, $C_{10}$-$C_{18}$ alkyl, or $C_{12}$-$C_{18}$ alkyl. Suitable alkyl ester sulfonates include C12 alpha methyl ester sulfonate, C16 alpha methyl ester sulfonate, and blends of C12-C16 alkyl ester sulfonates. A preferred alkyl ester sulfonate is sodium methyl-2 sulfo C12-C18 ester. Furthermore, alkyl ester sulfonates can be provided in compositions comprising other surfactants. For example, for many embodiments and formulations, a preferred commercially available component is ALPHA-STEP PC-48 (available from Stepan Co., Northfield, Ill.), which includes sodium methyl-2 sulfo C12-C18 ester and disodium 2-sulfo c12-c18 fatty acid.

Other suitable anionic surfactants that can be used are alkyl ester sulfonate surfactants including linear esters of $C_8$-$C_{20}$ carboxylic acids (i.e., fatty acids) which are sulfonated with gaseous $SO_3$ according to "The Journal of the American Oil Chemists Society", 52 (1975), pp. 323-329. Suitable starting materials would include natural fatty substances as derived from tallow, palm oil, etc.

Alkyl ester sulfonates also include fatty acid ester sulfonates, which are represented by the formula:

$$R^4CH(SO_3M)CO_2R^5$$

where $R^4$ is an alkyl group of 6 to 16 atoms, $R^5$ is an alkyl group of 1 to 4 carbon atoms and M is a solubilizing cation. The group $R^4$ may have a mixture of chain lengths. Preferably at least two-thirds of these groups have 6 to 12 carbon atoms. This will be the case when the moiety $R^4CH(\text{—})CO_2(\text{—})$ is derived from a coconut source, for instance. It is preferred that $R^5$ is a straight chain alkyl, notably methyl or ethyl.

In various embodiments of the present technology, the formulations can include one or more alkyl ester sulfonates in the amounts of from about 0.1% to about 90% by active weight; alternatively from about 2% to about 70% by active weight; alternatively from about 5% to about 45% by active weight; alternatively, from about 10% to about 30% by active weight based on the total weight of the composition. More particularly, formulations comprising one or more alkyl ester sulfonate in concentrations of at least about 0.1% by weight, alternatively at least about 0.2% by weight, alternatively at least about 0.5% by weight, alternatively at least about 1% by weight, alternatively at least about 2% by weight, alternatively at least about 4% by weight, alternatively at least about 5% by weight, alternatively at least about 10% by weight, are contemplated, as are formulations comprising at least about 0.1% by weight, alternatively at least about 0.2% by weight, alternatively at least about 0.5% by weight, alternatively at least about 1% by weight, alternatively at least about 2% by weight, alternatively at least about 5% by weight, are contemplated, as are concentrations of at most about 99.9% by weight, alternatively at most about 95% by weight, alternatively at most about 90% by weight, alternatively at most about 70% by weight, alternatively at most about 50% by weight, alternatively at most about 40% by weight, alternatively at most about 30% by weight, alternatively at most about 20% by weight. Any of the foregoing minimums and maximums can be combined to recite a range for the concentration of alkyl ester sulfonates in a formulation.

General Considerations for Heavy Duty Liquid (HDL) Laundry Detergents

Desirable surfactant attributes for HDLs include being in liquid form at room temperature, an ability to be formulated in cold-mix applications, and an ability to perform as well as or better than existing surfactants.

Desirable attributes for HDLs include, for example, the ability to emulsify, suspend or penetrate greasy or oily soils and suspend or disperse particulates, in order to clean surfaces; and then prevent the soils, grease, or particulates from re-depositing on the newly cleaned surfaces.

It is also desirable to have the ability to control the foaming—for use of an HDL in a high efficiency (it should be appreciated that high efficiency ("HE") washing machines include all front loading washing machines as well) washing machine, low foam is desired to achieve the best cleaning and to avoid excess foaming. Other desirable properties include the ability to clarify the formulation and to improve stability.

Formulation Viscosity

Formulations are contemplated having a viscosity of 5 cPs to 2000 cPs, measured at 25° C. using a Brookfield Viscometer model LV, spindle #2, speed 5 rpm. Certain SHP, PEHP, or EHP formulations have been found to have lower viscosity than comparable formulations lacking these surfactants, so these compositions function as viscosity reducers, which is very useful for making the contemplated highly concentrated, (e.g. greater than 40% surfactant active) detergent formulations.

Detergent Compositions

A wide variety of detergent compositions can be made that include SE, PHSE, HSE, SHP, PEHP, EHP, or combinations of two or more of these, as described in the present application, with or without other ingredients as specified below. Formulations are contemplated including 1% to 99% SE, PHSE, HSE, SHP, PEHP, and/or EHP, more preferably between 1% and 60%, even more preferably between 1% and 30%, with 99% to 1% water and, optionally, other ingredients as described here.

Additional Surfactants

The present compositions can contain additional surfactants, which can be anionic, cationic, nonionic, ampholytic, zwitterionic, or combinations of these.

Anionic Surfactants

In addition to SHP as an anionic surfactant used in the formulation, alkyl ester sulfonates and other anionic surfactants can be added. "Anionic surfactants" are defined here as amphiphilic molecules with an average molecular weight of less than about 10,000, comprising one or more functional groups that exhibit a net anionic charge when in aqueous solution at the normal wash pH, which can be a pH between 6 and 11. The anionic surfactant used in the present technology can be any anionic surfactant that is substantially water soluble. "Water soluble" surfactants are, unless otherwise noted, here defined to include surfactants which are soluble or dispersible to at least the extent of 0.01% by weight in distilled water at 25° C. It is preferred that at least one of the anionic surfactants used in the present technology be an alkali or alkaline earth metal salt of a natural or synthetic fatty acid containing between about 4 and about 30 carbon atoms. It is especially preferred to use a mixture of carboxylic acid salts with one or more other anionic surfactants. Another important class of anionic compounds is the water soluble salts, particularly the alkali metal salts, of organic sulfur reaction products having in their molecular structure an alkyl radical containing from about 6 to about 24 carbon atoms and a radical selected from the group consisting of sulfonic and sulfuric acid ester radicals.

Preferred additional surfactants for use in laundry detergent compositions include, for example, Steol CS-270 (lauryl 2-mole average ether sulfonate), Steol CS-170 (lauryl 1-mole average ether sulfonate), Steol CS-330 (lauryl 3-mole average ether sulfonate), Bio-Soft EC-690 (alcohol ethoxylate), Bio-Soft D-40 (sodium alkylbenzenesulfonate), Bio-Soft S-101 (alkylbenzene sulfonic acid) neutralized with sodium, potassium, ammonium and/or magnesium, Bio-Terge AS-40 (sodium olefin sulfonate), Alpha-Step PC-48 (alkyl methyl ester sulfonate) and/or Stepanol WA-Extra K (sodium lauryl sulfate), all from the Stepan Company, Northfield Ill. Any of the aforementioned anionic surfactants may be neutralized to form the sodium, potassium, ammonium or magnesium salts.

Specific types of anionic surfactants are identified in the following paragraphs. At least in some embodiments, alkyl ester sulfonates are preferred.

Carboxylic acid salts are represented by the formula:

R$^1$COOM where R$^1$ is a primary or secondary alkyl group of 4 to 30 carbon atoms and M is a solubilizing cation. The alkyl group represented by R$^1$ may represent a mixture of chain lengths and may be saturated or unsaturated, although it is preferred that at least two thirds of the R$^1$ groups have a chain length of between 8 and 18 carbon atoms. Non-limiting examples of suitable alkyl group sources include the fatty acids derived from coconut oil, tallow, tall oil and palm kernel oil. For the purposes of minimizing odor, however, it is often desirable to use primarily saturated carboxylic acids. Such materials are well known to those skilled in the art, and are available from many commercial sources, such as Uniqema (Wilmington, Del.) and Twin Rivers Technologies (Quincy, Mass.). The solubilizing cation, M, may be any cation that confers water solubility to the product, although monovalent such moieties are generally preferred. Examples of acceptable solubilizing cations for use with the present technology include alkali metals such as sodium and potassium, which are particularly preferred, and amines such as triethanolammonium, ammonium and morpholinium. Although, when used, the majority of the fatty acid should be incorporated into the formulation in neutralized salt form, it is often preferable to leave a small amount of free fatty acid in the formulation, as this can aid in the maintenance of product viscosity.

Primary alkyl sulfates are represented by the formula:

R$^2$OSO$_3$M where R$^2$ is a primary alkyl group of 8 to 18 carbon atoms. M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like). The alkyl group $R^2$ may have a mixture of chain lengths. It is preferred that at least two-thirds of the $R^2$ alkyl groups have a chain length of 8 to 14 carbon atoms. This will be the case if $R^2$ is coconut alkyl, for example. The solubilizing cation may be a range of cations which are in general monovalent and confer water solubility. An alkali metal, notably sodium, is especially envisaged. Other possibilities are ammonium and substituted ammonium ions, such as trialkanolammonium or trialkylammonium.

Alkyl ether sulfates are represented by the formula:

$$R^3O(CH_2CH_2O)_nSO_3M$$

where $R^3$ is a primary alkyl group of 8 to 18 carbon atoms, n has an average value in the range from 1 to 6 and M is a solubilizing cation. The alkyl group $R^3$ may have a mixture of chain lengths. It is preferred that at least two-thirds of the $R^3$ alkyl groups have a chain length of 8 to 14 carbon atoms. This will be the case if $R^3$ is coconut alkyl, for example. Preferably n has an average value of 2 to 5. Ether sulfates have been found to provide viscosity build in certain of the formulations of the present technology, and thus are considered a preferred ingredient.

Alkyl benzene sulfonates are represented by the formula:

$$R^6ArSO_3M$$

where $R^6$ is an alkyl group of 8 to 18 carbon atoms, Ar is a benzene ring ($—C_6H_4—$) and M is a solubilizing cation. The group $R^6$ may be a mixture of chain lengths. A mixture of isomers is typically used, and a number of different grades, such as "high 2-phenyl" and "low 2-phenyl" are commercially available for use depending on formulation needs. A plentitude of commercial suppliers exist for these materials, including Stepan Company (Northfield, Ill.) and Witco (Greenwich, Conn.) Typically they are produced by the sulfonation of alkylbenzenes, which can be produced by either the HF-catalyzed alkylation of benzene with olefins or an $AlCl_3$-catalyzed process that alkylates benzene with chloroparaffins, and are sold by, for example, Petresa (Chicago, Ill.) and Sasol (Austin, Tex.). Straight chains of 11 to 14 carbon atoms are usually preferred.

Paraffin sulfonates having about 8 to about 22 carbon atoms, preferably about 12 to about 16 carbon atoms, in the alkyl moiety, are contemplated for use here. They are usually produced by the sulfoxidation of petrochemically-derived normal paraffins. These surfactants are commercially available as, for example, Hostapur SAS from Clariant (Charlotte, N.C.).

Olefin sulfonates having 8 to 22 carbon atoms, preferably 12 to 16 carbon atoms, are also contemplated for use in the present compositions. The olefin sulfonates are further characterized as having from 0 to 1 ethylenic double bonds; from 1 to 2 sulfonate moieties, of which one is a terminal group and the other is not; and 0 to 1 secondary hydroxyl moieties. U.S. Pat. No. 3,332,880 contains a description of suitable olefin sulfonates, and is incorporated here by reference. Examples of specific surfactant species from that patent include the following:

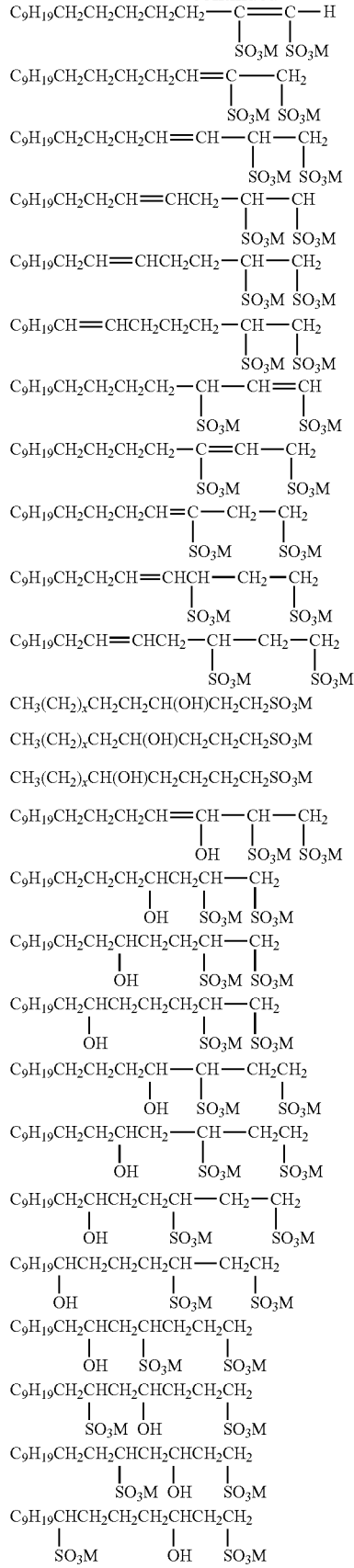

In the preceding formulas, x is an integer of from about 4 to about 18, preferably from about 4 to about 12, and M represents any cation that forms a water-soluble salt such as alkali metals, e.g., sodium and potassium, and ammonium and substituted ammonium compounds, e.g., trialkylammonium and trialkylolammonium compounds. Specific examples of substituted ammonium compounds are triethylammonium, trimethylammonium, and triethanolammonium. Others will be apparent to those skilled in the art. Such materials are sold as, for example, Bio-Terge AS-40, which can be purchased from Stepan (Northfield, Ill.)

Sulfosuccinate esters represented by the formula:

are also useful in the context of the present technology. $R^7$ and $R^8$ are alkyl groups with chain lengths of between 2 and 16 carbons, and may be linear or branched, saturated or unsaturated. A preferred sulfosuccinate is sodium bis(2-ethylhexyl) sulfosuccinate, which is commercially available under the trade name Aerosol OT from Cytec Industries (West Paterson, N.J.).

Organic phosphate based anionic surfactants include organic phosphate esters such as complex mono- or diester phosphates of hydroxyl-terminated alkoxide condensates, or salts thereof. Included in the organic phosphate esters are phosphate ester derivatives of polyoxyalkylated alkylaryl phosphate esters, of ethoxylated linear alcohols and ethoxylates of phenol. Also included are nonionic alkoxylates having a sodium alkylenecarboxylate moiety linked to a terminal hydroxyl group of the nonionic through an ether bond. Counterions to the salts of all the foregoing may be those of alkali metal, alkaline earth metal, ammonium, alkanolammonium and alkylammonium types.

Fatty acid ester sulfonates are represented by the formula:

where the moiety $R^9CH(-)CO_2(-)$ is derived from a coconut source and $R^{10}$ is either methyl or ethyl.

Another class of preferred anionic surfactants contemplated for the present purposes is the alkyl alkoxylated sulfate surfactants which are water soluble salts or acids of the formula $RO(A)_mSO_3M$ where R is an unsubstituted $C_{10}$-$C_{24}$ alkyl or hydroxyalkyl group having a $C_{10}$-$C_{24}$ alkyl component, preferably a $C_{12}$-$C_{18}$ alkyl or hydroxyalkyl, more preferably $C_{12}$-$C_{15}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated here. Specific examples of substituted ammonium cations include ethanol-, triethanol-, methyl-, dimethyl-, or trimethylammonium cations and quaternary ammonium cations such as tetramethyl-ammonium and dimethyl piperidinium cations and those derived from alkylamines such as ethylamine, diethylamine, triethylamine, mixtures thereof and the like. Exemplary surfactants are $C_{12}$-$C_{15}$ alkyl polyethoxylate (1.0) sulfate ($C_{12}$-$C_{15}$ E(1.0)M), $C_{12}$-$C_{15}$ alkyl polyethoxylate (2.25) sulfate ($C_{12}$-$C_{15}$ E(2.25) M), $C_{12}$-$C_{15}$ alkyl polyethoxylate (3.0) sulfate ($C_{12}$-$C_{15}$ E(3.0)M), and $C_{12}$-$C_{15}$ alkyl polyethoxylate (4.0) sulfate ($C_{12}$-$C_{15}$ E(4.0)M), where M is conveniently selected from sodium and potassium.

Other anionic surfactants useful for detersive purposes can also be included in the present compositions, including detergent compositions of the present technology. These can include salts (including, for example, sodium, potassium, ammonium, and substituted ammonium salts such as mono-, di- and triethanolamine salts) of soap, $C_8$-$C_{22}$ primary of secondary alkanesulfonates, $C_8$-$C_{24}$ olefin sulfonates, sulfonated polycarboxylic acids prepared by sulfonation of the pyrolyzed product of alkaline earth metal citrates, e.g., as described in British patent specification No. 1,082,179, $C_8$-$C_{24}$ alkypolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$-$C_{18}$ monoesters) and diesters of sulfosuccinates (especially saturated and unsaturated $C_6$-$C_{12}$ diesters), sulfates of alkylpolysaccharides such as the sulfates of alkylpolyglucoside (the nonionic non-sulfated compounds being described below), and alkyl polyethoxy carboxylates such as those of the formula $RO(CH_2CH_2O)_kCH_2COO$-M+ where R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (incorporated here by reference), and Unilever U.S. Pat. No. 6,949,498 column 6, line 4 through column 8, line 30 (incorporated here by reference), from which much of the present discussion comes.

Other anionic surfactants contemplated for use with the present formulations include isethionates, sulfated triglycerides, alcohol sulfates, ligninsulfonates, naphthelene sulfonates and alkyl naphthelene sulfonates and the like. Additional anionic surfactants, falling into the general definition but not specifically mentioned above, should also be considered within the scope of the present technology.

Specific anionic surfactants contemplated for use in the present compositions include alcohol ether sulfates (AES), linear alkylbenzene sulfonates (LAS), alcohol sulfates (AS), alpha methyl ester sulfonates (MES) and other alkyl ester sulfonates, or combinations of two or more of these. The amount of anionic surfactant contemplated can be, for example, 1% to 70% of the composition more preferably between 1% and 60%, even more preferably between 1% and 40%. For a more general description of surfactants, see P&G U.S. Pat. No. 5,929,022; column 3, 2nd paragraph through column 4, end of 1st paragraph (incorporated here by reference), from which much of the present discussion comes.

Cationic Surfactants

Specific cationic surfactants contemplated for use in the present compositions include ditallow dimethylammonium chloride (DTDMAC), fatty alkanolamides (FAA), and quaternized diesters of trialkanolamines and fatty acids. The proportions of cationic surfactants used in a formulation can range, for example, from 0.1% to 20%, more preferably between 1% and 10%, even more preferably between 1% and 5%. See also P&G U.S. Pat. No. 5,929,022; column 6, 2nd paragraph through column 7, 1st paragraph, from which much of the following discussion comes:

Cationic detersive surfactants suitable for use in the present compositions, particularly laundry detergent compositions of the present technology, include those having one long-chain hydrocarbyl group. Examples of such cationic surfactants include the ammonium surfactants such as alkyldimethylammonium halogenides, and those surfactants having the formula:

$$[R^2(OR^3)_y][R^4(OR^3)_y]_2R^5N^+X^-$$

where $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, —$CH_2CHOH$—$CH(OH)C(O)R^6CH(OH)CH_2OH$ where $R^6$ is any hexose or hexose polymer having a molecular weight less than about 1000, and hydrogen when y is not 0; $R^5$ is the same as $R^4$ or is an alkyl chain where the total number of carbon atoms of $R^2$ plus $R^5$ is not more than about 18; each y is from 0 to about 10 and the sum of the y values is from 0 to about 15; and X is any compatible anion. The long chain cationic surfactant can also be the quaternized version of stearamidopropyl dimethylamine (e.g. stearamidopropyl trimethylamine chloride).

Preferred cationic surfactants are the water-soluble quaternary ammonium compounds useful in the present composition having the formula:

$$R^1R^2R^3R^4N^+X^-$$

where $R^1$ is $C_8$-$C_{16}$ alkyl, each of $R^2$, $R^3$ and $R^4$ is independently $C_1$-$C_4$ alkyl, $C_1$-$C_4$ hydroxyalkyl, benzyl, or —$(C_2H_4O)_xH$ where x has a value from 1 to 5, and X is an anion. In an embodiment, not more than one of $R^2$, $R^3$ or $R^4$ is benzyl.

The preferred alkyl chain length for $R^1$ is $C_{12}$-$C_{15}$, particularly where the alkyl group is a mixture of chain lengths derived from coconut or palm kernel fat or is derived synthetically by olefin build up or OXO alcohols synthesis. Preferred groups for $R^2$, $R^3$, and $R^4$ are methyl and hydroxyethyl groups and the anion X may be selected from halide, methosulphate, acetate and phosphate ions.

Examples of suitable quaternary ammonium compounds for use here are:
 hexadecyl trimethyl ammonium chloride, also known as cetrimonium chloride, sold commercially as Ammonyx® CETAC by Stepan Co.;
 coconut trimethyl ammonium chloride or bromide;
 coconut methyl dihydroxyethyl ammonium chloride or bromide;
 decyl triethyl ammonium chloride;
 decyl dimethyl hydroxyethyl ammonium chloride or bromide;
 $C_{12-15}$ dimethyl hydroxyethyl ammonium chloride or bromide;
 coconut dimethyl hydroxyethyl ammonium chloride or bromide;
 myristyl trimethyl ammonium methyl sulphate;
 lauryl dimethyl benzyl ammonium chloride or bromide;
 lauryl dimethyl(ethenoxy)4 ammonium chloride or bromide;
 choline esters of formula $$R^1R^2R^3R^4N^+X^-$$

where $R^1$ is —$CH_2$—O—$C(O)$—$(C_{12-14}$ alkyl) and $R^2$, $R^3$, and $R^4$ are methyl; and combinations of these.

Other cationic surfactants useful here are also described in U.S. Pat. No. 4,228,044, Cambre, issued Oct. 14, 1980, incorporated herein by reference.

Nonionic Surfactants

Examples of suitable nonionic surfactants include alkyl polyglucosides ("APGs"), alcohol ethoxylates, nonylphenol ethoxylates, and others. The nonionic surfactant may be used as from 1% to 90%, more preferably from 1 to 40% and most preferably between 1% and 32% of a detergent composition. Other suitable nonionic surfactants are described in P&G U.S. Pat. No. 5,929,022; column 4, 2nd paragraph through column 6, end of 1st paragraph, from which much of the following discussion comes:

One class of nonionic surfactants useful in the practice of the present technology are condensates of ethylene oxide with a hydrophobic moiety to provide a surfactant having an average hydrophilic-lipophilic balance (HLB) in the range from 8 to 17, preferably from 9.5 to 14, more preferably from 12 to 14. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

For "low HLB" nonionics, low HLB can be defined as having an HLB of 8 or less and preferably 6 or less. a "low level" of co-surfactant can be defined as 6% or less of the HDL and preferably 4% or less of the HDL.

Especially preferred nonionic surfactants of this type are the $C_9$-$C_{15}$ primary alcohol ethoxylates containing 3-12 moles of ethylene oxide per mole of alcohol, particularly the $C_{12}$-$C_{15}$ primary alcohols containing 5-8 moles of ethylene oxide per mole of alcohol. One suitable example of such a surfactant is polyalkoxylated aliphatic base, sold for example as Makon® NF-12 by Stepan Co.

Another class of nonionic surfactants comprises alkyl polyglucoside compounds of general formula $$RO—(C_nH_{2n}O)_tZ_x$$

where Z is a moiety derived from glucose; R is a saturated hydrophobic alkyl group that contains from 12 to 18 carbon atoms; t is from 0 to 10 and n is 2 or 3; x is an average value from 1.3 to 4, the compounds including less than 10% unreacted fatty alcohol and less than 50% short chain alkyl polyglucosides. Compounds of this type and their use in detergent compositions are disclosed in EP-B 0 070 077, EP 0 075 996 and EP 0 094 118.

Very suitable as nonionic surfactants are poly hydroxy fatty acid amide surfactants of the formula $$R^2—C(O)—N(R^1)—Z$$

where $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or alkenyl chain such as coconut alkyl or mixtures thereof, and Z is derived from a reducing sugar such as glucose, fructose, maltose, lactose, in a reductive amination reaction.

Highly preferred nonionics are amine oxide surfactants. The compositions of the present technology may comprise amine oxide in accordance with the general formula:

$$R^1(EO)_x(PO)_y(BO)_zN(O)(CH_2R')_2.H_2O$$

In general, it can be seen that the preceding formula provides one long-chain moiety $R^1(EO)_x(PO)_y(BO)_z$ and two short chain moieties, —$CH_2R'$. R' is preferably selected from hydrogen, methyl and —$CH_2OH$. In general $R^1$ is a primary or branched hydrocarbyl moiety which can be saturated or unsaturated, preferably, $R^1$ is a primary alkyl moiety. When $x+y+z=0$, $R^1$ is a hydrocarbyl moiety having a chain length of from about 8 to about 18. When $x+y+z$ is different from 0, $R^1$ may be somewhat longer, having a chain length in the range $C_{12}$-$C_{24}$. The general formula also encompasses amine oxides where $x+y+z=0$, $R^1$ is $C_8$-$C_{18}$, R' is H and q=from 0 to 2, preferably 2. These amine oxides are illustrated by $C_{12-14}$ alkyldimethyl amine oxide, hexadecyl dimethylamine oxide, octadcylamine oxide and their hydrates, especially the dihydrates as disclosed in U.S. Pat. Nos. 5,075,501 and 5,071,594, which are incorporated herein by reference.

The presently described technology also encompasses amine oxides where $x+y+z$ is different from zero, specifically $x+y+z$ is from about 1 to about 10, and $R^1$ is a primary alkyl group containing about 8 to about 24 carbons, preferably from about 12 to about 16 carbon atoms. In these embodiments $y+z$ is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

Highly preferred amine oxides here are solids at ambient temperature, more preferably they have melting-points in the range 30° C. to 90° C. Amine oxides suitable for use here are made commercially by a number of suppliers, including Akzo Chemie, Ethyl Corp., and Procter & Gamble. See McCutcheon's compilation and Kirk-Othmer review article for alternate amine oxide manufacturers. Preferred commercially available amine oxides are the solid, dihydrate ADMOX 16 and ADMOX 18, ADMOX 12 and especially ADMOX 14 from Ethyl Corp.

Preferred embodiments include, for example, hexadecyldimethylamine oxide dihydrate, octa-decyldimethylamine oxide dihydrate, hexadecyltris(ethyleneoxy)dimethylamine oxide, and tetradecyldimethyl amine oxide dihydrate.

In certain of the preferred embodiments in which R' is H, there is some latitude with respect to having R' slightly larger than H. Specifically, the presently described technology further encompasses embodiments where R'=$CH_2OH$, such as hexadecylbis(2-hydroxyethyl)amine oxide, tallowbis(2-hydroxyethyl)amine oxide, stearylbis(2-hydroxyethyl)amine oxide and oleylbis(2-hydroxyethyl)amine oxide.

Ampholytic Surfactants

Ampholytic synthetic detergents can be broadly described as derivatives of aliphatic or aliphatic derivatives of heterocyclic secondary and tertiary amines, in which the aliphatic radical may be straight chain or branched and where one of the aliphatic substituents contains from about 8 to about 18 carbon atoms and at least one contains an anionic water-solubilizing group, e.g., carboxy, sulfo, sulfato, phosphato, or phosphono (see U.S. Pat. No. 3,664,961, which provides specific examples of ampholytic surfactants from col. 6, line 60, to col. 7, line 53, incorporated here by reference). Examples of suitable ampholytic surfactants include fatty amine oxides and fatty amidopropylamine oxides. A specific suitable example is cocoamidopropyl betaine (CAPB) also known as coco betaine. Ampholytic surfactants can be used at a level from 1% to 50%, more preferably from 1% to 10%, even more preferably between 1% and 5% of the formulation, by weight.

Zwitterionic Surfactants

Zwitterionic synthetic detergents can be broadly described as derivatives of aliphatic quaternary ammonium and phosphonium or tertiary sulfonium compounds, in which the cationic atom may be part of a heterocyclic ring, and in which the aliphatic radical may be straight chain or branched, and where one of the aliphatic substituents contains from about 3 to 18 carbon atoms, and at least one aliphatic substituent contains an anionic water-solubilizing group, e.g., carboxy, sulfo, sulfato, phosphato, or phosphono. (see U.S. Pat. No. 3,664,961, which provides specific examples of zwitterionic surfactants from col. 7, line 65, to col. 8, line 75, incorporated here by reference). Zwitterionic surfactants can be used as from 1% to 50%, more preferably from 1% to 10%, even more preferably from 1% to 5% by weight of the present formulations.

Foam Stabilizing Surfactants

Certain embodiments of the present technology, including but not limited to LDL detergent formulations, can contain foam stabilizing surfactants in amounts of from about 0.5% to about 15% by active weight; alternatively, from about 3% to about 10% by active weight; alternatively about 5% by active weight based on the total actives ingredient weight of the composition.

Preferred foam stabilizing surfactants of the present technology can include Amphosol CA (cocoamidopropyl betaine), Ammonyx LMDO (lauryl myristal amidopropyl dimethyl amine oxide), Ammonyx LO (lauryl dimethyl amine oxide) all from the Stepan Company, Northfield Ill., as well as Glucopon 600 (alkyl polyglucoside), and Glucopon 425 N (alkyl polyglucoside), both from the Cognis Company, Monheim Germany.

Mixtures of Surfactants

Mixtures of any two or more individually contemplated surfactants, whether of the same type or different types, are contemplated herein.

Laundry Detergent Composition

The formulation and use of the present surfactants will now be illustrated in more detail for a laundry detergent composition.

Four desirable characteristics of a laundry detergent composition, in particular a liquid composition (although the present disclosure is not limited to a liquid composition, or to a composition having any or all of these attributes) are that (1) a concentrated formulation is useful to save on shelf space of a retailer, (2) a "green" or environmentally friendly composition is useful, (3) a composition that works in modern high efficiency washing machines which use less energy and less water to wash clothes than previous machines is useful, and (4) a composition that cleans well in lower temperature water for example less than 70° F.

To save a substantial amount of retailer shelf space, a concentrated formulation is contemplated having two or even three four, five, six, or even greater (e.g., 8×) times potency per unit volume or dose as conventional laundry detergents. The use of less water complicates the formulation of a detergent composition, as it needs to be more soluble and otherwise to work well when diluted in relatively little water.

To make a "green" formula, the surfactants should be ultimately biodegradable and non-toxic. To meet consumer perceptions and reduce the use of petrochemicals, a "green" formula may also advantageously be limited to the use of renewable hydrocarbons, such as vegetable or animal fats and oils, in the manufacture of surfactants.

High efficiency (HE) washing machines present several challenges to the detergent formulation. As of January 2011, all washing machines sold in the US must be HE, at least to some extent, and this requirement will only become more restrictive in the coming years. Front loading machines, all of which are HE machines, represent the highest efficiency, are increasingly being used.

Heavy duty liquid (HDL) detergent formulas are impacted by HE machines because the significantly lower water usage requires that less foam be generated during the wash cycle. As the water usage levels continue to decrease in future generations of HE machines, detergents may be required to transition to no foam. In addition, HE HDLs should also disperse quickly and cleanly at lower wash temperatures.

To work in a modern high efficiency washing machine, the detergent composition needs to work in relatively concentrated form in cold water, as these washing machines use relatively little water and cooler washing temperatures than prior machines. The sudsing of such high-efficiency formulations must also be reduced, or even eliminated, in a low-water environment to provide effective cleaning performance. The anti-redeposition properties of a high efficiency detergent formulation also must be robust in a low-water environment. In addition, formulations that allow the used wash water to be more easily rinsed out of the clothes or spun out of the clothes in a washing machine are also contemplated, to promote efficiency.

Liquid fabric softener formulations and "softergent" (fabric softener/detergent dual functional) single-add formulations also may need to change as water usage continues to decline in HE machines. A washer-added softener is dispensed during the rinse cycle in these machines. The present SE, PHSE, and HSE compositions provide some softening activity, which is contemplated to address these problems.

Laundry detergents and additives containing the presently described SE, PHSE, and HSE compositions are contemplated to provide high concentration formulations, or "green" formulations, or formulations that work well in high efficiency washing machines. Such detergents and additives are contemplated that have at least one of the advantages or desirable characteristics specified above, or combinations of two or more of these advantages, at least to some degree. The ingredients contemplated for use in such laundry detergents and additives are found in the following paragraphs.

In addition to the surfactants as previously described, a laundry detergent composition commonly contains other ingredients for various purposes. Some of those ingredients are also described below.

Builders and Alkaline Agents

Builders and other alkaline agents are contemplated for use in the present formulations.

Any conventional builder system is suitable for use here, including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylene-phosphonic acid. Though less preferred for obvious environmental reasons, phosphate builders could also be used here.

Suitable polycarboxylate builders for use here include citric acid, preferably in the form of a water-soluble salt, and derivatives of succinic acid of the formula:

R—CH(COOH)CH$_2$(COOH)

where R is $C_{10-20}$ alkyl or alkenyl, preferably $C_{12-16}$, or where R can be substituted with hydroxyl, sulfo sulfoxyl or sulfone substituents. Specific examples include lauryl succinate, myristyl succinate, palmityl succinate 2-dodecenylsuccinate, or 2-tetradecenyl succinate. Succinate builders are preferably used in the form of their water-soluble salts, including sodium, potassium, ammonium and alkanolammonium salts. Other builders contain sodium citrate dihydrate, monoethanolamine, and triethanolamine. Other suitable polycarboxylates are oxodisuccinates and mixtures of tartrate monosuccinic and tartrate disuccinic acid, as described in U.S. Pat. No. 4,663,071.

Especially for a liquid detergent composition, suitable fatty acid builders for use here are saturated or unsaturated $C_{10-18}$ fatty acids, as well as the corresponding soaps. Preferred saturated species have from 12 to 16 carbon atoms in the alkyl chain. The preferred unsaturated fatty acid is oleic acid. Another preferred builder system for liquid compositions is based on dodecenyl succinic acid and citric acid.

Some examples of alkaline agents include alkalic metal (Na, U, or NH$_4$) hydroxides, carbonates, bicarbonates. Another commonly used builder is borax.

For powdered detergent compositions, the builder or alkaline agent typically comprises from 1% to 95% of the composition. For liquid compositions, the builder or alkaline agent typically comprises from 1% to 60%, alternatively between 1% and 30%, alternatively between 2% and 15%. See U.S. Pat. No. 5,929,022; column 7, start of 2nd paragraph through column 7, end of 6th paragraph, from which much of the preceding discussion comes. Other builders are described in PCT Publ. WO 99/05242, which is incorporated here by reference.

Enzymes

The sulfonated estolide formulations of the present technology may further comprise one or more enzymes, which provide cleaning performance and/or fabric care benefits. Suitable enzymes may be selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases or mixtures thereof.

A preferred combination is a detergent composition having a cocktail of conventional applicable enzymes like protease, amylase, lipase, cutinase and/or cellulase in conjunction with the lipolytic enzyme variant D96L at a level of from 50 LU to 8500 LU per liter wash solution.

The cellulases usable in the present technology include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from Humicola insolens. Suitable cellulases are also disclosed in GB-A-2 075 028; GB-A-2 095 275 and DE-OS-2 247 832, which are incorporated herein by reference.

Examples of such cellulases are cellulases produced by a strain of Humicola insolens (Humicola grisea var. thermoidea), particularly the Humicola strain DSM 1800. Other suitable cellulases are cellulases originated from Humicola insolens having a molecular weight of about 50 KDa, an isoelectric point of 5.5 and containing 415 amino acids. Especially suitable cellulases are the cellulases having color care benefits. Examples of such cellulases are cellulases described in European patent application No. 91202879.2, filed Nov. 6, 1991 (Novo).

Peroxidase enzymes are used in combination with oxygen sources, e.g. percarbonate, perborate, persulfate, hydrogen peroxide, etc. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991.

Said cellulases and/or peroxidases are normally incorporated in the detergent composition at levels from 0.0001% to 2% of active enzyme by weight of the detergent composition.

Preferred commercially available protease enzymes include those sold under the tradenames Alcalase®, Savinase®, Primase®, Durazym®, and Esperase® by Novo Nordisk A/S (Denmark), those sold under the tradename Maxatase®, Maxacal® and Maxapem® by Gist-Brocades, those sold by Genencor International, and those sold under the tradename Opticlean® and Optimase® by Solvay Enzymes. Other proteases are described in U.S. Pat. No. 5,679,630, issued Oct. 21, 1997 (P&G) can be included in the detergent composition of the present technology. Protease enzyme may be incorporated into the compositions in accordance with the present technology at a level of from about 0.0001% to about 2% active enzyme by weight of the composition.

A preferred protease here referred to as "Protease D" is a carbonyl hydrolase variant having an amino acid sequence not found in nature, which is derived from a precursor carbonyl hydrolase by substituting a different amino acid for the amino acid residue at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in U.S. Pat. No. 5,679,630, issued Oct. 21, 1997, which is incorporated here by reference in its entirety.

Highly preferred enzymes that can be included in the detergent compositions of the present technology include lipases. It has been found that the cleaning performance on greasy soils is synergistically improved by using lipases. Suitable lipase enzymes include those produced by microorganisms of the *Pseudomonas* group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas fluorescens* IAM 1057. This lipase is available from Amano Pharmaceutical Co. Ltd., Nagoya, Japan, under the trade name Lipase P "Amano," hereafter referred to as "Amano-P". Further suitable lipases are lipases such as M1 Lipase®. and Lipomax®. (Gist-Brocades). Highly preferred lipases are the D96L lipolytic enzyme variant of the native lipase derived from *Humicola lanuginosa* as described in U.S. Pat. No. 6,017,871 issued Jan. 25, 2000 (P&G). Preferably the *Humicola lanuginosa* strain DSM 4106 is used. This enzyme is incorporated into the composition in accordance with the present technology at a level of from 50 LU to 8500 LU per liter wash solution. Preferably the variant D96L is present at a level of from 100 LU to 7500 LU per liter of wash solution. More preferably at a level of from 150 LU to 5000 LU per liter of wash solution.

By D96L lipolytic enzyme variant is meant the lipase variant as described in patent application WO 92/05249 viz. where the native lipase ex *Humicola lanuginosa* aspartic acid (D) residue at position 96 is changed to Leucine (L). According to this nomenclature said substitution of aspartic acid to Leucine in position 96 is shown as: D96L.

Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor).

The lipases and/or cutinases are normally incorporated in the detergent composition at levels from 0.0001% to 2% of active enzyme by weight of the detergent composition.

Amylases (α and/or β) can be included for removal of carbohydrate-based stains. Suitable amylases are Termamyl® (Novo Nordisk), Fungamyl® and BAN° (Novo Nordisk).

The above-mentioned enzymes may be of any suitable origin, such as vegetable, animal, bacterial, fungal and/or yeast origin. See U.S. Pat. No. 5,929,022; column 7, 7th paragraph through column 9, 6th paragraph, from which much of the preceding discussion comes. Preferred compositions optionally contain a combination of enzymes or a single enzyme, with the amount of each enzyme commonly ranging from 0.0001% to 2%.

Other enzymes and materials used with enzymes are described in PCT Publ. WO99/05242, which is incorporated here by reference.

Enzymes are expected to exhibit excellent shelf-life in SHP-containing HDLs. Not to be bound by theory, surfactants with low CMC values tend to be more mild to enzymes based on low monomer concentrations in solution which interfere with enzyme stability. The measured CMC, via the Wilhelmy plate technique, of SHP is 30 mg/L while that of the sodium salt of AES is 80 mg/L and NaLAS is 900 mg/L.

Adjuvants

The sulfonated estolide formulations of the present technology optionally contain one or more soil suspending agents or resoiling inhibitors in an amount from about 0.01% to about 5% by weight, alternatively less than about 2% by weight. Resoiling inhibitors include anti-redeposition agents, soil release agents, or combinations thereof. Examples of suitable agents are described in U.S. Pat. No. 5,929,022; column 10, 3rd paragraph through column 10, 5th paragraph, and include water-soluble ethoxylated amines having clay soil removal and anti-redeposition properties. Examples of such soil release and anti-redeposition agents given in the referenced patent include an ethoxylated tetraethylenepentamine. The ethoxylated amines further described in U.S. Pat. No. 4,597,898, VanderMeer, issued Jul. 1, 1986, are incorporated here by reference. Another group of preferred clay soil removal/anti-redeposition agents are the cationic compounds disclosed in European Patent Application 111,965, Oh and Gosselink, published Jun. 27, 1984, incorporated here by reference. Other clay soil removal/anti-redeposition agents which can be used include the ethoxylated amine polymers disclosed in European Patent Application 111,984, Gosselink published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985, all of which are incorporated here by reference.

Other clay soil removal and/or anti-redeposition agents known in the art can also be utilized in the compositions hereof. Another type of preferred anti-redeposition agent includes the carboxymethylcellulose (CMC) materials.

For example, optionally, anti-redeposition polymers can be incorporated into laundry detergent formulations covered by the presently described technologies. In at least some embodiment, it is preferred to keep the level of anti-redeposition polymer below about 2%. It has been found that at levels above about 2%, anti-redeposition polymer may cause formulation instability (e.g. phase separation) and or undue thickening.

Soil release agents are also contemplated as optional ingredients in the amount of about 0.1% to about 5%. See U.S. Pat. No. 5,929,022; column 9, 8th paragraph through column 10, end of 1st partial paragraph.

Chelating agents in the amounts of about 0.1% to about 10%, more preferably about 0.5% to about 5% and even more preferably from about 0.8% to about 3% are also contemplated as an optional ingredient. See U.S. Pat. No. 5,929,022; column 10, 1st paragraph to column 10, end of 2nd paragraph.

Polymeric dispersing agents in the amount of 0% to about 6% are also contemplated as an optional component of the presently described detergent compositions. See U.S. Pat. No. 5,929,022; column 10, start of 7th paragraph to column 10, end of the continuing paragraph from that started on the previous column and is incorporated herein by reference.

A suds suppressor is also contemplated as an optional component of the present detergent composition, in the amount of from about 0.1% to about 15%, more preferably between about 0.5% to about 10% and even more preferably between about 1% to about 7%. See U.S. Pat. No. 5,929,022 column 11. The SE, PHSE, and HSE compositions described in this specification can also function as suds suppressants, alone or in combination with other suds suppressants.

Other ingredients that can be included in a liquid laundry detergent include perfumes that optionally contain ingredients such as aldehydes, ketones, esters, and alcohols. More compositions that can be included are: carriers, hydrotropes, processing aids, dyes, pigments, solvents, bleaches, bleach activators and enzyme stabilizing packaging systems.

The co-surfactant technology of U.S. Pat. No. 4,561,998 can be used in conjunction with the present technology, for the reasons explained in that patent that is incorporated herein by reference. Co-surfactants and fatty acids identified in U.S. Pat. No. 4,561,998 that can be used in conjunction with anionic surfactants to improve laundering performance include, for example, chloride, bromide and methylsulfate $C_{8-16}$ alkyl trimethylammonium salts, $C_{8-16}$ alkyl di(hydroxyethyl)methylammonium salts, $C_{8-16}$ alkyl hydroxyethyldimethylammonium salts, and $C_{8-16}$ alkyloxypropyl trimethylammonium salts.

Similar to what is taught in U.S. Pat. No. 4,561,998, the compositions herein can also contain from about 0.25% to about 12%, preferably from about 0.5% to about 8%, more preferably from about 1% to about 4%, by weight of a cosurfactant selected from the group of certain quaternary ammonium, diquaternary ammonium, amine, diamine, amine oxide and di(amine oxide) surfactants. The quaternary ammonium surfactants are particularly preferred.

Additional information regarding co-surfactants that may be compatible with the currently presented technology can be found in U.S. application Ser. No. 12/353,751, which is hereby incorporated by reference.

Other common cleaning adjuncts are identified in U.S. Pat. No. 7,326,675, col. 12, and PCT Publ. WO 99/05242 (Pages 29-56). Such cleaning adjuncts are identified as including bleaches, bleach activators, suds boosters, dispersant polymers (e.g., from BASF Corp. or Rohm & Haas) other than those described above, color speckles, silvercare, anti-tarnish and/or anti-corrosion agents, pigments, dyes, fillers, germicides, hydrotropes, anti-oxidants, enzyme stabilizing agents, pro-perfumes, carriers, processing aids, solvents, dye transfer inhibiting agents, brighteners, structure elasticizing agents, fabric softeners, anti-abrasion agents, and other fabric care agents, surface and skin care agents. Suitable examples of such other cleaning adjuncts and levels of use are found in U.S. Pat. Nos. 5,576,282, 6,306,812 B1 and 6,326,348 B1 and PCT Publ. WO99/05242. All the patents identified in this paragraph are incorporated by reference for their further disclosures of adjuvants.

Fatty Acid

Similar to that disclosed in U.S. Pat. No. 4,561,998, the compositions of the present technology may contain from about 5% to about 40%, preferably from about 7% to about 30%, most preferably from about 10% to about 20%, by weight of a fatty acid containing from about 10 to about 22 carbon atoms. The fatty acid can also contain from about 1 to about 10 ethylene oxide units in the hydrocarbon chain.

Suitable fatty acids are saturated and/or unsaturated and can be obtained from natural sources such as plant or animal esters (e.g., palm kernel oil, palm oil, coconut oil, babassu oil, safflower oil, tall oil, castor oil, tallow and fish oils, grease, and mixtures thereof) or synthetically prepared (e.g., via the oxidation of petroleum or by hydrogenation of carbon monooxide via the Fisher-Tropsch process). Examples of suitable saturated fatty acids for use in the compositions of the present technology include, but are not limited to capric, lauric, myristic, palmitic, stearic, arachidic and behenic acid. Suitable unsaturated fatty acid species include: palmitoleic, oleic, linoleic, linolenic and ricinoleic acid. Examples of preferred fatty acids are saturated $C_{10}$-$C_{14}$ (coconut) fatty acids, from about 5:1 to about 1:1 (preferably about 3:1) weight ratio mixtures of lauric and myristic acid, and mixtures of the above lauric/myristic blends with oleic acid at a weight ratio of about 4:1 to about 1:4 mixed lauric/myristic:oleic.

A preferred fatty acid that may be used with magnesium ion containing sulfonated estolide HDL compositions of the present technology is the fatty alcohol ethoxylate, BIO-SOFT® N25-7 ($C_{12-15}EO_7$), which can be purchased from Stepan Company (Northfield, Ill.).

U.S. Pat. No. 4,507,219 identifies various sulfonate surfactants as suitable for use with the above-identified co-surfactants. The disclosures of U.S. Pat. No. 4,561,998 and 4,507,219 with respect to co-surfactants are incorporated here by reference.

Softergent

Softergent technologies as described in, for example, U.S. Pat. Nos. 6,949,498, 5,466,394 and 5,622,925 can be used in compositions of the present technology. The term "softergent" refers to a softening detergent that can be dosed at the beginning of a wash cycle for the purpose of simultaneously cleaning and softening fabrics. The magnesium ion containing sulfonated estolide formulations of the present technology can be used to make stable, aqueous heavy duty liquid laundry detergent compositions containing a fabric-softening agent that provide exceptional cleaning as well as fabric softening and anti-static benefits.

For example, a softergent composition of the present technology can contain about 0.5% to about 10%, preferably from about 2% to about 7%, more preferably from about 3% to about 5% by weight of a quaternary ammonium fabric-softening agent having the formula:

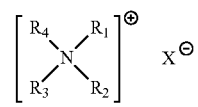

wherein $R_1$ and $R_2$ are individually selected from the group consisting of $C_1$-$C_4$ alkyl, $C_1$-$C_4$ hydroxy alkyl, benzyl, and —$(C_2H_4O)_xH$ where x has a value from 2 to 5; X is an anion; and (1) $R_3$ and $R_4$ are each a $C_8$-$C_{14}$ alkyl or (2) $R_3$ is a $C_8$-$C_{22}$ alkyl and $R_4$ is selected from the group consisting of $C_1$-$C_{10}$ alkyl, C—$C_{10}$ hydroxy alkyl, benzyl, and —$(C_2H_4O)_xH$ where x has a value from 2 to 5.

Preferred fabric-softening agents are the mono-long chain alkyl quaternary ammonium surfactants wherein the above formula $R_1$, $R_2$, and $R_3$ are each methyl and $R_4$ is a $C_8$-$C_{18}$ alkyl. The most preferred quaternary ammonium surfactants are the chloride, bromide and methylsulfate $C_{8-16}$ alkyl trimethyl ammonium salts, and $C_{8-16}$ alkyl di(hydroxyethyl)-methyl ammonium salts. Of the above, lauryl trimethyl ammonium chloride, myristyl trimethyl ammonium chloride and coconut trimethylammonium chloride and methylsulfate are particularly preferred. For example, ADOGEN 412™, a lauryl trimethyl ammonium chloride commercially available from Witco, is a preferred softening agent.

Another class of preferred quaternary ammonium surfactants are the di-$C_8$-$C_{14}$ alkyl dimethyl ammonium chloride or methylsulfates; particularly preferred is di-$C_{12}$-$C_{14}$ alkyl dimethyl ammonium chloride. This class of materials is particularly suited to providing antistatic benefits to fabrics. Materials having two alkyl chain lengths longer than $C_{14}$, like di-$C_{16}$-$C_{18}$ alkyl dimethyl ammonium chloride, which are commonly used in rinse added fabric softeners, are not included in the presently described technology, since they do not yield isotropic liquid detergents when combined with the anionic surfactants described above.

A preferred softergent embodiment of the present technology comprises the detergent composition wherein the weight ratio of anionic surfactant component to quaternary ammonium softening agent is from about 3:1 to about 40:1 and a preferred range from about 5:1 to 20:1.

Odor Control

Odor control technologies as described in, for example, U.S. Pat. No. 6,878,695 can be used in compositions of the present technology.

For example, a composition containing magnesium ions and one or more of the sulfonated estolides of fatty acids of the present technology can further comprise a low-degree of substitution cyclodextrin derivative and a perfume material. The cyclodextrin is preferably functionally-available cyclodextrin. The compositions can further comprise optional cyclodextrin-compatible and—incompatible materials, and other optional components. Such a composition can be used for capturing unwanted molecules in a variety of contexts, preferably to control malodors including controlling malodorous molecules on inanimate surfaces, such as fabrics, including carpets, and hard surfaces including countertops, dishes, floors, garbage cans, ceilings, walls, carpet padding, air filters, and the like, and animate surfaces, such as skin and hair.

The low-degree of substitution cyclodextrin derivatives useful in the present technology are preferably selected from low-degree of substitution hydroxyalkyl cyclodextrin, low-degree of substitution alkylated cyclodextrin, and mixtures thereof. Preferred low-degree of substitution hydroxyalkyl beta-cyclodextrins have an average degree of substitution of less than about 5.0, more preferably less than about 4.5, and still more preferably less than about 4.0. Preferred low-degree of substitution alkylated cyclodextrins have an average degree of substitution of less than about 6.0, more preferably less than about 5.5, and still more preferably less than about 5.0.

The compositions of the present technology can comprise a mixture of cyclodextrins and derivatives thereof such that the mixture effectively has an average degree of substitution equivalent to the low-degree of substitution cyclodextrin derivatives described hereinbefore. Such cyclodextrin mixtures preferably comprise high-degree of substitution cyclodextrin derivatives (having a higher average degree of substitution than the low-degree substitution cyclodextrin derivatives described herein) and non-derivatized cyclodextrin, such that the cyclodextrin mixture effectively has an average degree of substitution equivalent to the low-degree of substitution cyclodextrin derivative. For example, a composition comprising a cyclodextrin mixture containing about 0.1% non-derivatized beta-cyclodextrin and about 0.4% hydroxypropyl beta-cyclodextrin having an average degree of substitution of about 5.5, exhibits an ability to capture unwanted molecules similar to that of a similar composition comprising low-degree of substitution hydroxypropyl beta-cyclodextrin having an average degree of substitution of about 3.3. Such cyclodextrin mixtures can typically absorb odors more broadly by complexing with a wider range of unwanted molecules, especially malodorous molecules, having a wider range of molecular sizes preferably at least a portion of a cyclodextrin mixture is alpha-cyclodextrin and its derivatives thereof, gamma-cyclodextrin and its derivatives thereof, and/or beta-cyclodextrin and its derivatives thereof; more preferably a mixture of alpha-cyclodextrin, or an alpha-cyclodextrin derivative, and derivatized beta-cyclodextrin, even more preferably a mixture of derivatised alpha-cyclodextrin and derivatized beta-cyclodextrin; and most preferably a mixture of hydroxypropyl alpha-cyclodextrin and hydroxypropyl beta-cyclodextrin, and/or a mixture of methylated alpha-cyclodextrin and methylated beta-cyclodextrin.

The cavities within the functionally-available cyclodextrin in the compositions of the present technology should remain essentially unfilled (i.e. the cyclodextrin remains uncomplexed and free) or filled with only weakly complexing materials when in solution, in order to allow the cyclodextrin to absorb (i.e. complex with) various unwanted molecules, such as malodor molecules, when the composition is applied to a surface containing the unwanted molecules. Non-derivatized (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit Non-derivatized beta-cyclodextrin is generally not preferred when the composition contains surfactant since it affects the surface activity of most of the preferred surfactants that are compatible with the derivatized cyclodextrins.

The level of low-degree of substitution cyclodextrin derivatives that are functionally-available in the odor control compositions of the present technology is typically at least about 0.001%, preferably at least about 0.01%, and more preferably at least about 0.1%, by weight of the composition. The total level of cyclodextrin in the present composition will be at least equal to or greater than the level of functionally-available cyclodextrin. The level of functionally-available will typically be at least about 10%, preferably at least about 20%, and more preferably at least about 30%, by weight of the total level of cyclodextrin in the composition.

Concentrated compositions can also be used. When a concentrated product is used, i.e., when the total level of cyclodextrin used is from about 3% to about 60%, more preferably from about 5% to about 40%, by weight of the concentrated composition, it is preferable to dilute the concentrated composition before treating fabrics in order to avoid staining. Preferably the concentrated cyclodextrin composition is diluted with about 50% to about 6000%, more preferably with about 75% to about 2000%, most preferably with about 100% to about 1000% by weight of the concentrated composition of water. The resulting diluted compositions have usage concentrations of total cyclodextrin and functionally-available cyclodextrin as discussed hereinbefore, e.g., of from about 0.1% to about 5%, by weight of the diluted composition of total cyclodextrin and usage concentrations of functionally-available cyclodextrin of at least about 0.001%, by weight of the diluted composition.

Forms

The laundry detergent compositions of the present technology can take any of a number of forms and any of the different delivery systems that are currently known or to be developed in the future such as ready-to-use, dilutable, wipes, etc.

For example, the compositions of the present technology can take the form of a dilutable fabric detergent or conditioner, that may be an isotropic liquid, a surfactant-structured liquid, a granular, spray-dried or dry-blended powder, a tablet, a paste, a molded solid, a water soluble sheet, or any other laundry detergent form known to those skilled in the art. A "dilutable" fabric detergent or conditioning composition is defined, for the purposes of this disclosure, as a product intended to be used by being diluted with water or a non-aqueous solvent by a ratio of more than 100:1, to produce a liquor suitable for treating textiles. "Green concentrate" compositions like those on the market today for Fantastic®, Windex® and the like, can be formulated such that they could be a concentrate to be added to a bottle for final reconstitution.

The compositions of the present technology could also be formulated as a gel or a gel packet like the dishwasher products on the market today. Water soluble sheets or sachets, such as those described in U.S. Pat. Appl. No. 20020187909, which is incorporated herein by reference, are also envisaged as a potential form of the present technology. These may be sold under a variety of names, and for a number of purposes. The composition can also be deposited on a wiper or other substrate.

Polymeric Suds Enhancers

In accordance with some embodiments, polymeric suds enhancers such as those described in U.S. Pat. No. 6,903,064 can be used in compositions of the present technology. For example, the detergent compositions of the present technology may further comprises an effective amount of polymeric suds volume and suds duration enhancers. These polymeric materials provide enhanced suds volume and suds duration during cleaning.

One example of a polymeric suds stabilizer suitable for use in a composition of the present technology is selected from the group consisting of:

(i) a polymer comprising at least one monomeric unit having the formula:

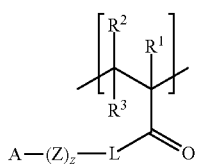

wherein each of $R^1$, $R^2$ and $R^3$ are independently selected from the group consisting of hydrogen, $C_1$ to $C_6$ alkyl, and mixtures thereof; L is O; Z is $CH_2$; z is an integer selected from about 2 to about 12; A is $NR^4R^5$, wherein each of $R^4$ and $R^5$ is independently selected from the group consisting of hydrogen, $C_1$ to $C_8$ alkyl, and mixtures thereof, or $NR^4R^5$ form an heterocyclic ring containing from 4 to 7 carbon atoms, optionally containing additional hetero atoms, optionally fused to a benzene ring, and optionally substituted by $C_1$ to $C_8$ hydrocarbyl;

(ii) a proteinaceous suds stabilizer having an isoelectric point form about 7 to about 11.5;

(iii) a zwitterionic polymeric suds stabilizer; and (iv) mixtures thereof.

Preferably, the exemplary polymeric suds stabilizer described above has a molecular weight of from about 1,000 to about 2,000,000 daltons and more preferably the molecular weight is about 5,000 to about 1,000,000.

Methods of Laundering Fabrics

Methods for laundering fabrics with SE, PHSE, or HSE-based formulations are contemplated. Such methods involve placing fabric articles to be laundered in a high efficiency washing machine or a regular (non-high efficiency) washing machine and placing an amount of the SE, PHSE, or HSE-based composition sufficient to provide a concentration of the composition in water of from about 0.001% to about 5% by weight when the machine is operated in a wash cycle. A high efficiency machine is defined by the Soap and Detergent Association as any machine that uses 20% to 66% of the water, and as little as 20%-50% of the energy, of a traditional, regular agitator washer (SDA "Washers and Detergents" publication 2005; http://www.cleaning101.com/laundry/HE.pdf. The wash cycle is actuated or started to launder the fabric articles.

General Considerations for Liquid Laundry Detergent Compositions Comprising Magnesium Sulfate The present technology also provides and relates to liquid laundry detergent compositions comprising about 1% to about 99% by weight of at least one compound of general Formula 1; about 0.5% to about 5% by weight of magnesium sulfate; 0.1% to about 40% by weight of at least one alkyl ester sulfonate; and about 1% to about 99% by weight of a carrier such as water. In some embodiments, W in Formula 1 is potassium and the total surfactant concentration is greater than about 40%, alternatively greater than about 20%. The composition can further comprise 0% to about 40% by weight of at least one additive, such as, but not limited to, a member selected from the group consisting of at least one builder, at least one alkaline agent, at least one enzyme, at least one chelating agent, at least one polymeric dispersing agent, at least one suds suppressor, at least one alkyl polyglucoside, at least one polymeric suds enhancer, at least one antimicrobial agent, at least one softener, at least one odor control agent, at least one thickener, derivatives thereof, and combinations thereof.

In some embodiments, the composition has improved anti-redeposition properties as compared to an analogous heavy duty detergent based on at least one linear alkylbenzene sulfonate, at least one alcohol ether sulfate, or a mixture thereof that does not contain at least one compound of Formula 1.

The compositions can comprise at least one additional surfactant or at least one additional additive for improving laundering of a material soiled with grass, or spaghetti sauce, or dust/sebum containing soil. The material can be at least one cotton fabric, at least one polyester cotton blend, at least one polyester fabric, at least one silk material, at least one nylon material, at least one wool material, or a combination thereof. In some embodiments, the additional surfactant is an anionic surfactant, such as alkyl ether sulfate.

The formulation can be a biodegradable formulation. The formulation can be a liquid (e.g., a pourable liquid), a powder, a gel, a single-dose pouch, a solid, or a semi-solid at ambient conditions. The formulation can have a viscosity of about 10 to about 1000 cps, measured at a temperature of 25° C., with a Brookfield model LV viscometer, using a #2 spindle rotated at 5 rpm. The compound of Formula 1 can be effective to reduce the pour point of the formulation. The formulation can exhibit a pH of about 5 to about 13.5.

A laundry concentrate composition is also provided, comprising about 1% to about 99% by weight of at least one compound according to general Formula 1; about 0.5% to about 5% by weight of magnesium sulfate; 0.1% to about 40% by weight of at least one alkyl ester sulfonate; about 1% to about 99% by weight of water; and 0% to about 40% by weight of at least one additive. In some embodiments, the laundry concentrate comprises surfactants in a total amount of about 20% by weight or higher, alternatively about 40% by weight or higher, alternatively about 60% by weight or higher. The composition can further comprise about 1% to about 90% by weight of at least one nonionic surfactant. The composition can have a pH value greater than about 8 or less than about 6, or a pH value maintained in a range that enables a clear, homogeneous liquid product, free of substantial precipitation or other physical form instability. The homogenous liquid product can contain one or more of at least one inorganic salt, at least one non-sulfonated-estolide, or at least one fatty acid, and be maintained at a temperature in the range of about 40° F. to about 200° F.

An exemplary laundry detergent composition comprises about 5% to about 90% by weight of at least one compound according to general Formula 1; about 0.5% to about 3% by weight of magnesium sulfate; about 4% to about 50% by weight of at least one alkyl ester sulfonate; 0% to about 25% by weight of cocamide diethanolamine; and the composition has a pH value in the range of about 7 to about 10. Another exemplary laundry detergent composition comprises about 2% to about 90% by weight of one or more compounds according to general Formula 1; about 0.5% to about 3% by weight of magnesium sulfate; about 2% to about 40% by weight of at least one nonionic surfactant; 0% to about 32% by weight of at least one alcohol ether sulfate; 0% to about 25% by weight of at least one alkyl methyl ester sulfonate; 0% to about 6% by weight of lauryl dimethlyamine oxide; 0% to about 6% by weight of $C_{12}EO_3$; 0% to about 10% by weight of coconut fatty acid; 0% to about 3% by weight of borax pentahydrate; 0% to about 6% by weight of propylene glycol; 0% to about 10% by weight of sodium citrate; 0% to about 6% by weight of triethanolamine; 0% to about 6% by weight of monoethanolamine; 0% to about 1% by weight of at least one fluorescent whitening agent; 0% to about 1.5% by weight of at least one anti-redeposition agent; 0% to about 2% by weight of at least one thickener; 0% to about 2% by weight of at least one thinner; 0% to about 2% by weight of at least one protease; 0% to about 2% by weight of at least one amylase; and 0% to about 2% by weight of at least one cellulase. An exemplary green laundry detergent composition comprises about 2% to about 90% by weight of one or more compounds according to general Formula 1; about 0.5% to about 3% by weight of magnesium sulfate; 0% to about 30% by weight of at least one C16 methyl ester sulfonate, or C12 methyl ester sulfonate, or a blends of C12-C18 methyl ester sulfonates; 0% to about 30% by weight of sodium lauryl sulfate; 0% to about 30% by weight of sodium stearoyl lactylate; 0% to about 30% by weight of sodium lauroyl lactate; 0% to about 60% by weight of alkyl polyglucoside; 0% to about 60% by weight of polyglycerol monoalkylate; 0% to about 30% by weight of lauryl lactyl lactate; 0% to about 30% by weight of saponin; 0% to about 30% by weight of rhamnolipid; 0% to about 30% by weight of sphingolipid; 0% to about 30% by weight of glycolipid; 0% to about 30% by weight of at least one abietic acid derivative; and 0% to about 30% by weight of at least one polypeptide.

The present technology also relates to methods for laundering or hand laundering one or more fabric articles using one or more of the foregoing compositions comprising at least one compound according to general Formula 1, at least one alkyl ester sulfonate, and magnesium sulfate. Steps included in such methods are discussed elsewhere in this specification. In such methods, the composition can contain magnesium sulfate in an amount effective to improve the cleanliness of the one or more fabric articles treated according to the method, and/or a sufficient amount of magnesium sulfate effective to increase the viscosity of the composition.

In some embodiments of the present laundry formulations including HDL formulations with or without $MgSO_4$ and LDL formulations, the composition is capable of being used in a high efficiency or regular washing machine.

In some embodiments, at least one of the compounds of Formula 1 is a potassium salt. The compound of Formula 1 can be formed from all renewable carbon sources, such as by the process comprising the steps of:

sulfonating one or more fatty acids obtained from at least one animal fat, vegetable fat, or oil source, or combinations thereof, to form a secondary sulfonate reaction; and condensing the secondary sulfonate reaction product to form one or more estolide components.

General Considerations for Light Duty Liquid Laundry Detergents

Compositions of the present technology comprising at least one compound as defined by general Formula 1 and at least one alkyl ester sulfonate are suitable for inclusion in light duty liquid (LDL) detergent formulations.

Desirable attributes for light duty liquid detergents, in general, include the ability to emulsify, suspend or penetrate greasy or oily soils and suspend or disperse particulates, in order to clean articles or surfaces; and then prevent the soils, grease, or particulates from re-depositing on the newly cleaned articles or surfaces. It is also desirable for the light duty liquid to provide sustained foaming in dilute wash solution in the presence of the soils being cleaned. In order to optimize these attributes, it is desirable to produce LDLs that contain moderate to high levels of surfactants (e.g., greater than about 20% total surfactant) in combinations and types that would typically produce gels instead of liquids. Surprisingly, the present technology now demonstrates that the addition of at least one sulfo-estolide surfactant, having the general structure of general Formula 1 as described herein, to LDL formulations, for example, decreases the viscosity of such a formulation into a workable liquid range at room temperature. Further, the sulfo-estolide containing LDL formulations of the present technology maintain high foaming and optimized cleaning attributes. Other desirable attributes of the present technology include an ability of being in liquid form at room temperature; an ability to formulate in cold-mix applications; an ability to perform as good as or better than existing conventional surfactants or formulations containing such conventional surfactants with respect to foaming level and soil removal, as well as other properties as described herein.

Formulations are contemplated having a viscosity of about 5 cPs to about 2000 cPs, measured at 25° C. using a Brookfield Viscometer model LV, with spindle 2, 3 or 4 at speeds ranging from about 12 rpm to about 50 rpm. LDL formulations containing at least one sulfo-estolide surfactant having the general structure of general Formula 1 and at least one alkyl ester sulfonate have lower viscosity than comparable formulations lacking such surfactants. Since the compounds according to general Formula 1 function as viscosity reducers, they are very useful for making the contemplated highly concentrated, (e.g. greater than about 20% surfactant active, and even beyond 40% active) LDL detergent formulations. Liquid compositions greater than 40% active would be very useful for performance and economy, but have heretofore been unattainable except for the use of large quantities of undesirable solubilizing alcohols as described above.

Various formulations of the present technology exhibit viscosities of from about 100 cps to about 10,000 cps; alternatively, from about 100 cps to about 6,000 cps, alternatively from about 200 cps to about 6,000 cps, measured at 25° C. using a Brookfield Viscometer model LV, with spindle 2, 3 or 4 at speeds ranging from about 12 rpm to about 50 rpm.

It is also desirable to have the ability to control the foaming of different household, industrial and institutional products depending on the desired end-use applications. For example, for one or more light duty liquid detergents of the present technology, it is desirable to have suitable foaming ability along with a viscosity that corresponds to a flowable liquid at room temperature.

It is also desirable to have the ability to produce "green" LDL formulations. Thus, the surfactants should be ultimately biodegradable, phosphate free, and non-toxic. To meet consumer perceptions and reduce the use of petrochemicals, a "green" formula may also advantageously be limited to the use of renewable hydrocarbons, such as vegetable or animal fats and oils, in the manufacture of one or more surfactant components. The presently described sulfo-estolide surfactants are derived from plant and/or animal fats and oils and thereby address this challenge.

It is also desirable for the pH of LDL detergents to be in the range in which contact with hands and skin is acceptable while maintaining adequate foaming and cleaning properties. The presently described compositions achieve this need by possessing adequate soil removal and foaming properties at or around neutral pH. Sulfo-estolide surfactant containing LDL detergents of the present technology have pH values in the range of from about 3 to about 10; alternatively, from about 4 to about 9; and preferably from about 6 to about 8.

LDL Formulations

A wide variety of compositions can be made that include at least one sulfo-estolide surfactant or two or more sulfo-estolide surfactants, as described herein, with or without other ingredients as specified herein. Formulations are contemplated containing, for example, sulfo-estolide surfactants from between about 0.1% to about 90% by active weight, alternatively between about 0.1% to about 50% by active weight, alternatively, between about 0.1% to about 35% by active weight, alternatively, between about 1% to 30% by active weight based on the total weight of the composition.

The sulfo-estolide surfactants having the general structure of general Formula 1 described herein can be incorporated into, for example, various formulations and used as surfactants, emulsifiers, skin feel agents, film formers, rheological modifiers, solvents, release agents, lubrication agents, conditioners, dispersants, hydrotropes, etc. Such compositions can be used in end-use applications including, but not limited to, household and industrial and institutional cleaning products.

Certain embodiments of the present technology contain additional surfactants in the amounts of from about 2% to about 70% by active weight; alternatively, from about 5% to about 45% by active weight; alternatively, from about 10% to about 30% by active weight based on the total ingredient weight of the composition.

Preferred additional surfactants for LDL formulations include, for example, Steol CS-270 (lauryl 2-mole average ether sulfonate), Steol CS-170 (lauryl 1-mole average ether sulfonate), Steol CS-330 (lauryl 3-mole average ether sulfonate), Bio-Soft EC-690 (alcohol ethoxylate), Bio-Soft D-40 (sodium alkylbenzenesulfonate), Bio-Soft S-101 (alkylbenzene sulfonic acid) neutralized with sodium, potassium, ammonium and/or magnesium, Bio-Terge AS-40 (sodium olefin sulfonate), Alpha-Step PC-48 (alkyl methyl ester sulfonate) and/or Stepanol WA-Extra K (sodium lauryl sulfate), all from the Stepan Company, Northfield Ill.

In alternative embodiments, sulfo-estolide surfactants having the general structure of general Formula 1 can be used to produce anti-bacterial formulations. One or more sulfo-estolide based LDL anti-bacterial compositions of the present technology can include from 0% to about 10% by weight of a polyvalent metal ion chelant, alternatively from about 0.1% to about 10%, alternatively from about 1% to about 10%, alternatively from about 1% to about 5% by weight, and may additionally include any range or percentage there between, including, but not limited to, for example, increments of about 0.1, 0.2, 0.3, 0.4, 0.5, 0.6, 0.7, 0.8, 0.9, 1.0. 2.5, 5% and multiplied factors thereof, such as 1.5×, 2.0×, 3.0×, 4.0×, 5.0× and 6.0× as desired to achieve higher concentrates. Further, the antimicrobial compositions can further include from 0% to about 10% of an alkaline builder, alternatively from about 0.1% to about 10%, alternatively from about 1% to about 10%, alternatively from about 1% to about 5% by weight, and may additionally include any range or percentage there between, including, but not limited to, for example, increasing or decreasing increments of about 0.1, 0.2, 0.3, 0.4, 0.5, 0.6, 0.7, 0.8, 0.9 or 1.0% 2.5%, 5% and multiplied factors thereof, such as 1.5×, 2.0×, 3.0×, 4.0×, 5.0× and 6.0× as desired to achieve higher concentrates. Suitable alkaline builders include, but are not limited to sodium carbonate, potassium pyrophosphate, sodium metasilicate, or combinations thereof. Further, such antimicrobial compositions may also include at least one additional component, for example dyes and fragrances, from 0% to about 2% by weight, alternatively from about 0.01% to about 2%, alternatively from about 0.1% to about 2%, alternatively from about 0.1% to about 1% by weight, and including any percentage or range there between, including, but not limited to for example, alternatively from about 0.1% to about 10%, alternatively from about 1% to about 10%, alternatively from about 1% to about 5% by weight, and may additionally include any range or percentage there between, including, but not limited to, for example, increasing or decreasing increments of about 0.1, 0.2, 0.3, 0.4, 0.5, 0.6, 0.7, 0.8, 0.9 or 1.0%, 2.5%, 5% and multiplied factors thereof, such as 1.5×, 2.0×, 3.0×, 4.0×, 5.0× and 6.0× as desired to achieve higher concentrates.

LDL antimicrobial components of the present technology can also include, but are not limited to triclosan, n-alkyl dimethyl benzyl ammonium chloride, n-alkyl dimethyl benzyl ammonium chloride, dialkyl dimethyl ammonium chloride, didecyl dimethyl ammonium chloride, dioctyl dimethyl ammonium chloride, phenolics, iodophors, pine oil, methyl salicylate, morpholine, silver, copper, bromine, and quaternary ammonium compounds, derivatives thereof, and combinations thereof including, but not limited to, the polyquaternium series as is used in hand soap formulations, and 3,4, 4'trichlorocarbanilide as disclosed in U.S. Pat. No. 6,605,579.

Optionally, the LDL detergent compositions of the present technology can include at least one additive as well. Suitable additives include, but are not limited to viscosity modifiers, electrolytes, thickeners, emollients, skin conditioning agents, emulsifier/suspending agents, solubilizing agents, fragrances, colors, dyes, herbal extracts, vitamins, builders, enzymes, pH adjusters, preservatives, antimicrobial and/or antibacterial agents, antidandruff agents, polymers, magnesium sulfate, derivatives thereof, combinations thereof, and other ingredients commonly known in the art as an additive.

Magnesium sulfate, builders, solubilizing agents and enzymes may be added to aid in cleansing ability, for example. Emollients (including, without limitation, vegetable oils, mineral oils, silicone oils, petrolatum, polyglycerol methyl esters, and esters), skin conditioning agents (such as glycerine and free fatty acid), vitamins and herbal extracts may be added to further improve conditioning performance. Fragrances, dyes, opacifying agents, and pearlescent agents may also be added to further enhance the appearance and smell of one or more of the finished LDL formulations of the present technology. Suitable preservatives such as benzyl alcohol, methyl paraben, propyl paraben, Methylchloroisothiazolinone, and Methylisothiazolinone, 2-methyl-4-isothiazolin-3-one, 1,2-benzisothiazolin-3-one, imidazolidinyl urea and 1,3-Dimethylol-5,5-dimethylhydantoin (Glydant) may also be utilized among others. Furthermore, a dimethyl polysiloxane as well as others may be utilized to enhance skin feel and conditioning properties to hair.

Enzymes suitable for use in the practice of the present technology include proteases, amylases and lipases.

Polymers suitable for use in the practice of the present technology include, for example, anionic polymers, acrylates, hydroxyethylcelluloses, zwitterionic polymers, gelatins, xanthan gums, polysaccharides, polyethylene glycols, derivatives thereof, and combinations thereof.

Sulfo-estolide surfactant containing LDL detergents of the present technology that comprise from about 1% to about 99.9% of at least one carrier are also contemplated.

General Considerations for Personal Care Products

The present technology also provides and relates to personal care formulations comprising a compound as defined by general Formula 1 and an alkyl ester sulfonate. Such personal care formulations include, for example, but not limited to, facial cleaners, liquid hand soap, body wash and/or shampoos which have superior foam ability. Further, these personal care formulations may be diluted to make more cost-effective formulations that have similar foaming characteristics as the control.

In some embodiments, the present personal care formulations have a viscosity from about 10 cps to about 50,000 cps, alternatively from about 2,000 cps to about 20,000 cps, alternatively from about 1,000 to about 3,000 cps, as measured at a temperature of 25° C. with a Brookfield model RVT viscometer at 20 rpm (available from Brookfield Engineering Laboratories, Inc. Middleboro, Mass.). In some embodiments, the present personal care formulations have a pH value in the range of about 5 to about 10, alternatively about 5 to about 7. In some embodiments, the formulations further comprise at least one additive. In some embodiments, the present personal care formulations comprise about 0.1% to about 90% by weight of at least one compound having the general Formula 1; about 1% to about 90% by weight of at least one alkyl ester sulfonate; about 1% to about 50% by weight of at least one surfactant; and about 1% to about 99% by weight of at least one carrier; and wherein the formulation has a total surfactant concentration of about 20% by weight or greater. In some embodiments, the present personal care formulations comprise one or more additives.

The present liquid personal care compositions comprise about 0.1% to about 99% by weight of at least one surfactant according to general Formula 1; about 0.1% to about 85% by weight of at least one alkyl ester sulfonate, and about 1% to about 99% by weight of at least one carrier, such as water.

The compositions can comprise about 1% to about 40% by weight, alternatively about 1% to about 20% by weight, alternatively about 1% to about 10% by weight, alternatively about 1% to about 5% by weight, of at least one surfactant of Formula 1. The compositions can comprise 1% to about 30% by weight, alternatively about 1% to about 20% by weight, alternatively about 5% to about 20% by weight, alternatively about 5% to about 30% by weight of the at least one alkyl ester sulfonate. The compositions can comprise a second additional surfactant, for example, as about 1% to about 20% by weight, alternatively about 1% to about 10% by weight, alternatively about 1% to about 5% by weight of the total composition. Such surfactants can be selected from the group consisting of anionic, non-ionic, amphoteric, zwitterionic, semipolar non-ionic, cationic, amphoteric, and mixtures thereof. Specific surfactants may be selected from those listed above. The present liquid personal care compositions can further comprise about 1% to about 85% by weight of at least one solvent. The compositions can further comprise at least one additive, including but not limited to a member selected from the group consisting of viscosity modifiers, electrolytes, emollients, skin conditioning agents, emulsifier/suspending agents, fragrances, colors, herbal extracts, vitamins, builders, enzymes, pH adjusters, preservatives, antibacterial agents, antidandruff agents, derivatives thereof, and combinations thereof.

In some embodiments, the personal care formulation has a viscosity of about 10 to about 50,000 cps, measured at a temperature of 25° C., with a Brookfield model RVT viscometer at 20 rpm. Alternatively, the formulation has a viscosity of about 2,000 to about 20,000 cps, alternatively about 1,000 to about 3,000 cps, measured at a temperature of 25° C., with a Brookfield model RVT viscometer at 20 rpm. The compound of Formula 1 can be effective to reduce the pour point of the formulation. The formulation can exhibit a pH of about 3.5 to about 13.5, alternatively about 5 to about 10, alternatively about 5 to about 9, alternatively about 5.0 to about 6.5, alternatively about 5.5 to about 6.5. In some embodiments, the formulation has an increased foaming capability.

The present liquid personal care compositions can be a liquid hand soap, a body wash, a facial cleaner, a shampoo, a 2-in-1 shampoo or an antidandruff shampoo.

In some embodiments, the present personal care compositions comprise about 5% to about 90% by weight of at least one compound according to general Formula 1; 0.1% to about 50% by weight of at least one alkyl ester sulfonate; 0% to about 25% by weight of at least one solvent; 1% to about 99% by weight of at least one carrier, and wherein the composition has a pH value in the range of about 5 to about 10. For example, the compound of Formula 1 can comprise about 5% to about 40% by weight of the composition, and the at least one alkyl ester sulfonate can comprise about 1% to about 50% by weight, alternatively about 1% to about 25% by weight, of the composition. The at least one solvent can comprise about 1% to about 25% by weight of the composition. The pH value can be in the range of about 5 to about 7, and the personal care composition can further comprise at least one additive. The compositions can have a viscosity with one of the viscosity ranges described above.

Personal care composition concentrates (for example, a liquid hand soap or a body wash concentrate) are is also provided. The concentrate composition comprises about 1% to about 90% by weight of at least one surfactant according to general Formula 1. The concentrate composition also comprises 1% to about 50% by weight of at least one alkyl ester sulfonate, and 1% to about 99% by weight of at least one carrier. The concentrate composition has a total surfactant concentration of about 30% by weight or more. The compositions can have a viscosity with one of the viscosity ranges described above. The present personal care composition concentrates can have a total surfactant concentration of 35% by weight or more, and can further comprise a second additional surfactant, for example as about 1% to about 10% by weight of the composition. The composition concentrate can further comprise at least one solvent.

General Considerations for Dishwashing Detergent Compositions

The present technology also provides and relates to liquid machine dishwashing detergent compositions (including gels or liquids). For example a low-foaming liquid machine dishwashing detergent composition comprises about 0.1% to about 20% by active weight, alternatively about 1% to about 10% by active weight, alternatively about 5% to about 10% by active weight, of one or more surfactants of the general Formula 1; about 0.1% to about 20% by weight of at least one alkyl ester sulfonate; about 0.01% to about 10% by active weight, alternatively about 1% to about 5% by active weight of at least one enzyme, and the balance being a carrier. The low-foaming liquid machine dishwashing detergent composition has a pH from about 9 to about 14, alternatively from about 9 to about 11, alternatively from about 10 to about 11.

An exemplary biodegradable dishwashing detergent composition is provided, which comprises from about 0.1% to about 20% by active weight, alternatively about 1% to about 20% by active weight, alternatively about 5% to about 10% by active weight, of one or more low-foaming surfactants according to the general Formula 1; about 0.1% to about 20% by weight of at least one alkyl ester sulfonate; and from about 0.01% to about 10% by active weight of at least one enzyme. The dishwashing detergent composition has a pH from about 9 to about 14, and is substantially free of phosphate, or substantially free of phosphate and substantially free of chloride.

In the foregoing low-foaming and biodegradable dishwashing detergent compositions, one or more enzymes can be about 1% to about 5% by active weight of the composition. Suitable enzymes include, but are not limited to, amylase (preferably an alkaline stable amylase), or proteinase (preferably an alkaline stable proteinase). The viscosity of the dishwashing detergent compositions can be from about 1000 cps to about 6000 cps as measured by Brookfield Viscometer LV, S63 at 50 rpm at 25° C. The low foaming composition can further comprise at least one additional low-foaming surfactant, such as a surfactant selected from the group consisting of sodium octane sulfonate, polyalkolylated aliphatic base, polyalkoxylated aliphatic base, sodium alphasulfo methyl C12-18 ester and disodium alphasulfo C12-18 fatty acid. In some embodiments, the at least one additional low-foaming surfactant is about 1% to about 20% by active weight of the composition. The compositions can also comprise at least one builder, as about 0.1% to about 40% by weight, alternatively about 5% to about 30% by weight of the total composition. The compositions can further comprise at least one additive, such as an additive is a selected from the group consisting of silvercare, anti-tarnish and/or anti-corrosion agents, pigments, dyes, fillers, germicides, hydrotropes, anti-oxidants, enzyme stabilizing agents, pro-perfumes, perfumes, carriers, processing aids, solvents, anti-abrasion agents, thickeners, and other enzyme stabilizing packaging systems. The additive can be about 0.1% to about 30% by weight, alternatively about 0.1% to about 20% by weight of the composition. The low foaming compositions can further comprise a corrosive protecting agent, such as a metal silicate. The corrosive protecting agent can comprise about 5% to about 20% weight of the composition. The amount of foam produced by the dish washer detergent compositions can be less than about 10 ml, alternatively less than about 5 ml, alternatively less than about 2 ml, as measured by the shake foam test.

Additives to a liquid dishwashing detergent which reduce the foaming of a liquid dishwashing detergent by at least 5% are also provided. Exemplary additives comprise from about 0.1% to about 20% by active weight of one or more surfactants according to general Formula 1. Such additives can reduce the foaming ability of the composition to less than about 10 ml, alternatively less than about 5 ml, alternatively less than about 2 ml, as measured by the shake foam test.

General Considerations for Hard Surface Cleaners

The present technology also relates to and provides general purpose cleaners and hard surface cleaners. The compositions of the present technology comprising at least one compound as defined by general Formula 1 and at least one alkyl ester sulfonate are suitable for inclusion in general purpose cleaner formulations and hard surface cleaner formulations. Such formulations of are suitable to clean, for example, hard surfaces, among other substrates. Any type of surface prone to soiling can be cleaned one or more of the formulations herein described.

Hard surface cleaning products can be made at a neutral pH, but often are made into formulations that are at an acid or alkaline pH to get improved cleaning. When used as a general purpose cleaner, the sulfonated estolide formulation should have a pH of about 6.6 to about 8.3.

In a preferred embodiment, the sulfonated estolide formulation can be used as a degreaser in a heavy duty cleaning application, which could address, for example, engine grease and other lubricants. Other common industrial cleaning applications are described in ECOLAB patent and are hereby incorporated by reference in its entirety. Degreaser formulations would have a pH greater than 12. Sulfonated estolide surfactants can be in the range of 0.1 to 80% weight of active ingredient, preferably about 0.1 to about 50% or about 0.1 to about 20% for concentrated formulations or about 0.1 to about 15% for ready-to-use formulations.

In a preferred embodiment, the sulonfated estoide formulation can be used as a descaler in a cleaning application, which could address, for example, soap scum. Descaler formulations would have a pH less than 5. Sulfonated estolide surfactants can be in the range of 0.1 to 80% weight of active ingredient, preferably about 0.1% to about 50% or about 0.1% to about 20% for concentrated formulations or 0.1-15% for ready-to-use formulations. A non-hydrolyzed sulfonated estolide has shown superior lime soap dispersing power than C11.3 LAS, and SLS, while inferior to anionic, sodium lauryl ether (3EO) sulfate. A hydrolyzed sulfonated estolide did not perform as well as tested anionic surfactants.

The descaling, general purpose and degreasing formulations can be used in all of the different delivery processes such as Ready-To-Use, dilutable, wipes, spray bottles, etc. Most notably, these formulations can be sold in a concentrated form which decreases packing requirements and decreases shipping costs—both of which have a positive environmental impact. These formulations can be concentrated and later diluted in water to form a cleaning composition therefrom Sulfonated estolide surfactants can be in the range of about 0.1% to about 80% weight of active ingredient, preferably about 0.1% to about 50% or about 0.1 to about 20% for concentrated formulations or about 0.1% to about 15% for ready-to-use formulations. These formulations, in some embodiments are stable with enzymes, peroxide, hypochlorite bleach, and other bleaching agents.

The formulations of the present technology may also be used to add detergency and other surfactant properties to bleach, and they may also be included in compositions including a cleaning adjunct. Common cleaning adjuncts are discussed above.

Desirable attributes of the present technology include equal or superior cleaning performance when compared to other surfactants in comparable classic and green formulations and stability in a concentrated formulation.

The general purpose and hard surface cleaner compositions can also include additives, solvents or additional surfactants. Suitable additives include, but are not limited to, dye, fragrance, or polymer opacifier. For household, industrial and institutional cleaning products, both surfactants and solvents are important ingredients. Desirable attributes for such products include the ability to emulsify, suspend or penetrate greasy or oily soils and suspend or disperse particulates, in order to clean surfaces; and then prevent the soils, grease, or particulates from re-depositing on the newly cleaned surfaces.

It is also desirable to have the ability to control the foaming of different household, industrial and institutional products. For example, for hard surface cleaners, it is desirable to have the ability to wet various surface types and couple or suspend soils to leave the surface free from residue in the form of streaking and/or filming.

Both concentrated and ready-to-use formulations are contemplated having a viscosity of 0 centipoise to 2500 centipoise, measured at 25° C. using a Brookfield Viscometer model DV-II+, spindle #2, speed 12 rpm. Preferrably having a viscosity of 0 centipoise to 100 centipoise, measured at 25° C. using a Brookfield Viscometer model DV-II+, spindle #2, speed 60 rpm. Certain SHP, PEHP, or EHP formulations have been found to have lower viscosity than comparable formulations lacking these surfactants, so these compositions function as viscosity reducers, which is very useful for making the contemplated highly concentrated, (e.g. greater than about 40% surfactant active) detergent formulations.

The sulfonated fatty acid products described in this specification can be incorporated into, for example, various compositions and used as surfactants, emulsifiers, skin feel agents, film formers, rheological modifiers, solvents, release agents, lubrication agents, conditioners, and dispersants, hydrotropes, etc. Such compositions can be used in household and industrial and institutional cleaning products.

In one embodiment, the present technology provides hard surface cleaner comprising 0.1% to about 99% of sulfo-estolides of general Formula 1, but preferably in the range of about 0.1% to about 80%, with 1% to about 99% of a carrier.

In one embodiment, the present technology provides hard surface cleaner comprising 0.1% to about 99% of sulfo-estolides of general Formula 1 and 0.1% to about 99% of at least one solvent.

Solvents for Surface Cleaners

Solvents are often integral to hard surface cleaners by preventing streaking or clouding the surface after cleaning. The present technology does not require addition of a solvent, however, one may be optionally included in the formulation. Examples of solvents contemplated herein, include, but are not limited to: isopropanol, ethanol, glycol ethers, e.g., ethylene glycol monobutyl ether, diethyleneglycol monoethyl ether, dipropyleneglycol methyl ether, or triethyleneglycol. Any solvent or mixture thereof would constitute about 0.1% to about 50% the total composition weight in concentrated formulations, but preferably about 0.1% to about 30%, or about 0.1% to about 20%. For ready-to-use formulations, additional surfactants will ranging from about 0.1% to about 20% of total composition weight, but preferably about 0.1% to about 15%.

Solvents can have a detrimental effect on the environment. Certain solvents to be avoided in preferred embodiments are those classified as a hazardous air pollutant or a volatile organic compound. A preferred embodiment of the present technology allows a sulfonated estolide to reduce harmful solvent content, thereby reducing the potential environmental harm. Additionally, by decreasing solvent content (specifically volatile organic compound content), formulations will qualify for certain regulatory approval as "green" products.

Builders and Alkaline Agents

Builders and other alkaline agents are contemplated for use in some embodiments of the present formulations.

Any conventional builder system is suitable for use here, including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders could also be used here. In a preferred embodiment, sodium citrate is used as a builder.

One or more builders include, but are not limited to chelating agents, e.g., ethylenediamine tetraacetic acid and its salts, phosphates, tetrapotassium pyrophosphate, sodium tripolyphosphate, and citrates; acidifiers, e.g., citric acid, glycolic acid, sulfamic acid, phosphoric acid, or oxalic acid; alkali, e.g., sodium metasilicate, sodium carbonate, sodium sesquicarbonate, sodium hydroxide, or triethanolamine Suitable polycarboxylate builders for use here include citric acid, preferably in the form of a water-soluble salt, and derivatives of succinic acid of the following formula:

where R is $C_{10\text{-}20}$ alkyl or alkenyl, preferably $C_{12\text{-}16}$, or where R can be substituted with hydroxyl, sulfo sulfoxyl or sulfone substituents. Specific examples include lauryl succinate, myristyl succinate, palmityl succinate 2-dodecenylsuccinate, or 2-tetradecenyl succinate. Succinate builders are preferably used in the form of their water-soluble salts, including sodium, potassium, ammonium and alkanolammonium salts.

Other suitable polycarboxylates are oxodisuccinates and mixtures of tartrate monosuccinic and tartrate disuccinic acid, as described in U.S. Pat. No. 4,663,071.

Especially for a liquid composition, suitable fatty acid builders for use here are saturated or unsaturated $C_{10\text{-}18}$ fatty acids, as well as the corresponding soaps. Preferred saturated species have from about 12 to about 16 carbon atoms in the alkyl chain. The preferred unsaturated fatty acid is oleic acid. Another preferred builder system for liquid compositions is based on dodecenyl succinic acid and citric acid.

Some examples of alkaline agents include alkalic metal (Na, U, or $NH_4$) hydroxides, carbonates, bicarbonates. Another commonly used builder is borax.

For liquid compositions, the builder or alkaline agent typically comprises from about 1% to about 60%, alternatively between about 1% and about 30%, alternatively between about 2% and about 15%. See U.S. Pat. No. 5,929,022; column 7, start of 2nd paragraph through column 7, end of 6th paragraph, from which much of the preceding discussion comes. Other builders are described in PCT Publ. WO 99/05242, which is incorporated here by reference.

Chelating agents in the amounts of about 0.1% to about 10%, more preferably about 0.5% to about 5% and even more preferably from about 0.8% to about 3% are also contemplated as an optional ingredient. See U.S. Pat. No. 5,929,022; column 10, 1st paragraph to column 10, end of 2nd paragraph.

Additional Additives

Other ingredients that can be included in a composition include, for example, perfumes, that optionally contain ingredients such as aldehydes, ketones, esters, and alcohols. More compositions that can be included are: carriers, hydrotropes, processing aids, dyes, pigments, solvents, bleaches, bleach activators and enzyme stabilizing packaging systems. Any ingredient in this section would comprise 0.0 to 10% of the total composition weight, and more preferably 0.0 to 5%.

The compositions of the present technology can take any of a number of forms and any of the different delivery systems that are currently known or to be developed in the future such as ready-to-use, dilutable, wipes, etc.

For example, the compositions of the present technology can take the form of a dilutable, that may be an isotropic liquid, a surfactant-structured liquid, a granular, spray-dried or dry-blended powder, a tablet, a paste, a molded solid, a water soluble sheet, or any form known to those skilled in the art. A "dilutable" composition is defined, for the purposes of this disclosure, as a product intended to be used by being diluted with water or a non-aqueous solvent by a ratio ranging from 1 to 150 to produce a liquor suitable for treating a surface. "Green concentrate" compositions like those on the market today for Fantastic®, Windex® and the like, can be formulated such that they could be a concentrate to be added to a bottle for final reconstitution.

EXAMPLES

The compositions and processes described here, and ways to make and use them are illustrated by the following examples. Examples stated in the present or future tense are not represented as having been carried out. Examples to the methods of producing and testing sulfo-estolides of the present technology are incorporated by reference in their entirety from PCT Application Serial No. PCT/US09/31455 filed on Jan. 20, 2009, Examples 1-26.

Example 1

Foaming Reduction

The SHP of Example 2 in PCT Application Serial No. PCT/US09/31455 was used in this example. The materials listed in Tables 1 and 2 were tested for foaming under the conditions stated in the table.

TABLE 1

|  | Chicago Tap Water | | w/Castor Oil | |
|---|---|---|---|---|
| Component* | Height (mL) after 5 seconds | Height (mL) after 5 minutes | Height (mL) after 5 seconds | Height (mL) after 5 minutes |
| Neodol 25-7 | 260 | 250 | 177.5 | 145 |
| Neodol 25-9 | 250 | 245 | 175 | 125 |
| SHP | 130 | 100 | 100 | 100 |
| NaLAS | 500+ | 500+ | 200 | 200 |
| 50%-50% SHP - NaLas | 225 | 225 | 195 | 195 |
| Steol CS-370 | 390 | 380 | 305 | 300 |
| Steol CS-270 | 397.5 | 382.5 | 307.5 | 305 |
| MES C16 | 220 | 142.5 | 157.5 | 135 |

TABLE 2

|  | Chicago Tap Water | | w/Castor Oil | |
|---|---|---|---|---|
| Component | Height (mL) After 5 seconds | Height (mL) After 5 minutes | Height (mL) After 5 seconds | Height (mL) After 5 minutes |
| LAS | 500+ | 500+ | 200 | 200 |
| AES-3EO | 390 | 380 | 305 | 300 |
| AES-2EO | 397.5 | 382.5 | 307.5 | 305 |
| AE C 12-C15-7EO | 260 | 250 | 177.5 | 145 |
| AE C12-C15-9EO | 250 | 245 | 175 | 125 |
| 50%-50% LAS & SHP | 225 | 225 | 195 | 195 |
| MES C16 | 220 | 142.5 | 157.5 | 135 |
| SHP | 130 | 100 | 100 | 100 |

In Tables 1 and 2, Neodol 25-7 is an alcohol ethoxylate $C_{12}$-$C_{15}$ chain length with 7 moles of ethylene oxide (Shell Chemicals, Houston, Tex.); Neodol 25-9 is an alcohol ethoxylate $C_{12}$-$C_{15}$ chain length with 9 moles of ethylene oxide; NaLAS is linear alkylbenzene sulfonic acid, sodium salt; Steol® CS-370 is sodium laureth sulfate 3-mole ethylene oxide (Stepan Company, Northfield, Ill.); Steol® CS-270 is sodium laureth sulfate 2-mole ethylene oxide; MES C16 is a C16 methyl ester sulfonate Tables 1 and 2 demonstrate that SHP exhibits significantly lower foaming (from 10 to 90% lower) than many of the major surfactants employed in laundry detergents currently available on the market. SHP also lowered the foaming of other surfactants when combined with them as shown in the 50:50 sample of Example 1 in PCT Application Serial No. PCT/US09/31455 with LAS. The 50:50 Example 1:LAS sample showed a 50% decrease in foam height compared to LAS alone.

Example 2

Concentrated Surfactant Solution

It is often desirable to be able to ship and pump concentrated solutions of surfactant. A mixture of 26.25% of the SHP of Example 2, 26.25% C16 methylester sulfonate and 47.5% water was found to be flowable and pumpable at room temperature (22° C.).

Examples 3A-U

Green Laundry Detergent Formulas

As petroleum reserves continue to dwindle, it is becoming increasingly important to have effective laundry detergents based on bio-renewable sources. Bio-renewable sources include both animal and plant based feedstocks, although plant-based ones are preferred. We define here a Bio-renewable Carbon Index (BCI) for a given ingredient as:

$$BCI = 100 \times (\text{the number of bio-renewable carbon atoms in the molecule/the total number of carbon atoms in the molecule})$$

The following Table 3 details several prophetic core surfactant formulas wherein the BCI for the overall core formula is 100:

TABLE 3

| Surfactant* | Generic Formula | A | B | C | D | E | F | G | H | I | J | K |
|---|---|---|---|---|---|---|---|---|---|---|---|---|
| SE, PHSE, HSE | 2-90 | 20 | 30 | 15 | 10 | 10 | 10 | 15 | 10 | 20 | 20 | 30 |
| C16 methyl ester sulfonate | 0-30 | | | 5 | | | | | | | | |
| C12 methyl ester sulfonate | 0-30 | | | | 10 | | | | | | | |
| Sodium lauryl sulfate | 0-30 | | | | | 10 | | | | | | |
| Sodium coco sulfate | | | | | | | 10 | | | | | |
| Sodium stearoyl lactylate | 0-30 | | | | | | | 5 | | | | |
| Sodium lauroyl lactate | 0-30 | | | | | | | | 10 | | | |
| alkyl polyglucoside (APG) | 0-60 | 20 | 10 | 20 | 20 | 20 | 20 | 20 | 20 | | | |
| Polyglycerol monoalkylate | 0-60 | | | | | | | | | 20 | | |
| Lauryl lactyl lactate | 0-30 | | | | | | | | | | 20 | 10 |
| Saponin | 0-30 | | | | | | | | | | | |
| Rhamnolipid | 0-30 | | | | | | | | | | | |
| Sphingolipid | 0-30 | | | | | | | | | | | |
| Glycolipid | 0-30 | | | | | | | | | | | |
| Abietic acid derivative | 0-30 | | | | | | | | | | | |
| Polypeptide | 0-30 | | | | | | | | | | | |

| Surfactant* | Generic Formula | L | M | N | O | P | Q | R | S | T | U |
|---|---|---|---|---|---|---|---|---|---|---|---|
| SE, PHSE, HSE | 2-90 | 30 | 30 | 30 | 30 | 30 | 30 | 50 | 40 | 30 | |
| C16 methyl ester sulfonate | 0-30 | | | | | | | | | | |
| C12 methyl ester sulfonate | 0-30 | | | | | | | | | | |
| Sodium lauryl sulfate | 0-30 | | | | | | | | 10 | 20 | 20 |
| Sodium coco sulfate | | | | | | | | | | | |
| Sodium stearoyl lactylate | 0-30 | | | | | | | | | | |
| Sodium lauroyl lactate | 0-30 | | | | | | | | | | |
| alkyl polyglucoside (APG) | 0-60 | | | | | | | 20 | 20 | 20 | |
| Polyglycerol monoalkylate | 0-60 | | | | | | | | | | |
| Lauryl lactyl lactate | 0-30 | | | | | | | | | | 10 |
| Saponin | 0-30 | 10 | | | | | | | | | |
| Rhamnolipid | 0-30 | | 10 | | | | | | | | |
| Sphingolipid | 0-30 | | | 10 | | | | | | | |
| Glycolipid | 0-30 | | | | 10 | | | | | | |
| Abietic acid derivative | 0-30 | | | | | 10 | | | | | |
| Polypeptide | 0-30 | | | | | | 10 | | | | |

*For the methyl ester sulfonates, the methanol from which the ester is made is from bio-renewable sources. APGs of varying HLB values are available from Henkel - a preferred APG is Glucopon 425N. A preferred polyglycerol monoalkylate is triglycerol monolaurate as described in Kato, et al., *Journal of Surfactants and Detergents*, October, 2003, Vol. 6, Number 4, pg. 331. Tea saponin is available from Shanghai Greenway. Quillaja saponin is available from Sigma Chemical Co. More details of many of these surfactants are described in *Surfactant Science Series*, Marcel Dekker, Vols. 25 and 48, incorporated herein by reference.

These core surfactant formulations are not intended to be limiting in any way—optional ingredients described herein regarding the presently described technology can be added in the proportions described. In each case, these are intended to be liquid detergent formulas and, after the addition of optional ingredients, water would be used to bring the total weight up to 100%. There is no limit to the pH that these formulations can take but pH values between 7 and 12 are preferred and between 8 and 10 most preferred.

Examples 4A-GG

Premium to Mid-Tier Laundry Detergent Formulas

The following prophetic formulas, in Table 4, are intended to cover liquid laundry detergent formulas. Unless more narrowly defined in the table, the pH of these formulas is between a pH of about 7 to about 10, preferably between about 7.5 to about 9.5 and most preferably between about 8.5 to about 9.0. These formulas are not intended to be limiting in any way—optional ingredients described herein regarding the present technology can be added in the proportions described. In each case, these are intended to be liquid detergent formulas and, after the addition of optional ingredients, water would be used to bring the total weight up to 100%.

TABLE 4

| Ingredient* | Generic Formula | A | B | C | D | E | F | G | H | I |
|---|---|---|---|---|---|---|---|---|---|---|
| | % Inclusion by Weight (Based on 100% Active) | | | | | | | | | |
| SE, PHSE, HSE | 2-90 | 23 | 23 | 5.6 | 23 | 23 | 21 | 29 | 29 | 38 |
| Nonionic surfactant | 2-40 | 14 | 14 | 14 | 14 | 14 | 12 | 16 | 16 | 18 |
| AES | 0-35 | | | 17.4 | | | | | | |
| C16MES | 0-25 | | | | | | | | | |
| Cocoamide DEA | 0-25 | | | | | | | | | |
| AMMONYX ® LO | 0-6 | | | | | | 2 | | | |
| C$_{12}$EO$_3$ | 0-6 | | | | | | 2 | | | |
| Coconut fatty acid | 0-10 | | | | | | | | | |
| Borax pentahydrate | 0-3 | 2.7 | 2.7 | 2.7 | | 2.7 | 2.7 | 2.2 | 2.2 | 1.5 |
| Propylene glycol | 0-6 | 2.6 | 2.6 | 2.6 | 4.0 | 2.6 | 2.6 | 2.1 | 2.1 | 1.4 |
| Calcium chloride | 0-2 | | | | 0.2 | | | | | |
| Glycerol | 0-6 | | | | | | | | | |
| Sodium citrate | 0-10 | 3.9 | 3.9 | 3.9 | 3.9 | 3.9 | 3.9 | 3.9 | 3.9 | 5.0 |
| Triethanolamine | 0-6 | | | | | | | | | |
| Monoethanolamine | 0-6 | 3.5 | 3.5 | 3.5 | 3.5 | 3.5 | 3.5 | 3.5 | 3.5 | 4.5 |
| Fluorescent whitening agent (FWA) | 0-1 | 0.15 | 0.15 | 0.15 | 0.15 | 0.15 | 0.15 | 0.15 | 0.15 | 0.2 |
| Anti-redeposition agent | 0-1.5 | | | | | 0.8 | 0.8 | | 0.8 | |
| Thickener | 0-2 | 0.25 | 0.25 | 0.15 | 0.2 | 0.2 | 0.2 | | | |
| Thinner | 0-20 | | | | | | | | | 1-3 |
| Protease | 0-2 | 0.8 | 0.8 | 0.8 | 0.8 | 0.8 | 0.8 | 0.8 | 0.8 | 1.1 |
| Amylase | 0-2 | 0.4 | 0.4 | 0.4 | 0.4 | 0.4 | 0.4 | 0.4 | 0.4 | 0.55 |
| Lipase | 0-2 | 0.2 | | | | | | | | |
| Mannanase | 0-2 | 0.1 | | | | | | | | |
| Cellulase | 0-2 | 0.02 | | | | | | | | |
| pH | | | | | | 7.0-7.5 | | | | |

| Ingredient* | J | K | L | M | N | O | P | Q | R |
|---|---|---|---|---|---|---|---|---|---|
| | % Inclusion by Weight (Based on 100% Active) | | | | | | | | |
| SE, PHSE, HSE | 38 | 38 | 38 | 46 | 46 | 46 | 6 | 11.4 | 6 |
| Nonionic surfactant | 11 | 18 | 11 | 24 | 14 | 14 | 10 | 10 | 10 |
| AES | | | | | | | 5.4 | | 5.4 |
| C16MES | | | | | | | | | |
| Cocoamide DEA | | | | | | | | | |
| AMMONYX ® LO | | | | | | | 1 | 1 | 1 |
| C$_{12}$EO$_3$ | 7 | | 7 | | 10 | 10 | | | |
| Coconut fatty acid | | | | | | | 1 | | 1 |
| Borax pentahydrate | 1.5 | 1.5 | 1.5 | | 0.5 | 0.5 | | 2.2 | |
| Propylene glycol | 1.4 | 1.4 | 1.4 | 3.0 | 1.0 | 1.0 | 2.1 | 2.1 | |
| Calcium chloride | | | | 0.1 | | | 0.15 | | |
| Glycerol | | | | | | | | | |
| Sodium citrate | 5.0 | 5.0 | 5.0 | 5.0 | 5.0 | 5.0 | 1.4 | 1.4 | 3.5 |
| Triethanolamine | | | | | | | 0.52 | 0.52 | 0.52 |
| Monoethanolamine | 4.5 | 4.5 | 4.5 | 4.5 | 4.5 | 4.5 | 0.53 | 0.53 | 0.53 |
| Fluorescent whitening agent (FWA) | 0.2 | 0.2 | 0.2 | 0.2 | 0.2 | 0.2 | 0.15 | 0.15 | 0.15 |
| Anti-redeposition agent | | | | | | | | | |
| Thickener | | | | | | | 0.15 | 0.25 | 0.15 |
| Thinner | | 1-3 | | 3-7 | | 2-5 | | | |
| Protease | 1.1 | 1.1 | 1.1 | 1.2 | 1.2 | 1.2 | 0.6 | 0.6 | |
| Amylase | 0.55 | 0.55 | 0.55 | 0.6 | 0.6 | 0.6 | 0.3 | 0.3 | |
| Lipase | | 0.25 | 0.25 | | | | | | |
| Mannanase | | 0.13 | 0.13 | | | | | | |
| Cellulase | | 0.02 | 0.02 | | | | | | |
| pH | 7.0-7.5 | | | | | | | | |

| Ingredient* | S | T | U | V | W | X | Y | Z | AA |
|---|---|---|---|---|---|---|---|---|---|
| | % Inclusion by Weight (Based on 100% Active) | | | | | | | | |
| SE, PHSE, HSE | 11.4 | 11.4 | 29 | 38 | 38 | 46 | 6.4 | 12.4 | 12.4 |
| Nonionic surfactant | 10 | 10 | 16 | 18 | 11 | 14 | | | |
| AES | | | | | | | 6 | | |
| C16MES | | | | | | | 4 | 4 | 4 |
| Cocoamide DEA | | | | | | | 9.8 | 9.8 | 9.8 |
| AMMONYX ® LO | | 1 | | | | | | | |
| C$_{12}$EO$_3$ | | | | | 7 | 10 | | | |
| Coconut fatty acid | | | | | | | | | |

TABLE 4-continued

| Ingredient | 1 | 2 | 3 | 4 | 5 | 6 | 7 | 8 | 9 |
|---|---|---|---|---|---|---|---|---|---|
| Borax pentahydrate | | | | | | | 1.7 | 1.7 | |
| Propylene glycol | | | | | | | | | |
| Calcium chloride | | | | | | | | | 0.15 |
| Glycerol | | | | | | | 4.6 | 4.6 | 5.5 |
| Sodium citrate | 3.5 | 3.5 | 3.9 | 5.0 | 5.0 | 5.0 | | | |
| Triethanolamine | 0.52 | 0.52 | | | | | | | |
| Monoethanolamine | 0.53 | 0.53 | 3.5 | 4.5 | 4.5 | 4.5 | | | |
| Fluorescent whitening agent (FWA) | 0.15 | 0.15 | 0.15 | 0.2 | 0.2 | 0.2 | 0.15 | 0.15 | 0.15 |
| Anti-redeposition agent | | | | | | | | | |
| Thickener | 0.25 | 0.25 | | | | | 0.1 | 0.25 | 0.25 |
| Thinner | | | | 1-3 | | | | | |
| Protease | | | | | | | 0.6 | 0.6 | 0.6 |
| Amylase | | | | | | | 0.3 | 0.3 | 0.3 |
| Lipase | | | | | | | | | |
| Mannanase | | | | | | | | | |
| Cellulase | | | | | | | | | |
| pH | | | | | | | | | |

| | % Inclusion by Weight (Based on 100% Active) | | | | |
|---|---|---|---|---|---|
| Ingredient* | BB | CC | DD | EE | FF |
| SE, PHSE, HSE | 10.4 | 25 | 27 | 25 | 27 |
| Nonionic surfactant | | | | | |
| AES | | | | | |
| C16MES | 4 | 11 | 11 | 11 | 11 |
| Cocoamide DEA | 9.8 | 17 | 17 | 10 | 10 |
| AMMONYX ® LO | 2 | 2 | | 2 | |
| $C_{12}EO_3$ | | | | 7 | 7 |
| Coconut fatty acid | | | | | |
| Borax pentahydrate | 1.7 | 1.2 | 1.2 | 1.2 | 1.2 |
| Propylene glycol | | | | | |
| Calcium chloride | | | | | |
| Glycerol | 4.6 | 3 | 3 | 3 | 3 |
| Sodium citrate | | | | | |
| Triethanolamine | | | | | |
| Monoethanolamine | | | | | |
| Fluorescent whitening agent (FWA) | 0.15 | 0.15 | 0.2 | 0.2 | 0.2 |
| Anti-redeposition agent | | | | | |
| Thickener | 0.25 | | | | |
| Thinner | | | | | |
| Protease | 0.6 | 1 | 1 | 1 | 1 |
| Amylase | 0.3 | 0.5 | 0.5 | 0.5 | 0.5 |
| Lipase | 0.2 | | | | |
| Mannanase | 0.1 | | | | |
| Cellulase | 0.02 | | | | |
| pH | | | | | |

*A preferred nonionic surfactant is BIO-SOFT ® N25-7, Stepan Company. A preferred AES is STEOL ® CS-460, Stepan Company. A preferred FWA is TINOPAL CBS-X, Ciba. A preferred thickener is Cellosize QP100MH, Dow. Preferred thinners include: $C_{12}EO_2$, $C_{12}EO_3$ (in addition to that already included in certain formulas in the table), ethanol, isopropanol, sodium xylene sulfonate, sodium cumene sulfonate, 2-methoxy ethanol, 2-butoxyethanol, methoxy ethoxy ethanol and combinations of these. A preferred preservative for these formula is Neolone M-10 from Rohm and Haas used at 75 ppm on 100% active basis.

Examples 5A-D

Example 5A

In 100 ml of 65° F. tap water with a 1" magnetic stirrer on a Corning magnetic stir plate set at 3.5, 2 ml of Comparative Formula 1 from Example 33 in PCT Application Serial No. PCT/US09/31455 was quickly added to the mixing water from a pipette. It took 14 seconds before all the swirls from dissolving HDL were gone and the solution was clear while for the SHP HDL (Formula A from Example 33), it took three seconds. This example demonstrates that the HDL formulated with SHP dissolves into solution much faster than the analogous HDL formulated with AES/LAS as the anionic surfactant.

Example 5B

For Comparative Formula 1 in Example 33 in PCT Application Serial No. PCT/US09/31455, heat was added during the batching to facilitate solubilization of certain ingredients and thereby reduce batch cycle time. With Formula A in Example 33 in PCT Application Serial No. PCT/US09/31455, no added heat was needed to speed up batching. This simplified processing route demonstrates that SHP-based HDLs can be made in comparable time to LAS/AES-based HDLs while using less energy Example 5C A leading liquid laundry detergent was purchased and the water driven off in an oven yielding a solids level of 24.4%. Based on this, an analogous SHP-containing HDL was produced in the lab (SHP from Example 2 in PCT Application Serial No. PCT/US09/31455 was used) wherein the anionic active of the commercial HDL, analyzed to be 12% by titration and gas chromatography, was matched in a SHP HDL. Other ingredients in the commercial formula were also added in analyzed proportions to bring the SHP HDL to 24.4% solids. Each HDL was then used to wash 6 pounds of 65%/35% cotton/polyester pillowcases and four of each of the following soiled swatches—dust/sebum on cotton, red wine, clay, EMPA 116—in a Whirlpool Duet Sport washing machine with 100 F wash water, 60 g of detergent. The washed clothes were each then sent through 3 rinse cycles. Rinse water from the second and third rinse cycles were collected and visually inspected. For the commercial HDL, the rinse water for both the second and third rinses was visually hazy while that for the analogous SHP HDL was perfectly clear to the eye. This example demonstrates that SHP-based HDLs rinse away off of laundered clothes, and are therefore less likely to leave residues, more easily than HDLs based on LAS/AES.

Example 5D

This example, Table 5, lists prophetic softergent formulas:

TABLE 5

| Ingredient | % Inclusion by Weight (Based on 100% Active) | | | | | | |
|---|---|---|---|---|---|---|---|
| | A | B | C | D | E | F | H |
| SE, PHSE, HSE | 23.0 | 46.0 | 15.0 | 11.0 | 45.0 | 11.0 | 45.0 |
| Nonionic surfactant | 14.0 | 24.0 | | 9.0 | 30.0 | 9.0 | |
| C16MES | | | 7.0 | | | | |
| Cocoamide DEA | | | 14.0 | | | | |
| Borax pentahydrate | 2.7 | 1.2 | 1.7 | | | | |
| Propylene glycol | 2.6 | 1.8 | | | | | |
| Glycerol | | | 4.6 | | | | |
| Sodium citrate | 3.9 | 5.0 | | | | | |
| Triethanolamine | | | | | | | |
| Sodium carbonate | | | | 3 | 6 | | |
| Sodium metasilicate | | | | | | 3 | 6 |
| Monoethanolamine | 3.5 | 4.5 | | | | | |
| Fluorescent whitening agent (FWA) | 0.15 | 0.2 | 0.15 | 0.15 | 0.2 | 0.15 | 0.2 |
| Thickener | 0.25 | | 0-0.2 | 0.3 | | | |
| Thinner | | 3-7 | | | 2-8 | | 2-8 |
| Protease | 0-1.5 | 0-1.5 | 0-1.5 | | | | |
| Amylase | 0-0.8 | 0-0.8 | 0-0.8 | | | | |
| Lipase | 0-0.5 | 0-0.5 | 0-0.5 | | | | |
| Mannanase | 0-0.3 | 0-0.3 | 0-0.3 | | | | |
| Cellulase | 0-0.2 | 0-0.2 | 0-0.2 | | | | |
| Softener | | | | 0.3-10 | | | |
| pH | | 7-10 | | | 10-12.5 | | |

After ingredients are added, water is added to bring the percent up to 100%. Preferred softening agents include: Accosoft 365 (tallow polyethoxy ammonium methylsulfate), Ammonyx Cetac (cetyl trimethyammonium chloride) from Stepan Company; Polyquaterium 10/soap mixtures and monoalkyl quat/soap mixtures.

The formulations shown in the above table are just some examples of the types of softergents that can be created within the scope of the presently described technology. Similar such softergents can also be created by adding appropriate softening molecules and amounts to the formulations detailed in Examples 32 and 33 in PCT Application Serial No. PCT/US09/31455.

Example 6

Sulfo-Estolide and Hydrolyzed Sulfo-Estolides

The sulfonated estolides used in several of the following examples are designated SE and HSE and were prepared in accordance with the procedures described in this example. SE was produced from 100% Oleic acid feed stock. The final product was the result of neutralization with KOH, hydrolysis, and bleaching (using 1.1% by weight of 50% H2O2 per acid flow). The final product consisted of 71.37% solids at a pH of 5.02 with a % K2SO4 of 2.41.

The feedstock used for SE production had an equivalent weight of about 275.06 and was comprised of about 78% C-18:1, about 12% C-18:2, and about 9% saturated fatty acids. The feedstock was sulfonated on a falling film reactor at a rate of about 129.3 lbs per hour using a molar ratio of $SO_3$ to alkene functionality of about 0.95. The SE sulfonic acid was continuously neutralized in a loop reactor with concurrent addition of about 49.1 lbs per hour of 45% aqueous KOH and about 37.9 lbs per hour of water. The temperature of the reaction mixture in the loop reactor was about 80° C. Neutralized SE solution was continuously fed from the loop reactor to an in-line mixer, where about 2.61 lbs per hour of 50% aqueous hydrogen peroxide was homogenized into the solution, which was about pH 5.8. This reaction mixture was then fed to a stirred tank reactor. After collecting about 60 gallons of reaction mixture, concurrent sultone hydrolysis and bleaching were continued at about 80° C. for about 4 additional hours. At the end of this 4 hour hydrolysis and bleaching period about 16.5 lbs of 38% sodium bisulfite solution was added to the reaction mixture to reduce the residual peroxide in solution from about 0.25% (wt/wt) active peroxide down to about 0.02% (wt/wt) active peroxide. The SE produced from this reaction was at a pH of about 5.0, was comprised of about 69.8% solids and about 0.017% (wt/wt) active peroxide, and had a Klett color at 1 percent solids concentration of 51. Utilizing the titration method described in Example 2 the carboxylic ester was determined to be about 40.8 mol percent.

SE was then used as the starting material to produce HSE in the following manner. To a quart (1-liter) jar was added about 528 g of SE produced in the preceding paragraph, and about 107.03 g of 45 wt. % aqueous KOH, which corresponded to a molar amount of KOH necessary to: (a) neutralized all free carboxylic acids in the SE; and (b) to hydrolyzed the carboxylic esters in the SE with 1.05 molar equivalents of free caustic. To this was also added about 144.15 g of water and the contents were thoroughly mixed and then the jar was sealed and placed in an approximately 85° C. oven for about 18 hours. Upon cooling, the obtained HSE was homogeneous, free of precipitation or solids, and was a highly flowable liquid. The HSE was analyzed by titration with aqueous HCl and was found to comprise about 1.66 meq/g of potassium carboxylate. Based on the mass balance from the reagent charges for the ester hydrolysis reaction and the change in carboxylate content, the degree of ester hydrolysis was calculated to be about 98.2 mol percent. At this level of ester hydrolysis, the carboxylic ester content in the HSE was calculated to about 0.7 mol percent of total carboxylic functionality in the HSE.

Example 7

Heavy Duty Liquid Laundry Detergent Formulations

This example describes a study of the effect of a heavy duty liquid laundry detergent formula on soil removal. More particularly, the effect of the addition of magnesium ion as magnesium sulfate in laundry (heavy duty liquid) formulas that contain SE and MES (methyl ester sulfonate) is tested. The formula included MES as secondary surfactant in HDL-SE formulas that contain magnesium sulfate or antiredeposition polymer as additives. The evaluation was at pH 8.25, which allows to cover a premium tier and the MES is stable.

Table 6 sets forth the components of the HDL formula used in the study. SE was prepared according to Example 6. The formula had no additives and 2% actives of ALPHA-STEP® P-65 (alpha sulfo methyl ester (palm stearin), available from Stepan) as a reference. BioSoft® N25-7 is an alcohol ethoxylate having an HLB of 12.2 available from Stepan. Addition of magnesium sulfate range from 0 to 2% by wt. or antiredeposition polymer in a range from 0 to 1% by wt.

TABLE 6

| Component | (%) actives | (%) wt as is | Function |
|---|---|---|---|
| SE (68.96%) | 15 | 21.75 | Anionic surfactant |
| ALPHA -STEP P-65 (70%) | 2 | 2.86 | Secondary anionic surfactant |
| BIO-SOFT ® N25-7 (100%) | 5 | 5.00 | Nonionic surfactant |
| Sodium citrate dihydrate | | 1.00 | Builder, buffer |
| Monoethanolamine | | 1.00 | Builder |
| Triethanolamine | | 1.00 | Builder |
| Magnesium Sulfate anhydrous | | 0 to 2 | Additive |
| Antiredeposition polymer | | 0 to 1 | Additive |
| Neolone M10 | | 0.06 | Preservative |
| DI water | | up to 100 | Vehicle |
| pH (as is) 25° C. | | 8.25 | |

The formulation was made by the following manufacturing procedure. For each component, the mixture was subject to continuous agitation and waiting until complete dissolution of the raw materials before adding the next component. First SE was added to the water. Then magnesium sulfate was added, followed by BIO-SOFT N25-7 previously melted, and then sodium citrate. The solution was heated up to 60° C., then the ALPHA STEP P65 was added. The solution was mixed until it was completely melted. The solution was cooled to room temperature (25° C.), then monoethanolamine and triethanolamine were added, followed by the antiredeposition polymer and then Neolone M10. The pH (as is) was adjusted as required, using sodium hydroxide or sulfuric acid, as needed.

The formulation was tested according to ASTM D3050-07, which is a standard guide for measuring soil removal from artificially soiled fabrics. The test employed a high efficiency laundry machine. Temperature: 90° F. Ballast: 61b. The test evaluated different types of soils, including Hydrophobic soils: DSC (dust sebum cotton), GC (grass cotton), EMPA 106 (carbon black/mineral oil cotton), WFK 10C (wool fat kaolin cotton).

Table 7 shows the particular formulations tested (with varying amounts of magnesium sulfate and antiredeposition polymer), along with the percent removal of various soils (% SRI). The formulations were used with no other additives (other than magnesium sulfate or antiredeposition polymer in Formulas B through E), and evaluated at a pH 8.25.

TABLE 7

| | A | B | C | D | E |
|---|---|---|---|---|---|
| MgSO$_4$ (% wt) | 0 | 1 | 2 | 0 | 0 |
| Polymer (% wt) | 0 | 0 | 0 | 0.5 | 1 |
| | % SRI | % SRI | % SRI | % SRI | % SRI |
| DSC | 81.94 | 82.53 | 82.89 | 82.48 | 82.98 |
| GC | 79.81 | 80.68 | 79.87 | 78.98 | 79.37 |
| EMPA 106 | 67.47 | 68.32 | 68.61 | 68.69 | 68.91 |
| WFK 10C | 84.31 | 84.72 | 85.23 | 85.01 | 85.55 |

These results show that it is feasible to add MES as secondary surfactant to an HDL SE formula. The HDL SE formula with 2% actives of ALPHA-STEP P-65 at pH 8.25, showed improvement on % soil removal for the EMPA 106 soil in the presence of 0.5% and 1% antiredeposition agent and 2% magnesium sulfate. Other improvements are reflected in Table 7.

This study also evaluated viscosity. MES is a viscosity depressor. Laboratory results showed that even in the presence of MES, the addition of magnesium ion still increases slightly the viscosity of an HDL SE formula at pH 8.25. The viscosity of the various formulations was measured at a temperature of 25° C. with a Brookfield model RVT viscometer, spindle RVT-02, at 50 rpm. Table 8 shows the viscosity measured for formulas according to Table 7 having various concentrations of magnesium sulfate and without antiredeposition polymer.

TABLE 8

| % MgSO$_4$ (wt) | Viscosity (cps)25° C. |
|---|---|
| 0.00 | 31.2 |
| 0.25 | 28.8 |
| 0.50 | 56 |
| 1.00 | 52.8 |
| 2.00 | 20.8 |

These results demonstrate that magnesium sulfate is an effective viscosity modifier for laundry detergent formulations comprising sulfo-estolides and alkyl ester sulfonates. For some embodiments, a higher viscosity is desirable, and addition of 0.5% and 1.0% by weight magnesium sulfate provided a increase in viscosity.

Example 8

Heavy Duty Liquid Laundry Detergent Formulations

This example, Table 9, lists prophetic heavy duty liquid laundry detergent formulas. Generally the pH of these formulas is between pH 7 and 10, preferably between 7.5 and 9.5 and most preferably between 8.5 and 9.0. In each case, these are intended to be liquid detergent formulas and, after the addition of optional ingredients, water would be used to bring the total weight up to 100%. The ingredients are listed on a "100% Active" basis, meaning that the listed weight percentage is not diluted but rather 100% of the ingredient.

TABLE 9

| Ingredients* | Generic formula | % Inclusion by Weight (Based on 100% Active) Continued | | | | | | | | |
|---|---|---|---|---|---|---|---|---|---|---|
| | | A | B | C | D | E | F | G | E | F |
| Potassium SE | 2-90 | 2.2 | 5 | 4.2 | 4.2 | 10 | 11 | 10 | 11 | 14 |
| Sodium SE | combined total | 3.8 | 7.4 | 6.2 | 6.2 | 15 | 16 | 15 | 16 | 21 |
| AES | 0-20 | 6 | | | | | | | | |
| C16MES | 2-25 | 4 | 4 | 4 | 4 | 11 | 11 | 11 | 11 | 13 |
| Cocoamide DEA | 0-25 | 9.8 | 9.8 | 9.8 | 9.8 | 17 | 17 | 10 | 10 | 12 |
| AMMONYX ® LO | 0-6 | | | 2 | 2 | 2 | | 2 | | |
| $C_{12}EO_3$ | 0-10 | | | | | | | 7 | 7 | 10 |
| Borax pentahydrate | 0-3 | 1.7 | 1.7 | 1.7 | 1.7 | 1.2 | 1.2 | 1.2 | 1.2 | 1.2 |
| Glycerol | | 4.6 | 4.6 | 4.6 | 4.6 | 3 | 3 | 3 | 3 | 3 |
| Fluorescent whitening agent (FWA) | 0-1 | 0.15 | 0.15 | 0.15 | 0.15 | 0.15 | 0.2 | 0.2 | 0.2 | 0.2 |
| Thickener | 0-2 | 0.1 | 0.25 | 0.25 | 0.25 | | | | | |
| Protease | 0-2 | 0.6 | 0.6 | 0.6 | 0.6 | 1 | 1 | 1 | 1 | 1 |
| Amylase | 0-2 | 0.3 | 0.3 | 0.3 | 0.3 | 0.5 | 0.5 | 0.5 | 0.5 | 0.5 |
| Lipase | 0-2 | | | | 0.2 | | | | | |
| Mannanase | 0-2 | | | | 0.1 | | | | | |
| Cellulase | 0-2 | | | | 0.02 | | | | | |

*A preferred alcohol ether sulfate is sodium laureth sulfate, available as STEOL ® CS-460 from Stepan Company. A preferred FWA is TINOPAL CBS-X (Ciba). A preferred thickener is high molecular weight hydroxyethylcellulos, such as Cellosize QP 100MH (Dow). Preferred high molecular weight hydroxyethylcelluloses include those having a molecular weight of at least about 100,000, alternatively at least about 300,000, alternatively at least about 500,000. A preferred preservative for these formulas is Neolone M-10 (Rohm and Haas), a formaldehyde-free biocidal solution, used at 75 ppm on a 100% active basis.

These formulas are not intended to be limiting in any way, and optional ingredients described in this specification can be added in the proportions described.

Example 9

Light Duty Liquid Laundry Detergent Formulations

Tables 10A and 10B present light duty liquid (LDL) laundry detergent formulas that contain an alkyl ester sulfonate, namely sodium methyl-2 sulfo C12-C18 ester (provided in ALPHA-STEP PC-48, available from Stepan Company, Northfield, Ill.). One formulation (Formula 10B) also includes a sulfo-estolide surfactant of the present technology which produces desirable viscosity characteristics with the desired cleaning capabilities. This sulfo-estolide was made in accordance with Example 6 above. The formulations also included sodium lauryl sulfate (STEPANOL WA-EXTRA K, also available from Stepan), magnesium sulfate, and demonized water. Formula 10B also included SE, a sulfonated estolide potassium salt produced from 100% Oleic acid feed stock.

For each component, "% Active RM" indicates the percents of active material in the feedstock, "Formula % Active" indicates the weight percent of the active material in the liquid detergent formulation, and "Wt. Needed" and "Wt. Added" (both in grams) indicate the calculated and actually weighed amounts added to a formulation having a total weight of 100.00 grams. Each of these formulations are intended to be liquid detergent formulas and it is contemplated that additional optional components may be added. After the addition of such components, water would be used to bring the total weight up to 100%.

TABLE 10A

Formula 10A
No SE

| Component | Lot # | order | % Active RM | Formula % Active | Wt. Needed | Wt. Added |
|---|---|---|---|---|---|---|
| DI Water | NA | 1 | 100.00 | — | 20.04 | 20.07 |
| SE | | 3 | 68.00 | 0.00 | 0.00 | 0.00 |
| Stepanol WA-Extra K | 7297969 | 5 | 30.00 | 15.00 | 50.00 | 50.04 |
| Amphosol CA | 7342620 | 6 | 30.73 | 5.00 | 16.27 | 16.27 |
| Alpha-Step PC-48 | 7239754 | 4 | 39.40 | 5.00 | 12.69 | 12.71 |
| MgSO4 | 41129127 | 2 | 100.00 | 1.00 | 1.00 | 1.00 |
| | | | | Total | 100.00 | |

TABLE 10B

Formula 10B
With SE

| Component | Lot # | order | % Active RM | Formula % Active | Wt. Needed (gms) | Wt. Added |
|---|---|---|---|---|---|---|
| DI Water | NA | 1 | 100.00 | — | 12.69 | 12.70 |
| SE (potassium) |  | 3 | 68.00 | 5.00 | 7.35 | 7.35 |
| Stepanol WA-Extra K | 7297969 | 5 | 30.00 | 15.00 | 50.00 | 50.10 |
| Amphosol CA | 7342620 | 6 | 30.73 | 5.00 | 16.27 | 16.25 |
| Alpha-Step PC-48 | 7239754 | 4 | 39.40 | 5.00 | 12.69 | 12.71 |
| MgSO4 | 41129127 | 2 | 100.00 | 1.00 | 1.00 | 1.00 |
|  |  |  |  | Total | 100.00 |  |

In the preparation of Formula A, upon the addition of cocamidopropyl betaine (AMPHOSOL CA, available from Stepan), a hazy bubble gel mass formed, which cleared with centrifuging at 2000 rpm. The viscosity of the present formulations was measured at a temperature of 25° C. with a Brookfield model RVT viscometer at 20 rpm. Formula 10A was measured using spindle 4, and Formula 10B was measured using spindle 3. The viscosity of the Formula A without SE was 14,613 cps and was a clear viscous gel. The viscosity of Formula B containing SE was 2,784 cps. Thus, addition of the SE of the present technology provides a 5-fold decrease in the viscosity of the formulation, allowing previously unusable formulations to be usable in a pourable liquid.

The ability of the formulations to foam was tested using a foam mileage procedure using Crisco vegetable shortening. For comparison, a commercially available light duty liquid detergent (ULTRA JOY) was also tested. A 0.1% solution of the LDL is prepared in 500 grams total using 140 ppm hardness tap water initially at 50 degrees Centigrade. This wash bath is agitated with a KitchenAid mixer at a setting of 6, producing copious initial foam. Crisco shortening is titrated into the wash solution at a rate of no more than 0.5 grams per minute with a syringe. As the soil is introduced, the foam eventually collapses. The amount of Crisco tolerated prior to foam collapse is the foam mileage for the formula. This simulates soil being introduced from the washing of dirty plates, and measures how many plates could be washed before the foam is gone. The results of the foam mileage test are shown in Table 11, wherein the addition of the SE increases the foam mileage of the formulation.

TABLE 11

| Product | % Solution | Rep | Run # | Wt (start) | Wt (end) | Soil wt | Average |
|---|---|---|---|---|---|---|---|
| Formula A | 0.1000 | 1 | 1 | 12.32 | 10.38 | 1.94 | 1.81 |
|  |  | 2 | 4 | 13.82 | 12.14 | 1.68 |  |
| Formula B | 0.1000 | 1 | 2 | 17.82 | 15.54 | 2.28 | 2.15 |
|  |  | 2 | 5 | 12.14 | 10.12 | 2.02 |  |
| Ultra Joy | 0.1000 | 1 | 3 | 15.54 | 13.82 | 1.72 | 1.67 |
|  |  | 2 | 6 | 10.13 | 8.52 | 1.61 |  |

Table 11 shows that Formula B had superior foam mileage to Formula A and to Ultra Joy. It was contemplated that increasing the surfactant actives from 20 to 25 would result in an increase in foam mileage, and the use of sulfo-estolide in the light duty liquid detergent accomplished this. The sulfo-estolide allows more surfactant to be added than would otherwise be possible to provide a clear liquid composition that performs as expected with the increased levels of surfactant total. Table 11 also shows that the benefit of SE extends down to the lower total actives formulations.

Example 10

Premium to Mid-Tier Laundry Detergent Formulations

The following prophetic formulas, in Table 12, are intended to cover liquid laundry detergent formulas. Unless more narrowly defined in the table, the pH of these formulas is between a pH of about 7 to about 10, preferably between about 7.5 to about 9.5 and most preferably between about 8.5 to about 9.0. These formulas are not intended to be limiting in any way—optional ingredients described herein regarding the present technology can be added in the proportions described. In each case, these are intended to be liquid detergent formulas and, after the addition of optional ingredients, water would be used to bring the total weight up to 100%.

TABLE 12

| Ingredient* | % Inclusion by Weight (Based on 100% Active) |
|---|---|
| SE, PHSE, HSE | 2-90 |
| Magnesium sulfate | 0-3 |
| Nonionic surfactant | 2-40 |
| AES | 0-35 |
| C12-C18 MES blend | 0.1-25 |
| Cocoamide DEA | 0-25 |
| AMMONYX ® LO | 0-6 |
| $C_{12}EO_3$ | 0-6 |
| Coconut fatty acid | 0-10 |
| Borax pentahydrate | 0-3 |
| SE, PHSE, HSE | 2-90 |
| Magnesium sulfate | 0-3 |
| Propylene glycol | 0-6 |
| Calcium chloride | 0-2 |
| Glycerol | 0-6 |
| Sodium citrate | 0-10 |
| Triethanolamine | 0-6 |
| Monoethanolamine | 0-6 |
| Fluorescent whitening agent (FWA) | 0-1 |
| Anti-redeposition agent | 0-1.5 |
| Thickener | 0-2 |
| Thinner | 0-20 |
| Protease | 0-2 |
| Amylase | 0-2 |
| Lipase | 0-2 |
| Mannanase | 0-2 |

TABLE 12-continued

| Ingredient* | % Inclusion by Weight (Based on 100% Active) |
|---|---|
| Cellulase | 0-2 |
| pH | 7.0-10.0 |

*A preferred nonionic surfactant is BIO-SOFT ® N25-7, Stepan Company. A preferred AES is STEOL ®CS-460, Stepan Company. A preferred lauryl myristal amidopropyl dimethyl amine oxide is AMMONYX LO. A preferred FWA is TINOPAL CBS-X, Ciba. A preferred thickener is Cellosize QP 100MH, Dow. Preferred thinners include: $C_{12}EO_2$, $C_{12}EO_3$ (in addition to that already included in certain formulas in the table), ethanol, isopropanol, sodium xylene sulfonate, sodium cumene sulfonate, 2-methoxy ethanol, 2-butoxyethanol, methoxy ethoxy ethanol and combinations of these. A preferred preservative for these formulas is Neolone M-10 from Rohm and Haas used at 75 ppm on a 100% active basis.

Example 11

Green Laundry Detergent Formulations

As petroleum reserves continue to dwindle, it is becoming increasingly important to have effective laundry detergents based on bio-renewable sources. Bio-renewable sources include both animal and plant based feedstocks, although plant-based ones are preferred. Bio-renewable Carbon Index (BCI) is defined for a given ingredient as:

$BCI$=100×(the number of bio-renewable carbon atoms in the molecule/the total number of carbon atoms in the molecule)

The following Table 13 details several prophetic core surfactant formulas wherein the BCI for the overall core formula is 100:

TABLE 13

| Ingredient* | % Inclusion by Weight (Based on 100% Active) |
|---|---|
| SE, PHSE, HSE | 2-90 |
| Magnesium sulfate | 0-3 |
| C16 methyl ester sulfonate | 0-30 |
| C12 methyl ester sulfonate | 0-30 |
| blend C12-C18 methyl ester sulfonate | 0-30 |
| C12-C18 methyl ester sulfonate blend | 0-30 |
| Sodium lauryl sulfate | 0-30 |
| Sodium coco sulfate | 0-30 |
| Sodium stearoyl lactylate | 0-30 |
| Sodium lauroyl lactate | 0-30 |
| alkyl polyglucoside (APG) | 0-60 |
| Polyglycerol monoalkylate | 0-60 |
| Lauryl lactyl lactate | 0-30 |
| Saponin | 0-30 |
| Rhamnolipid | 0-30 |
| Sphingolipid | 0-30 |
| Glycolipid | 0-30 |
| Abietic acid derivative | 0-30 |
| Polypeptide | 0-30 |

*For the methyl ester sulfonates, the methanol from which the ester is made is from bio-renewable sources. APGs of varying HLB values are available from Henkel - a preferred APG is Glucopon 425N. A preferred polyglycerol monoalkylate is triglycerol monolaurate as described in Kato, et al., *Journal of Surfactants and Detergents*, October, 2003, Vol. 6, Number 4, pg. 331. Tea saponin is available from Shanghai Greenway. Quillaja saponin is available from Sigma Chemical Co. More details of many of these surfactants are described in *Surfactant Science Series*, Marcel Dekker, Vols. 25 and 48, incorporated herein by reference.

Example 12

Liquid Personal Cleansing Compositions

This example provides personal care compositions. The following formulation in Table 14 demonstrated the use of SE in a personal care cleansing product. SE was prepared in accordance with Example 6. ALPHA-STEP® PC-48 (Sodium Methyl 2-Sulfolaurate (and) Disodium 2-Sulfolaurate) and AMPHOSOL® HCG (Cocamidopropyl Betaine) are available from Stepan Company, Northfield, Ill.

TABLE 14

| | Formluation A Wt % Active |
|---|---|
| SE | 6 |
| ALPHA-STEP PC-48 | 6 |
| STEOL CS-230 | — |
| AMPHOSOL HCG | 3 |
| Citric acid (25%) | q.s. |
| NaCl | 0 |
| Water | q.s. to 100 |
| Total active % | 15 |
| Appearance | Clear liquid |
| pH | 5.57 |
| Viscosity (cps) | 1 |
| Foam Volume at 0.2% active with 2% castor oil (ml) | 173 |
| Foam Volume at 0.2% active, no oil (ml) | 230 |

Formulation A exhibited good foam volume characteristics, both in the presence and absence of castor oil.

Example 13

Sulfate-Free Personal Care Formulation

This example provides sulfate-free personal care cleaning compositions. Table 15 contains personal care compositions containing the sulfo-estolide of the present technology. SE and HSE were prepared in accordance with Example 6. ALPHA-STEP PC-48 is a surfactant combination of sulfonated methyl esters and sulfonated fatty acids 7:11, and AMPHOSOL HCG is a cocamidopropyl betaine, both of which can be obtained from Stepan Company, Northfield Ill. In two formulations, the sulfo-estolide was added in addition to the surfactants, while in two other formulations, the sulfo-estolide was added to replace a percentage of the surfactant to test the ability of the sulfo-estolide to replace the properties of the surfactant.

TABLE 15

| | Control A % wt active | Example B % wt active | Example C % wt active | Example D % wt active | Example E % wt active |
|---|---|---|---|---|---|
| D.I. water | Up to 100% | Up to 100% | Up to 100% | Up to 100% | Up to 100% |
| Alpha-Step PC-48 | 12 | 12 | 10.4 | 10.4 | 10.4 |
| Amphosol HCG | 3 | 3 | 3 | 2.6 | 2.6 |
| SE: | 0 | 2 | 0 | 2 | 0 |

TABLE 15-continued

|  | Control A<br>% wt active | Example B<br>% wt active | Example C<br>% wt active | Example D<br>% wt active | Example E<br>% wt active |
|---|---|---|---|---|---|
| HSE: | 0 | 0 | 2 | 0 | 2 |
| Total Active surfactant (%) | 15 | 17 | 17 | 7 | 15 |

Thus, the formulations contain the sulfo-estolide as an additional component or in partial replacement of the second surfactant. These formulations were tested by a hand wash test of 3 panelists to test for the average foam volume produced. The results of the foam volume of the formulations are in Table 16 below.

Three panelists with different skin types were chosen for each test. The skin types of the panelist were determined using a NOVA meter. A NOVA reading between 100-110 represents dry skin, 115-120 normal skin and 130-140 moist (oily) skin. The panelists were asked to assess the performance of the experimental product and the control with 1 being the worst and 5 being the best. The difference between the sample and control was calculated. The average score from three panelists was taken to assess the directional performance between the experimental product and control.

The hand washing tests were conducted using luke-warm (95° C. and 105° F.) Chicago tap water. 1 ml of the 15% active liquid composition was dispensed to the panelist's wet palm. The hand washing procedure was as follows:
1. Panelists were asked to pre-wash their hands to remove residue from the skin and establish a baseline before evaluating the experimental liquid cleaning products.
2. Hand washing tests were conducted using luke-warm (95° C. and 105° F.) running tap water.
3. 1 ml of test product was dispensed into the panelist's wet palm.
4. The panelists were asked to wash their hands by gently rubbing them together for 30 seconds.
5. The panelists were instructed to rinse their hands under running tap water for 15 seconds.
6. The washing procedures of steps 3-4 were repeated and the foam generated was collected and measured using a graduated beaker prior to rinsing.
7. Panelist dried their hands with a paper towel followed by air drying.

The panelists were asked to rank the product behavior on a 5-point scale (5 being desirable, 1 being undesirable), for the following attributes: wet feel (how the product feels on wet hands characterized by slippery and smooth quality); foaming (quantity of foam generated); rinsability (how much effort is required to rinse product from the skin); tackiness during drying (sticky/tacky feeling during the drying process); skin tightness when dry; skin dryness (after completely dry).

The measured volume in ml is indicated in each of the bubbles shown in Table 16 below.

TABLE 16

| Formula | Foam Height, mL |
|---|---|
| Control A | 108 |
| Example B | 158 |
| Example C | 190 |
| Example D | 190 |
| Example E | 200 |

The formulations have similar softness and moisturization but the volume of foam for the formulations containing the sulfo-estolide of the present technology were greater as compared with the control. These formulations have superior foaming capabilities than the control, with providing equivalent softness and moisturization. These formulations can be used to decrease the amount of surfactants in personal care compositions which would decrease production cost and create cost-effective formulations.

Example 14

Automatic Dishwasher Detergent Formulation

Automatic dishwasher (ADW) detergent compositions were prepared and tested as follows. Table 17 contains a phosphate free, chlorine free, enzyme based formula, low pH ADW formulation containing the sulfo-estolide of the present technology and alkyl ester sulfonate. ALPHA-STEP PC-48 is a surfactant combination of sulfonated methyl esters and sulfonated fatty acids 7:11 which can be obtained from Stepan Company, Northfield Ill. This example shows that the pH can be lowered to an acceptable range for the enzymes include in an ADW formulation, such as a pH below 11, preferably a pH in the range of about 10 to about 10.5.

TABLE 17

| Ingredient | (%) add as is | actual weight | (%) actives in raw mtl | (%) active in ADW | Lot # | Order of addition |
|---|---|---|---|---|---|---|
| DI Water | 46.35 | 152.86 | 0.00 | 0.00 |  | 1 |
| SLA HOPA | 8.00 | 24.71 | 50.00 | 4.00 |  | 5 |
| Alpha-Step MC-48 | 2.73 | 8.15 | 36.62 | 1.00 | 7325190 | 6 |
| Sodium silicate | 12.00 | 35.98 | 100.00 | 12.00 | 060179 Fisher | 3 |
| Sodium citrate dehydrate | 15.00 | 44.99 | 100.00 | 15.00 | 080291 Fisher | 2 |
| Properase 1600L | 2.00 | 5.99 | 100.00 | 2.00 | Genecor | 8 |
| Purastar ST 15000L | 2.00 | 6.03 | 100.00 | 2.00 | Genecor | 9 |
| 37.5% HCl | 12.00 | 19.80 | 37.50 | q.s for pH |  | 4 |

TABLE 17-continued

| Ingredient | (%) add as is | actual weight | (%) actives in raw mtl | (%) active in ADW | Lot # | Order of addition |
|---|---|---|---|---|---|---|
| Kelzan T | | 1.49 | 100.00 | 0.50 | 35073K Kelco | 7 |
| Total | 100.08 | 300.00 | | | | |

The formulation was prepared as follows. The sodium citrate was added to deionized water and mixed well. The sodium silicate was added and mixed thoroughly to get an even solution with no precipitates. The pH was dropped to 10 with 37.5% HCl. HSE was prepared in accordance with Example 6. The HSE was added and mixed well, and MES (ALPHA-STEP MC-48) was added and mixed well. Kelzan T (thickener) was added and mixed well along with heating the solution to 40 C, so as to get the thickener completely into the solution without any lumps. The enzymes were added and mixed well.

The initial pH was 13.13 and the final pH (as is) at 25° C. was 10.40. The final appearance at 25° C. was a creamy straw colored viscous liquid. The viscosity as measured by Brookfield Viscometer LV, S63 at 50 rpm at 25° C. was 3200 cps.

The formulation was tested for its performance using a modified version of the Standard Method for "Deposition on Glassware During Mechanical Dishwashing" designated as ASTM-D3556-85. This test method covers a procedure for measuring performance of a mechanical dishwashing detergent in terms of the buildup of spots and film on glassware. It is designed to evaluate household automatic dishwasher detergents but also be used as a screening test for institutional dishwashing products. The method is modified in that the food-stuff was left to sit on the dishware overnight before the test was run. Briefly, 30.0 plus/minus 0.1 grams are used in a standard pots/pans cycle with 7 plates soiled with 5.7 grams each of shell soil in the bottom rack (40 grams total), and tumblers/silverware on the top rack for grading. The machine is loaded as follows: In the lower (plate) rack, the six soiled dinner plates are distributed uniformly with the smaller plates and bowls, if used, placed alternately about the dinner plates until the rack is fully loaded. In the upper (glass) rack, the glass tumblers are distributed evenly. Six each of the stainless steel knives, forks, and spoons are placed in the silverware rack or holder. Washing is done using a dishwasher with a water temperature of at least 130 6 5° F. (54.4 6 3.8° C.) in the dishwasher. The machine is preheated by running a preliminary cycle with the machine empty. The contents of the machine are allowed to cool to about 75° F. (23.9° C.) before making evaluations or starting another wash cycle. Three cycles of wash were performed, with the food soil reapplied after each one. The dishes are rated after each cycle. The tumblers are rated visually after each cycle for film and spotting. For these evaluations, the tumblers are viewed upside down in the light box described in 4.4 (in handling, pick up the tumblers by the base to avoid fingerprints on the sides). The following scale is used for rating the tumblers:

Rating Spotting Filming
  1: no spots
  2: spots at random barely perceptible
  3: about ¼ of surface covered slight
  4: about ½ of surface covered moderate
  5: virtually completely covered heavy Number ratings are obtained by averaging the ratings for individual tumblers, keeping spotting and filming results separate.

The remaining 2 cycles of testing were done on the formula of Table 16 per the modified ASTM D3556-85 in which the soil dries overnight. The results were as follows:
  Cycle 2: Grade=2.0; same as Cycle 1.
  Cycle 3: Grade=0.75—significantly better than first two cycles.

It appears that this formula cleans better as it is used, even though soiled plates are added each new cycle.

The results show that formulations of the present technology clean as well as an industrial standard Cascade Complete™, available from Procter and Gamble, Cincinnati, Ohio. Therefore, the present technology provides a substantially free of phosphates and chlorine formulation of dishwashing detergent that cleans as well as the industrial standard containing phosphates and chlorine. This example demonstrates that lowering the pH to around 10 keeps the enzyme stable and thus increases the performance. The same would also apply for the baseline formula for ADW with Makon NF-12 with enzymes.

Example 15

General Purpose Cleaner Formulation

This example demonstrates a general purpose cleaner composition, such as for hard surfaces, comprising a sulfo-estolide and an alkyl ester sulfonate. SE and HSE were evaluated by ASTM 4488 section A5 to determine the cleaning effectiveness of the formulations, and tested by a modified version of a filming and streaking method to determine effectiveness as hard surface cleaners. Table 18 shows the components used for a control formulation (formula A) and a formulation comprising a sulfo-estolide and an alkyl ester sulfonate (formula B). The sulfo-estolide was prepared in accordance with Example 6. In formula B, the sulfo-estolide is in place of Propylene glycol n-butyl ether in formula A, while the alkyl ester sulfonate (coco MES) is in place of sodium lauryl sulfonate (SLS).

TABLE 18

| | General purpose cleaner formulations | |
|---|---|---|
| Ingredients | A Control % wt | B Sulfo-estolide and alkyl ester sulfonate % wt |
| Bio-Soft EC-639 (C1214 8.2 EO) | 1.0 | 0.9 |
| Stepanol PCK (SLS) | 1.0 | — |
| Alpha-Step PC-48 (coco MES) | — | 0.3 |
| SE potassium | — | 4.0 |
| Diethylene glycol monobutyl ether (DB) | 4.0 | 4.0 |
| Propylene glycol n-butyl ether (PnB) | 4.0 | — |
| Sodium Citrate | 4.0 | 4.0 |
| deionized water | balance | balance |

The formulations were tested at a 1:4 dilution with deionized water, and the results of the testing are shown in Table 19. The test method for filming and streaking was as follows:
(1) Black tiles or mirror are cleaned with a standard spray and wipe glass cleaner. The tile was then rinsed with isopropyl alcohol and wiped dry.
(2) Ten drops of the hard surface cleaner sample were evenly applied around the hard surface material. The drops should be applied in a uniform pattern, size and shape on all of the hard surfaces.
(3) The treated tile is wiped with a quatered tissue which has been folded in half. The tissue is wiped across the tile's surface for ten cycles while applying light and uniform pressure. One cycle is equal to one back and forth motion.
(4) The hard surfaces are dried for a minimum of ten minutes.
(5) The hard surfaces are then visually evaluated and scored under well lighted conditions. The scoring of the streaking and filming performance is conducted using a plus or minus rating scale, where the control is set to zero and a positive score is indicative of superior performance.

TABLE 19

|  | A Control | B Sulfo-estolide and alkyl ester sulfonate |
|---|---|---|
| % soil removed | 72 | 78 |
| Filming | 0 | +0.5 |
| Streaking | 0 | +1 |

Unexpectedly, it was observed that sulfo-estolide can replace the propylene glycol n-butyl ether (PnB) solvent and yet appeared to maintain soil removal performance. In replacing the anionic surfactant, sodium lauryl sulfate, with sodium coco methyl ester sulfonate, it shows that other surfactants can be used in combination with the SE to give improved performance in filming and streaking.

CONCLUSION

The embodiments and examples described here are illustrative, and do not limit the presently described technology in any way. The scope of the present technology described in this specification is the full scope defined or implied by the claims. Additionally, any references noted in the detailed description section of the instant application are hereby incorporated by reference in their entireties, unless otherwise noted.

What is claimed is:
1. A light duty liquid detergent composition, comprising:
about 0.1% to about 90% active weight of the total composition of at least one sulfo-estolide surfactant having the following general Formula 1:

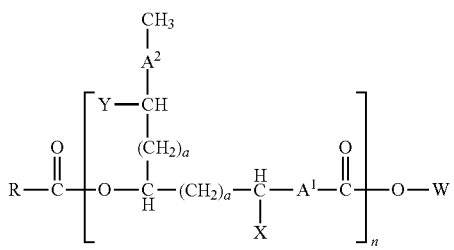

wherein n is an integer from 1-30 or a mixture thereof;
one of X and Y is $SO_3$—Z, the other of X and Y is H (i.e., a hydrogen atom), and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to 24;
W is H or a monovalent or divalent metal cation, ammonium cation, substituted ammonium cation, or an alkyl or substituted alkyl group; and
Z is H or a monovalent or divalent metal cation, ammonium or substituted ammonium cation;
about 0.1% to about 70% of at least one alkyl ester sulfonate;
about 0.5% to about 3% by weight of magnesium sulfate; and
about 1% to about 99.8% of at least one carrier.
2. A laundry detergent composition, comprising:
about 5% to about 99% by weight of at least one compound having the following general Formula 1:

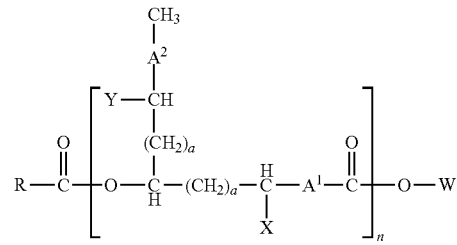

wherein n is an integer from 1-30 or a mixture thereof;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is a monovalent or divalent metal cation, ammonium cation, substituted ammonium cation, H, or an alkyl or substituted alkyl group;
Z is H, or a monovalent or divalent metal cation, ammonium or substituted ammonium cation;
about 1% to about 50% by weight of at least one alkyl ester sulfonate;
about 0.5% to about 3% by weight of magnesium sulfate;
0% to about 25% by weight of cocamide diethanolamine; and
wherein the composition has a pH value in the range of about 7 to about 10.
3. A laundry detergent composition, comprising:
about 2% to about 90% by weight of one or more compounds having the following general Formula 1:

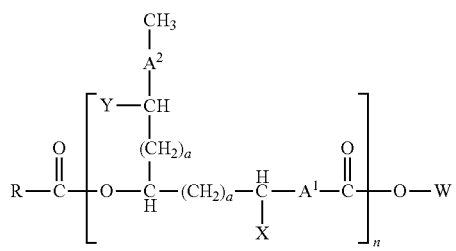

wherein n is an integer from 1-30 or a mixture thereof;
one of X and Y is SO$_3$—Z, the other of X and Y is H, and X and Y are independently assigned in each repeating unit;

A$^1$ and A$^2$ are linear or branched, saturated or unsaturated, substituted or unsubstituted alkyl diradicals wherein the total number of carbons for each repeating unit is independent and in the range of C$_8$ to C$_{22}$;

a is 0, 1, or 2, and is independently assigned in each repeating unit;

R is a linear or branched, saturated or unsaturated, substituted or unsubstituted alkyl radical with from 1 to 24 carbon atoms;

W is a monovalent or divalent metal cation, ammonium or substituted ammonium cation, H, or an alkyl or substituted alkyl group;

Z is H, or a monovalent or divalent metal cation, ammonium or substituted ammonium cation;

about 0.1% to about 25% by weight of at least one alkyl ester sulfonate;

about 0.5% to about 3% by weight of magnesium sulfate;

about 2% to about 40% by weight of at least one nonionic surfactant;

0% to about 32% by weight of at least one alcohol ether sulfate;

0% to about 6% by weight of lauryl dimethlyamine oxide;

0% to about 6% by weight of C$_{12}$EO$_3$;

0% to about 10% by weight of coconut fatty acid;

0% to about 3% by weight of borax pentahydrate;

0% to about 6% by weight of propylene glycol;

0% to about 10% by weight of sodium citrate;

0% to about 6% by weight of triethanolamine;

0% to about 6% by weight of monoethanolamine;

0% to about 1% by weight of at least one fluorescent whitening agent;

0% to about 1.5% by weight of at least one anti-redeposition agent;

0% to about 2% by weight of at least one thickener;

0% to about 2% by weight of at least one thinner;

0% to about 2% by weight of at least one protease;

0% to about 2% by weight of at least one amylase; and

0% to about 2% by weight of at least one cellulase.

4. A green laundry detergent composition, comprising:
about 2% to about 99.9% by weight of one or more compounds having the following general Formula 1:

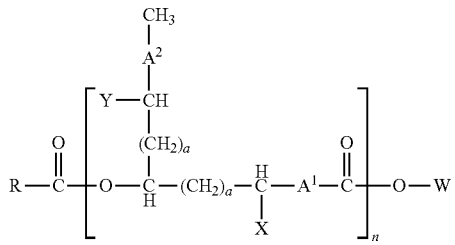

Formula 1 wherein n is an integer from 1-30 or mixture thereof;
one of X and Y is SO$_3$—Z, the other of X and Y is H, and X and Y are independently assigned in each repeating unit;

A$^1$ and A$^2$ are linear or branched, saturated or unsaturated, substituted or unsubstituted alkyl diradicals wherein the total number of carbons for each repeating unit is independent and in the range of C$_8$ to C$_{22}$;

a is 0, 1, or 2, and is independently assigned in each repeating unit;

R is a linear or branched, saturated or unsaturated, substituted or unsubstituted alkyl radical with from 1 to 24 carbon atoms;

W is a monovalent or divalent metal cation, ammonium or substituted ammonium cation, H, or an alkyl or substituted alkyl group;

Z is H, or a monovalent or divalent metal cation, ammonium or substituted ammonium cation;

about 0.1% to about 30% by weight of at least one alkyl ester sulfonate;

about 0.5% to about 3% by weight of magnesium sulfate;

0% to about 30% by weight of sodium lauryl sulfate;

0% to about 30% by weight of sodium stearoyl lactylate;

0% to about 30% by weight of sodium lauroyl lactate;

0% to about 60% by weight of alkyl polyglucoside;

0% to about 60% by weight of polyglycerol monoalkylate;

0% to about 30% by weight of lauryl lactyl lactate;

0% to about 30% by weight of saponin;

0% to about 30% by weight of rhamnolipid;

0% to about 30% by weight of sphingolipid;

0% to about 30% by weight of glycolipid;

0% to about 30% by weight of at least one abietic acid derivative; and

0% to about 30% by weight of at least one polypeptide.

5. The composition of claim 4, wherein at least one of the compounds of Formula 1 is a potassium salt.

6. A liquid personal care composition, comprising:
about 0.1% to about 99% by weight of at least one surfactant having the following general Formula 1:

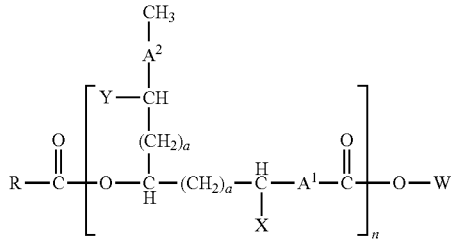

wherein n is an integer from 1-30 or a mixture thereof;

one of X and Y is SO$_3$—Z, the other of X and Y is H, and X and Y are independently assigned in each repeating unit;

A$^1$ and A$^2$ are linear or branched, saturated or unsaturated, substituted or un-substituted, alkyl diradicals wherein the total number of carbons for each repeating unit is independent and in the range of C$_8$ to C$_{22}$;

a is 0, 1, or 2, and is independently assigned in each repeating unit;

R is linear or branched, saturated or unsaturated, substituted or unsubstituted, wherein the total number of carbon atoms is from 1 to about 24;

W is H or a monovalent or divalent metal cation, ammonium cation or substituted ammonium cation, or an alkyl or substituted alkyl group;

Z is H or a monovalent or divalent metal cation, ammonium or substituted ammonium cation; and about 0.1% to about 85% by weight of at least one alkyl ester sulfonate; and about 1% to about 99.9% by weight of at least one carrier;

wherein the composition has a viscosity of about 10 to about 50,000 cps, measured at a temperature of 25° C., with a Brookfield model RVT viscometer set at a speed of 20 rpm.

7. The personal care composition of claim 6, further comprising at least one additive selected from the group consisting of viscosity modifiers, electrolytes, emollients, skin conditioning agents, emulsifier/suspending agents, fragrances, colors, herbal extracts, vitamins, builders, enzymes, pH adjusters, preservatives, antibacterial agents, antidandruff agents, derivatives thereof, and combinations thereof.

8. The personal care composition of claim 6, wherein the pH value is in the range of about 5 to about 7.

9. The personal care composition of claim 6, wherein the composition is a liquid hand soap.

10. The personal care composition of claim 6, wherein the composition is a body wash.

11. The personal care composition of claim 6, wherein the composition is a facial cleaner.

12. The personal care composition of claim 6, wherein the composition is a shampoo, a 2-in-1 shampoo or an antidandruff shampoo.

13. The personal care composition of claim 6, the composition has a total surfactant concentration of about 20% by weight or more.

14. A low-foaming liquid machine dishwashing detergent composition comprising:

about 0.1% to about 20% by active weight of one or more surfactants of the general Formula 1:

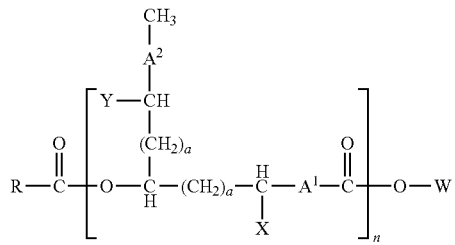

wherein n is an integer from 1-30 or a mixture thereof;
one of X and Y is SO$_3$—Z, the other of X and Y is H, and X and Y are independently assigned in each repeating unit;

A$^1$ and A$^2$ are linear or branched, saturated or unsaturated, substituted or un-substituted, alkyl diradicals wherein the total number of carbons for each repeating unit is independent and in the range of C$_8$ to C$_{22}$;

a is 0, 1, or 2, and is independently assigned in each repeating unit;

R is linear or branched, saturated or unsaturated, substituted or un-substituted, wherein the total number of carbon atoms is from 1 to about 24;

W is H or a monovalent or divalent metal cation, ammonium cation or substituted ammonium cation, or an alkyl or substituted alkyl group;

Z is H or a monovalent or divalent metal cation, ammonium or substituted ammonium cation;

about 0.1% to about 20% by active weight of at least one alkyl ester sulfonate;

about 0.01% to about 10% by active weight of at least one enzyme;

about 1% to about 99.9% by weight of at least one carrier; and one or more corrosion protecting agents; and wherein the low-foaming liquid machine dishwashing detergent composition has a pH from about 9 to about 14.

15. A hard surface cleaning composition, comprising:

about 1% to about 99% by weight of at least one surfactant having the following general Formula 1:

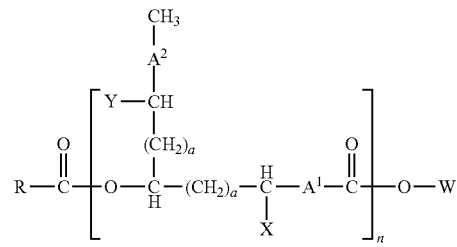

wherein n is an integer from 1-30 or a mixture thereof;
one of X and Y is SO$_3$—Z, the other of X and Y is H, and X and Y are independently assigned in each repeating unit;

A$^1$ and A$^2$ are linear or branched, saturated or unsaturated, substituted or un-substituted, alkyl diradicals wherein the total number of carbons for each repeating unit is independent and in the range of C$_8$ to C$_{22}$;

a is 0, 1, or 2, and is independently assigned in each repeating unit;

R is linear or branched, saturated or unsaturated, substituted or un-substituted hydrocarbon wherein the total number of carbon atoms is from 1 to 24;

W is H or a monovalent or divalent metal cation, ammonium cation, substituted ammonium cation, or an alkyl or substituted alkyl group; and Z is H or a monovalent or divalent metal cation, ammonium or substituted ammonium cation;

about 0.1% to about 85% of at least one alkyl ester sulfonate; and about 1% to about 99% of at least one carrier.

16. A laundry detergent composition, comprising:
a mixture of sodium and potassium salts of sulfo-estolides having the following general Formula 1:

1.

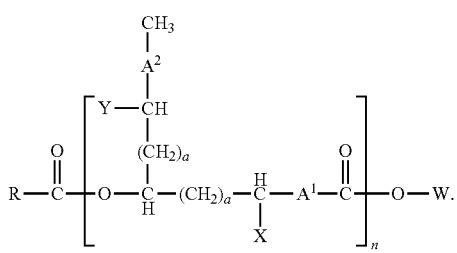

wherein n is an integer from 1-30 or a mixture thereof;
one of X and Y is SO3—Z, the other of X and Y is H, and X and Y are independently assigned in each repeating unit;

A1 and A2 are linear or branched, saturated or unsaturated, substituted or unsubstituted alkyl diradicals wherein the total number of carbons for each repeating unit is independent and in the range of C8 to C22;

a is 0, 1, or 2, and is independently assigned in each repeating unit;

R is a linear or branched, saturated or unsaturated, substituted or unsubstituted alkyl radical with from 1 to 24 carbon atoms;

W is a sodium or potassium cation, H, or an alkyl or substituted alkyl group;

Z is a sodium or potassium cation;

at least one alkyl ester sulfonate;

at least one carrier.

* * * * *